US007662940B1

(12) United States Patent
Baum et al.

(10) Patent No.: US 7,662,940 B1
(45) Date of Patent: Feb. 16, 2010

(54) **NUCLEOTIDE AND AMINO ACID SEQUENCES FROM *BACILLUS THURINGIENSIS* AND USES THEREOF**

(75) Inventors: James A. Baum, Webster Groves, MO (US); William P. Donovan, Manchester, MO (US); Brian B. Hauge, Wildwood, MO (US); Thomas J. LaRosa, Fenton, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/194,345

(22) Filed: Aug. 1, 2005

Related U.S. Application Data

(60) Provisional application No. 60/598,742, filed on Aug. 4, 2004.

(51) Int. Cl.
*C07H 21/00* (2006.01)
*A01H 1/00* (2006.01)
*A01H 5/00* (2006.01)

(52) U.S. Cl. .................. 536/23.1; 435/320.1; 435/410; 800/295; 800/278; 530/350

(58) Field of Classification Search ................ 536/23.1; 435/320.1, 325, 69.1, 252.3, 410; 530/350; 800/295, 278
See application file for complete search history.

(56) References Cited

OTHER PUBLICATIONS

Bowen et al., (1998), GenBank:AAC38623.*
Bowen et al., (1998), GenBank:AAC38624.*
Bowen et al., (1998), GenBank:AAC38625.*
Bowen et al., (1998), GenBank:AAC38630.*
Bowen et al. , Science 280 (5372) 2129-2132 (1998).*

* cited by examiner

*Primary Examiner*—Chih-Min Kam
(74) *Attorney, Agent, or Firm*—Timothy K. Ball

(57) ABSTRACT

Nucleic acid sequences and insecticidal proteins encoded from these sequences are provided. Insecticidal proteins encoded by large operons situated within the primary sequence of large extrachromosomal plasmids present in *Bacillus thuringiensis* are disclosed. Methods for making transgenic plants resistant to insect infestation as a result of expression of one or more of these proteins is disclosed. *Bacillus thuringiensis* strains exhibiting broad host range insecticidal specificity are also disclosed.

8 Claims, 1 Drawing Sheet

NUCLEOTIDE AND AMINO ACID SEQUENCES FROM *BACILLUS THURINGIENSIS* AND USES THEREOF

CROSS-REFERENCE TO RELATED APPLICATIONS

This application claims the benefit of priority to U.S. Provisional Application Ser. No. 60/598,742, filed Aug. 4, 2004.

FIELD OF THE INVENTION

The present invention relates to nucleic acid sequences from *Bacillus thuringiensis*, and, in particular, to DNA sequences that encode proteins from *B. thuringiensis* strains EG5858, EG4332 and EG4096 that, particularly when expressed together, exhibit insecticidal properties. In addition, proteins and fragments thereof, antibodies capable of binding specifically to the proteins, and methods of using the disclosed nucleic acid molecules, proteins, protein fragments and antibodies are disclosed. Protection from insect pest infestation either as a result of the in planta expression of the proteins disclosed herein, as a composition of matter that can be applied to the seeds as a seed coating or seed treatment, or as a pharmaceutical composition for treatment of insect pest infestation of animals or otherwise are contemplated.

BACKGROUND

The present invention relates to nucleic acid sequences from *Bacillus thuringiensis*, and, in particular, to genomic DNA sequences that encode insecticidal proteins from *B. thuringiensis* strains EG5858, EG4332 and EG4096. In addition, proteins and fragments thereof and antibodies capable of binding specifically to the proteins and methods of using the disclosed nucleic acid molecules, proteins, protein fragments and antibodies are encompassed by the present invention.

The gram-positive bacterium *Bacillus thuringiensis* is well known as a source of insecticidal proteins, most of which accumulate in crystalline inclusions during sporulation (Crickmore et al., Microbiol. Mol. Biol. Rev. 62:807-813, 1998; de Maagd, et al., Annu. Rev. Genet. 37:409-433, 2003; Schnepf et al., Microbiol. Mol. Biol. Rev. 62:775-806, 1998). These crystal proteins, or Cry proteins, are diverse and include distinct protein families as judged by amino acid sequence analysis and structural information derived from X-ray crystallography. A comprehensive listing of known BT insecticidal proteins, genes, and information about the nomenclature associated with these genes and proteins can be accessed at the web site biols.susx.ac.uk/home/Neil_Crickmore/Bt/index.htmL. A variety of crystalline Bt insecticidal proteins are known. These proteins collectively display a wide range of activity against insect pests, including those from the orders Lepidoptera, Coleoptera, Diptera, Hemiptera, Hymenoptera, and Heteroptera. In addition to the delta-endotoxin crystal proteins, *B. thuringiensis* strains also produce secreted insecticidal proteins that are expressed during vegetative growth, including VIP1-, Vip2-, and Vip3-type proteins, TIC901 and related proteins, and TIC900 and related proteins.

The use of Cry proteins in agriculture for insect control has been advanced by the development of transgenic crops. Transgenic crops expressing *B. thuringiensis* cry genes have enjoyed an unprecedented rate of adoption by farmers in the United States and elsewhere since their introduction in the 1990s. Worldwide acreage of all transgenic crops in 2002 was reported to be approximately 58.7 million hectares, or 145 million acres, representing a 12% increase over year 2001 acreage (James C., ISAAA Briefs No. 27. ISAAA, Ithaca, N.Y., 2002). The long term success of this transgenic approach to insect control will depend on appropriate insect resistance management (IRM) strategies. An important component of a sustainable IRM strategy is the discovery and deployment of new insecticidal proteins with distinct modes-of-action that either prevent or significantly delay the development of widespread resistance among insect pest populations.

Other bacteria besides *B. thuringiensis* display insecticidal properties that may in part be attributed to insecticidal proteins. The gram-negative bacteria *Photorhabdus luminescens, Xenorhabdus nematophilus* and related species, *Serratia entomophila, Pseudomonas syringae*, and *Yersinia pestis* all express insecticidal proteins. Each of these species have also been shown to produce a large extracellular multiprotein complex consisting primarily of TC proteins (toxin complex). Each of the proteins within the complex individually have generally failed to display insecticidal activity (ffrench-Constant and Bowen, Curr. Opin. Microbiol. 2:284-2880, 1999; ffrench-Constant et al., FEMS Microbiol. Rev. 759:1-24, 2002; Waterfield et al., Trends Microbiol. 9:185-191, 2001). In addition to the tc-like genes, other insect virulence genes such as the mcf genes have been discovered (Waterfield, et al., FEMS Microbiol. Lett. 229:265-270, 2003). The tc homologs and mcf genes could be a valuable source of insect-resistance traits for future transgenic crops because they are unrelated to the *B. thuringiensis* cry genes and therefore likely exhibit different modes of action. Recently, genes encoding proteins that exhibited similarity to the TC proteins were also identified in a gram-positive bacterium identified as a *Paenibacillus* species (US Patent Application Publication No. 2004/0110184). *Paenibacillus* bacteria have been determined to be phylogenetically unrelated with any other bacteria including other aerobic, endospore-forming bacilli based upon rRNA and phenotypic characteristics (Ash et al., Antonie Van Leeuwenhoek 64:253-260, 1993).

There is a continuing need to identify additional genes that encode insecticidal proteins useful in producing insect resistant transgenic plants. With few exceptions, Bt crystalline insecticidal proteins all seem to exhibit a similar structural and functional motif. The proteins generally exhibit a conserved three-dimensional structure based on x-ray crystallographic studies of several members of the Bt delta-endotoxin family. Generally, the proteins also exhibit a similar mode of action in that they all bind in a specific fashion to membranes surfaces within the midgut of the larval form of a particular target insect species and subsequently form ion-channel pores that result in a disruption of the membrane potential along the surfaces of the membrane, which generally results in the death or incapacitation of the larval form of the target insect. Transgenic plants expressing these proteins have been demonstrated to be effective in minimizing insect infestation, however, there is a concern that insect populations repeatedly exposed to these insect resistant plants could develop resistance to the Bt toxin produced within the plants. Therefore, there is a need to identify additional insecticidal proteins that are different from the typical Bt insecticidal crystal protein and that exert their insecticidal effects through a mode of action that is also different from the typical Bt insecticidal crystal protein.

*Bacillus thuringiensis* strains are not known that exhibit insecticidal activity against a diversity of insect targets. Generally, *B. thuringiensis* strains exhibit insecticidal activity against one or at most two orders of insect species, such as for example, against Dipteran and Lepidopteran insect species. The inventors herein have identified three strains of *B. thuringiensis* that surprisingly exhibit insecticidal activity against a diversity of insect orders including Lepidoptera, Coleoptera, Diptera, and Hemiptera. Bt insecticidal proteins are known to be expressed from genes located on extrachromosomal megadalton plasmids. It was believed that such broad insecticidal diversity exhibited by these strains was a result of expression of one or more toxin genes located within one or more megadalton plasmids in each of these strains. The inventors herein have identified an operon within one of these strains that contains genes encoding proteins that exhibit similarity to the gram-negative TC proteins. In addition, the genes within the *B. thuringiensis* operon substantially maintain the order of expression of the gram-negative genes described above.

SUMMARY OF THE INVENTION

The invention provides isolated and purified nucleic acid sequences as set forth in SEQ ID NO:1, SEQ ID NO:8, SEQ ID NO:10, SEQ ID NO:12, SEQ ID NO:14, and SEQ ID NO:16 that encode, either alone or in combination, insecticidal proteins. SEQ ID NO:1 comprises an operon encoding insecticidal proteins as set forth in SEQ ID NO:2, SEQ ID NO:3, SEQ ID NO:4, SEQ ID NO:5, and SEQ ID NO:6 referred to respectively herein as TIC813, TIC814, TIC816, TIC817, and TIC818. SEQ ID NO:2 is a 1088 amino acid sequence encoded from an open reading frame as set forth in SEQ ID NO:1 from about nucleotide position 1428 through about nucleotide position 4691. SEQ ID NO:3 is a 1205 amino acid sequence encoded from an open reading frame as set forth in SEQ ID NO:1 from about nucleotide position 4722 through about nucleotide position 8336. SEQ ID NO:4 is a 1458 amino acid sequence encoded from an open reading frame as set forth in SEQ ID NO:1 from about nucleotide position 8400 through about nucleotide position 12773. SEQ ID NO:5 is a 921 amino acid sequence encoded from an open reading frame as set forth in SEQ ID NO:1 from about nucleotide position 12981 through about nucleotide position 15743. SEQ ID NO:6 is a 927 amino acid sequence encoded from an open reading frame as set forth in SEQ ID NO:1 from about nucleotide position 15803 through about nucleotide position 18583. SEQ ID NO:9, referred to herein as TIC815, is a 1205 amino acid sequence encoded from an open reading frame as set forth in SEQ ID NO:8 from about nucleotide position 1 through about nucleotide position 3615. SEQ ID NO:11, referred to herein as TIC904, is a 1081 amino acid sequence encoded from an open reading frame as set forth in SEQ ID NO:10 from about nucleotide position 1 through about nucleotide position 3243. SEQ ID NO:13, referred to herein as TIC905, is a 1203 amino acid sequence encoded from an open reading frame as set forth in SEQ ID NO:12 from about nucleotide position 1 through about nucleotide position 3609. SEQ ID NO:15, referred to herein as TIC906, is a 1455 amino acid sequence encoded from an open reading frame as set forth in SEQ ID NO:14 from about nucleotide position 1 through about nucleotide position 4365. SEQ ID NO:17, referred to herein as TIC912, is a 927 amino acid sequence encoded from an open reading frame as set forth in SEQ ID NO:16 from about nucleotide position 1 through about nucleotide position 2784. Purified and isolated amino acid sequences are provided comprising the amino acid sequences as set forth in SEQ ID NO's:2-6, SEQ ID NO:9, SEQ ID NO:11, SEQ ID NO:13, SEQ ID NO:15, and SEQ ID NO:17, and insecticidal fragments thereof. These proteins, alone or in combination, are toxic to a wide range of insect species including but not limited to insects of the order Coleoptera, Lepidoptera, Diptera, and Hemiptera.

In another embodiment, the present invention provides a substantially purified protein isolated from *B. thuringiensis* cell or media from in which the cell was grown, comprising an amino acid sequence that exhibits at least from about 70% to about 100% amino acid sequence identity to an amino acid sequence selected from the group consisting of SEQ ID NO:2, SEQ ID NO:3, SEQ ID NO:4, SEQ ID NO:5, SEQ ID NO:6, SEQ ID NO:9, SEQ ID NO:11, SEQ ID NO:13, SEQ ID NO:15, and SEQ ID NO:17.

In a further embodiment, the invention also relates to a biologically pure culture of a *B. thuringiensis* bacterium selected from the group consisting of strain EG5858, strain EG4332, and strain EG4096.

The invention also provides a vector comprising a nucleotide sequence selected from the group consisting of SEQ ID NO:1, SEQ ID NO:8, SEQ ID NO:10, SEQ ID NO:12, SEQ ID NO:14, and SEQ ID NO:16 or the complement thereof.

In yet a further embodiment, the invention provides plants and plant cells that have been transformed with a nucleotide sequence encoding a protein as set forth in any of SEQ ID NO:2, SEQ ID NO:3, SEQ ID NO:4, SEQ ID NO:5, SEQ ID NO:6, SEQ ID NO:9, SEQ ID NO:11, SEQ ID NO:13, SEQ ID NO:15, and SEQ ID NO:17 and insecticidal fragments thereof.

In yet a further embodiment, the present invention also provides a method for producing a transgenic plant resistant to infestation by insect pests selected from the orders Coleoptera, Lepidoptera, Diptera, and Hemiptera, as a result of increased expression levels of one or more proteins selected from the group consisting of TIC813, TIC814, TIC815, TIC816, TIC817, TIC818, TIC904, TIC905, TIC906 and TIC912, and insecticidal fragments thereof or chimeras thereof.

Another embodiment of the present invention is the provision for antibodies that bind specifically to epitopes presented only by any of the proteins as set forth in TIC813, TIC814, TIC815, TIC816, TIC817, TIC818, TIC904, TIC905, TIC906 and TIC912 and homologs and form immunological complexes. Antibodies can be used for identifying the presence of any one of the proteins or homolog, for purifying any one of the proteins or homolog, for identifying a nucleotide sequence from which any one of the proteins or homolog is being expressed, and for use in kits designed to allow the detection of any one of the proteins or homolog or the detection of a nucleotide sequence expressing any one of the proteins or homolog.

Another embodiment of the present invention provides for host cells transformed to contain a polynucleotide encoding an insecticidal protein of the present invention or an insecticidal fragment thereof. Preferably the nucleotide sequences of the present invention are modified to improve expression of the proteins of the present invention in a preferred host cell. The host cell of the present invention is selected from the group consisting of a bacterial cell, a fungal cell, an algal cell and a plant cell. Expression in a plant cell can comprise expression to achieve accumulation of the insecticidal protein in the cytoplasm, or can result in the insecticidal protein being accumulated into a subcellular organelle such as a plastid, chloroplast, or mitochondria. Alternatively the insecticidal protein of the present invention or insecticidal fragments thereof could be localized to the protein secretion machinery of the particular host cell and result in an accumulation of the protein product out side of the cell and into the extracellular spaces surrounding the cell.

An additional embodiment of the present invention provides a method for controlling infestation of a plant by an insect species. Preferably a pesticidal amount of an insecticidal protein of the present invention or insectidal fragment thereof is provided for consumption by the insect pest in the diet of the insect. The diet can consist of a plant part that the insect normally feeds upon, such as a plant tissue or plant cell. The insecticidal protein or insecticidal fragment thereof can be provided in a composition that is applied to the surface of the plant tissue, plant part, or plant cell or more preferably can be produced by the protein synthesis machinery of the cell and, as described above, accumulated within the plant cell or secreted outside of the plant cell, so long as the amount of the protein toxin provided is an insecticidal amount sufficient to inhibit the insect pest from further feeding, or to inhibit the further growth and development of the insect pest, or to cause mortality to the insect pest. The diet provided to the insect can also be an artificial diet that contains the toxin protein uniformly distributed within or topically applied to the exposed surface(s) of the diet substrate, or included as a concentration gradient within or topically applied to the exposed surface(s) of the diet substrate. The insecticidal toxin or fragment thereof is derived from a nucleotide sequence that is encoded in *B. thuringiensis* by a nucleotide sequence that hybridizes under stringent conditions to the nucleotide sequence substantially complementary to any of SEQ ID NO:1, SEQ ID NO:8, SEQ ID NO:10, SEQ ID NO:12, SEQ ID NO:14, and SEQ ID NO:16 or the complement thereof.

Kits for detecting the presence of the nucleotide sequences of the present invention, as well as probes, primers, analogues and derivatives of the same, are also contemplated. Such kits contain one or more nucleotide sequences each for use either as a probe for detecting the presence of a nucleotide sequence encoding an insecticidal protein of the present invention or fragment thereof or related nucleotide sequences, or for use in combination with one or more other probes or primers included in such kit for amplifying one or more sequences of the present invention or a related nucleotide sequence. Such kits could also or alternatively contain antibody specifically binding to one or more peptides or the proteins of the present invention, as well as reagents for use with the probe or antibody, and the kits would also contain control samples for use in ensuring that the nucleotides or peptides identified with the probe and or antibody and reagents were functioning according to the manufacturers' instructions. All of the reagents necessary for carrying out the methods of identification of either nucleotide sequences or peptides would be packaged together in a kit along with instructions for use. An exemplary kit will contain a nucleotide sequence derived from a tic813, tic814, tic815, tic816, tic817, tic818, tic904, tic905, tic906 and/or tic912 or related protein coding sequence along with a sample of nucleotide sequence amplification primers, together with the reagents necessary for carrying out an amplification reaction, all packaged together in the kit.

It is therefore contemplated that the compositions and methods disclosed by the present invention will provide many advantages over the prior art including those specifically outlined above. In addition, the present invention provides an entirely new class of insecticidal proteins and nucleotide sequences encoding these proteins that were identified and isolated from *B. thuringiensis* and that were not previously known in the art. Other specific embodiments of the invention are disclosed in the following detailed description.

DETAILED DESCRIPTION OF PREFERRED EMBODIMENTS

Figure 1:
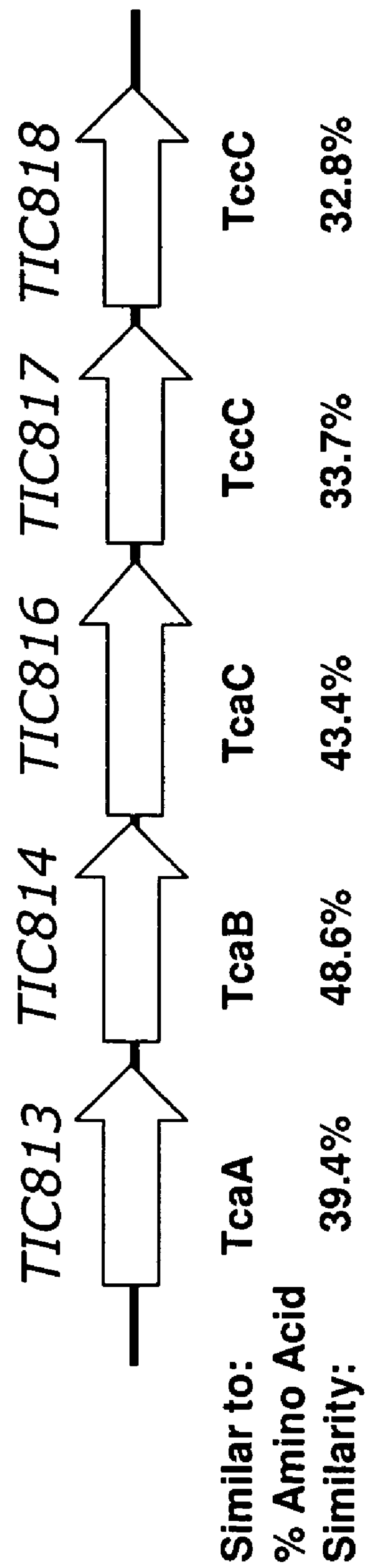
FIG. 1 shows a schematic map of the EG5858 operon sequence encoding insecticidal proteins TIC813, TIC814, TIC816, TIC817, and TIC818, along with information below each gene position about the extent to which each protein exhibits similarity at the amino acid sequence level to a corresponding *Photorhabdus* species homolog.

The inventors herein disclose the identification of nucleotide sequences encoding a new class of *Bacillus thuringiensis* insecticidal proteins that until recently, homologs of which were only known to be produced by gram negative bacterial species. TC proteins known previously from *Photorhabdus* and *Xenhorabdus* species in particular were characterized as being expressed from large polycistronic operons within the chromosomal genome of these gram negative bacterial species. The TC proteins have generally only been demonstrated to exhibit insecticidal properties when three or more of the proteins are expressed together. These proteins are known to form large extracellular complexes when expressed from their natural hosts. Typically these proteins are expressed from genes that previously were only known to be present in gram negative bacterial species, and in particular, in bacterial species that were known to exist in nature in a saprophytic relationship with entomopathogenic nematode species or free living bacteria such as *Serratia* and *Yersinia* species that are well known entomopathogenic species. Therefore, it was surprising to find an operon, genes, and proteins encoded from these genes that exhibited any similarity to such genes and proteins from gram negative bacterial species in a species as distantly related as *Bacillus thuringiensis.*

The genes and proteins of the present invention can be identified from any species of *Bacillus thuringiensis*, or any closely related *Bacillus* species such as *Bacillus popilleae, Bacillus cerus, Bacillus subtilis*, and *Bacillus megaterium* for example. Identification of a strain of a *Bacillus* that exhibits insecticidal activity against a diversity of target insects, in particular across several orders of insecta, provides one means for selecting a *B. thuringiensis* strain that may contain genes that hybridize to the sequences disclosed herein, and that encode insecticidal proteins.

*Bacillus thuringiensis* strains that exhibit insecticidal activity against a diversity of insect targets are not generally known. Typically, *B. thuringiensis* strains exhibit insecticidal activity against one or at most two orders of insect species, such as for example, against Dipteran and Lepidopteran insect species. The inventors herein have identified three strains of *B. thuringiensis* that surprisingly exhibit insecticidal activity against a diversity of insect orders including Lepidoptera, Coleoptera, Diptera, and Hemiptera. Bt insecticidal proteins are known to be expressed from genes located on extrachromosomal megadalton plasmids. It was believed that such broad insecticidal diversity exhibited by these strains was a result of expression of one or more toxin genes located within one or more megadalton plasmids in each of these strains. The inventors identified an operon within one of these strains that contains genes encoding proteins that exhibit similarity to the gram-negative TC proteins. In addition, the genes within the *B. thuringiensis* operon substantially maintain the order of expression of the gram-negative genes described above.

The inventors herein first purified extrachromosomal megadalton plasmids from the Bt strains EG5858, EG4332, and EG4096. These strains have each been deposited on Aug. 6, 2004 with the NRRL International Depositary Authority according to the Budapest Treaty, and provided with the strain deposit designations NRRL-B-30760, NRRL-B-30759, and NRRL-B-30758 respectively. The isolated megadalton plasmids were used to construct libraries in cloning vectors (high to medium copy number plasmids known in the art) and the sequences of the megadalton plasmid DNA's that were inserted into the cloning vectors were determined using a high throughput sequencing effort. Sequences identified in this way were analyzed for the presence of open reading frames, and these were then compared using typical genomics BLASTX methods to identify similar amino acid sequences present in the art within various databases. It was not unexpected to find an abundance of crystal protein coding sequences. However, a more interesting group of sequences were identified with top BLASTX hits that corresponded to *Photorhabdus* TC insecticidal sequences known previously to only be present in gram negative bacteria. While the Bt sequences derived from megadalton plasmid DNA's were at that stage of discovery only preliminary, it was clear from the number of sequences that were being identified within a plasmid library from EG5858 that additional sequence information from up and down stream of the sequences identified in the BLASTX searches may provide further information about whether these sequences were the result of individual sequences randomly dispersed within the Bt megadalton plasmid sequence, or whether, like the arrangement of the genes encoding the TC proteins in *Photorhabdus*, the genes were tightly linked and perhaps even within a common operon.

Additional sequencing and alignment revealed that several of the genes, in particular the genes encoding the TIC813, TIC814, TIC816, TIC817, and TIC818 proteins were indeed linked as part of an operon or gene cluster as set forth in SEQ ID NO:1. SEQ ID NO:1 corresponded to a large contiguous sequence assembled from a multitude of sequences first identified from the library sequencing efforts, followed up with sequencing out from the ends of each of those sequences to identify regions of overlapping identity either using inverse thermal amplification or chromosomal walking type methods. SEQ ID NO:1 consists of 20,944 consecutive nucleotides within one of the megadalton plasmids present in Bt strain EG5858. SEQ ID NO:1 contains at least five open reading frames that appear to be a part of a large operon expressing proteins that likely assemble outside of the Bt cell into a complex that exhibits broad insecticidal bioactivity. SEQ ID NO:2 corresponds to a 1,088 amino acid sequence encoded from an open reading frame as set forth in SEQ ID NO:1 from about nucleotide position 1,428 through about nucleotide position 4,691. SEQ ID NO:3 corresponds to a 1,205 amino acid sequence encoded from an open reading frame as set forth in SEQ ID NO:1 from about nucleotide position 4,722 through about nucleotide position 8,336. SEQ ID NO:4 corresponds to a 1,458 amino acid sequence encoded from an open reading frame as set forth in SEQ ID NO:1 from about nucleotide position 8,400 through about nucleotide position 12,773. SEQ ID NO:5 corresponds to a 921 amino acid sequence encoded from an open reading frame as set forth in SEQ ID NO:1 from about nucleotide position 12,981 through about nucleotide position 15,743. SEQ ID NO:6 corresponds to a 927 amino acid sequence encoded from an open reading frame as set forth in SEQ ID NO:1 from about nucleotide position 15,803 through about nucleotide position 18,583. SEQ ID NO:7 corresponds to an amino acid sequence that has not bee fully characterized because the 3' end of the open reading frame has not yet been identified. SEQ ID NO:7, referred to herein as TICXAX, corresponds to an amino acid sequence deduced from the open reading frame present at nucleotide sequence position 19,886 through the end of the sequence as set forth in SEQ ID NO:1. A BLAST comparison of the amino acid sequence as set forth in SEQ ID NO:7 resulted in a best hit with a protein known only from *Bacillus cereus* strain ATCC10987 and referred to in GenBank as AAS45028.1. The *B. cereus* protein exhibited about 77% amino acid sequence identity to the TICXAX protein. No known function has been associated with the *B. cereus* protein. However, the *B. cereus* protein was also derived from an extrachromosomal plasmid, and likely could be associated with a gene cluster similar to that observed in strain EG5858. Other less related sequence hits based on the BLASTP comparison resulted in proteins exhibiting a lesser similarity to the TICXAX protein but indicated a relationship to one or more transposase sequences.

BLASTX comparisons of the open reading frames as set forth in SEQ ID NO:1 resulted in the best alignments exhibiting less than about 50% amino acid sequence identity with the deduced amino acids encoded from these open reading frames. All of the best hits corresponded to TC proteins from *Photorhabdus* species. The best hit corresponding to the amino acid sequence as set forth in SEQ ID NO:2 corresponded to a TcaA protein as set forth in GenBank Accession No. AAC38623, but exhibited only about 39% amino acid sequence identity to SEQ ID NO:2. The best hit corresponding to the amino acid sequence as set forth in SEQ ID NO:3 corresponded to a TcaB protein as set forth in GenBank Accession No. AAC38624, but exhibited only about 49% amino acid sequence identity to SEQ ID NO:3. The best hit corresponding to the amino acid sequence as set forth in SEQ ID NO:4 corresponded to a TcaC protein as set forth in GenBank Accession No. AAC38625, but exhibited only about 43% amino acid sequence identity to SEQ ID NO:4. The hit exhibiting the greatest amino acid sequence identity to SEQ ID NO:5 corresponded to a TccC as set forth in GenBank Accession No. AAC38630, but exhibited only about 34% amino acid sequence identity to SEQ ID NO:5. The hit exhibiting the greatest amino acid sequence identity to SEQ ID NO:6 also corresponded to TccC as set forth in GenBank Accession No. AAC38630, but exhibited only about 33% amino acid sequence identity to SEQ ID NO:5.

Libraries were also produced from isolated megadalton plasmids derived from Bt strains EG4332 and EG4096 and the nucleotide sequences of inserted DNA's were obtained and analyzed. One clone from EG4332 provided identical nucleotide sequence information when compared to a clone containing the nucleotide sequence as set forth in SEQ ID NO:1 for the sequence encoding TIC814. Subsequent nucleotide sequence information with respect to the flanking sequences normally linked to this sequence in the native megadalton plasmid from EG4332 revealed that the ORF was identical to that encoding TIC814. This sequence from EG4332 is provided herein as SEQ ID NO:8 and the amino acid sequence deduced from that clone is set forth herein as SEQ ID NO:9.

Sequence analysis of the inserted DNA's from megadalton plasmids derived from EG4096, including BLASTX comparisons of nucleotide sequence databases also revealed numerous sequences that exhibited amino acid sequence identity to *Photorhabdus, Serratia entomophila, Xenorhabdus nematophilia*, and *Yersinia pestis* TC proteins. The sequences most closely related to EG4096 sequences included those encoding *Photorhabdus* TcaA, TcaB, TcaC and TccC proteins. Assembly of several nucleotide sequences that provided the strongest BLASTX hits revealed incomplete open reading frames. Complete open reading frames were subsequently identified from the EG4096 libraries and proteins deduced from these exhibited greatest similarity to the *Photorhabdus* TC proteins TcaA, TcaB, and TcaC. EG4096 genes corresponding to these homologs were designated as tic904, tic905, tic906 and tic912 (SEQ ID NO:10, SEQ ID NO:12, SEQ ID NO:14 and SEQ ID NO:16, respectively) encoding the insecticidal proteins TIC904, TIC905, TIC906, and TIC912 (SEQ ID NO:11, SEQ ID NO:13, SEQ ID NO:15 and SEQ ID NO:17, respectively). A comparison of the amino acid sequences of the TIC904-906 and TIC912 proteins to the *Photorhabdus* homologs revealed that none of the proteins exhibited more than about 50% amino acid sequence identity. TIC904 exhibited about 39% amino acid sequence identity to a *Photorhabdus* TcaA protein (GenBank Accession No. AAC38623). TIC905 exhibited about 50% amino acid sequence identity to a *Photorhabdus* TcaB protein (GenBank Accession No. AAC38624). TIC906 exhibited about 42% amino acid sequence identity to a *Photorhabdus* TcaC protein (GenBank Accession No. AAC38625). TIC912 exhibited about 43% amino acid sequence identity to a *Photorhabdus* TccC3 protein (GenBank Accession No. CAE13262). These three genes encoding the TIC904-906 amino acid sequences were determined to be within a single operon, similar to the size of the operon as set forth in SEQ ID NO:1.

Pairwise sequence comparisons between the proteins encoded by EG4096 genes and proteins encoded by EG5858 genes demonstrated surprising sequence diversity between the Bt homologs. TIC813 appeared to be most closely related to TIC904 yet these only exhibited about 61% amino acid sequence identity. TIC814 appeared to be most closely related to TIC905 yet these exhibited only about 63 amino acid sequence identity. Discounting the identity between TIC814 and TIC815, the strongest identity existed between TIC816 and TIC906 in which these exhibited only about 68% amino acid sequence identity.

The nucleotide sequences of the present invention that encode the proteins of the present invention exhibit from about 60 to about 70% A+T content. Experience has taught that plants ineffectively express such AT rich sequences, and so it is particularly important to ensure that sequences such as these, when intended for use in plants, be modified to remove problematic sequences before transgenic plants are produced that are expected to express the proteins of the present invention. An example of methods for modifying BT nucleotide sequences for improved expression in plants can be found in Fischhoff et al. (U.S. Pat. No. 5,500,365).

Nucleotide sequences designed for expression in heterologous cell systems require particular promoters that function in the heterologous cell systems. Depending on the application the promoter used to transcribe the expression of the insecticidal protein or proteins may be constitutive, tissue specific or inducible. See U.S. Pat. Nos. 5,858,742 and 5,322,938 which disclose versions of the constitutive e promoter derived from cauliflower mosaic virus (CaMV35S), U.S. Pat. No. 5,641,876 which discloses a constitutive rice actin promoter, U.S. Pat. No. 6,429,357 which discloses a constitutive rice actin 2 promoter and intron and U.S. Pat. No. 6,177,611 which discloses constitutive maize promoters. See U.S. Pat. Nos. 5,837,848; 6,437,217 and 6,426,446 which disclose root specific promoters and U.S. Pat. No. 6,433,252 which discloses a maize L3 oleosin promoter. See also U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters and U.S. Patent Application Publication 2004/0123347 A1 which discloses water deficit inducible promoters.

In transformation practice DNA is introduced into only a small percentage of target cells in any one transformation experiment. Marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS). Examples of such selectable are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

Methods and compositions for transforming plants by introducing a recombinant DNA construct into a plant genome in the practice of this invention can include any of the well-known and demonstrated methods. A preferred method of plant transformation is microprojectile bombardment as illustrated in U.S. Pat. Nos. 5,015,580 (soy), 5,550,318 (corn), 5,538,880 (corn), 6,153,812 (wheat), 6,160,208 (corn), 6,288,312 (rice) and 6,399,861 (corn). Another preferred method of plant transformation is *Agrobacterium*-mediated transformation as illustrated in U.S. Pat. Nos. 5,159,135 (cotton), 5,824,877 (soy), 5,591,616 (corn) and 6,384,301 (soy). All of the above-described patents disclosing materials and methods for plant transformation are incorporated herein by reference. See also U.S. Patent Application Publication 2003/0167537 A1, incorporated herein by reference, for a description of vectors, transformation methods, and production of transformed *Arabidopsis thaliana* plants where transcription factors are constitutively expressed by a CaMV35S promoter.

Transformation methods to provide plants with stably-integrated enhanced anti-sense gene suppression DNA constructs are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Those cells which are capable of proliferating as callus also are recipient cells for genetic transformation. Practical transformation methods and materials for making transgenic plants of this invention, e.g. various media and recipient target cells, transformation of immature embryos and subsequent regeneration of fertile transgenic plants are disclosed in U.S. Pat. Nos. 6,194,636 and 6,232,526 and U.S. application Ser. No. 09/757,089, which are incorporated herein by reference.

The seeds of transgenic plants can be harvested from fertile transgenic plants and used to grow progeny generations of transformed plants of the present invention including hybrid plant lines comprising the recombinant DNA construct expressing one or more of the insecticidal proteins of the present invention.

In addition to direct transformation of a plant with a recombinant DNA construct, transgenic plants can be prepared by crossing a first plant having a recombinant DNA construct with a second plant lacking the construct. For example, recombinant DNA can be introduced into a plant line that is amenable to transformation to produce a transgenic plant which can be crossed with a second plant line to introgress the recombinant DNA into the second plant line.

A transgenic plant with recombinant DNA expressing a protein of the present invention can be crossed with plant line having other recombinant DNA that confers another trait, e.g. yield improvement, herbicide resistance or other pest resistance to produce progeny plants having recombinant DNA that confers both insect resistance derived from the protein(s) of the present invention and the other trait. Typically, in such breeding for combining traits the transgenic plant donating the additional trait is a male line and the transgenic plant carrying the base traits is the female line. The progeny of this cross will segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, e.g. usually 6 to 8 generations, to produce a progeny plant with substantially the same genotype as one original transgenic parental line but for the recombinant DNA of the other transgenic parental line.

EXAMPLES

Example 1

This example illustrates the selection of Bt strains and the purification of extrachromosomal mega-dalton sized plasmids from Bt strains.

*B. thuringiensis* strains EG5858, EG4332, and EG4096 are unusual BT strains identified in bioassay screening because they each exhibit significant activity against lepidopteran, coleopteran, dipteran and hemipteran pests. *B. thuringiensis* strains generally do not exhibit a spectrum of insecticidal bioactivity that extends beyond more than two genera. Some BT insecticidal proteins, such as Cry2 proteins, have been shown to exhibit insecticidal activity toward lepidopteran and to dipteran species. However, it is unusual for Bt strains to exhibit such broad host range biological activity. In addition, the insecticidal bioactivity displayed by specific Bt proteins has been demonstrated to arise from the expression of genes located on extrachromosomal megadalton virulence plasmids. Therefore, it was suspected that the solution to the unusual activity spectrum displayed by these particular BT strains could be found within the primary nucleotide sequence structure of one or more of the plasmids present in these strains. Therefore, megadalton plasmids from each of these strains were purified and plasmid libraries were constructed from each purified megadalton plasmid and the nucleotide sequence of the inserted DNA's were identified using a genomics shotgun sequencing approach.

The following procedures for preparation of EG5858 cells and for field inversion gel electrophoresis were developed to resolve and isolate the large virulence plasmids present in strain EG5858. Plasmids were isolated and subject to similar treatments with the other two strains identified herein.

Plasmid was isolated from a sporulated culture of EG5858 that was inoculated into 2 mL of T broth (Sigma catalog T9179, Sigma, St. Louis, Mo.) in a sterile 12 mL tube and shaken at 250 rpm, 30° C. for 17 hours. Two-hundred μL of the culture was centrifuged, the supernatant discarded, and the cell pellet resuspended in 100 μL of TESL buffer (20% w/v sucrose, 20 mM Tris.HCl pH 7, 1 mM EDTA, 2 mg/mL lysozyme, 30 μg/mL Rnase A). The cells were incubated at 37° C. for 40 min. with occasional gentle shaking. An 80 mL 0.6% w/v agarose gel was prepared with 0.5×TBE (45 mM Tris, 45 mM boric acid, 1 mM EDTA disodium, pH 8) in a Bio-Rad CHEF Mapper® Cell according to the manufacturers instructions (Bio-Rad Laboratories, Hercules, Calif.). The agarose gel was exposed to a pre-run field inversion electrophoresis in 0.5×TBE with the following parameters: refrigeration 14° C.; buffer circulation speed 1,300 mL/min.; program setting 180° field inversion; forward voltage gradient at 8.0 V/cm; initial forward switch time at 1.6 seconds; final forward switch time at 2.4 seconds; reverse voltage at 8 V/cm; initial reverse switch time at 0.4 seconds; and final reverse switch time at 0.6 seconds. A total of running time was 10 min. Fifteen microliters of TESSB buffer (20% w/v sucrose, 20 mM Tris HCl pH 7, 1 mM EDTA, 4% w/v sodium dodecyl sulfate, 0.3 mg/mL bromophenol blue) was loaded into each well of the gel and incubated 30 minutes without applying a voltage and without buffer recirculation. The TESSB buffer was blown out of each well with a pipet and 8 μL fresh TESSB buffer was added to each well. Eight microliters of the cell suspension in TESL buffer was loaded into each well such that the cells gently came into contact with the previously loaded TESSB buffer. The gel was exposed to field inversion electrophoresis in 0.5×TBE for five hours with the following parameters: refrigeration 14° C.; initial buffer circulation speed 100 mL/min. for 20 min. then 1,300 mL/min. for remainder of electrophoresis; program setting 1800 field inversion; forward voltage gradient at 8.0 V/cm; initial forward switch time is 1.6 seconds; final forward switch time is 2.4 seconds; reverse voltage at 8 V/cm; initial reverse switch time is 0.4 seconds; and final reverse switch time is 0.6 seconds. The gel was stained after electrophoresis for 30 min. with gentle shaking in 100 mL 0.5×TBE, 1× GelStar® staining solution (Cambrex Bio Sciences). The gel was rinsed 5 min. with deionized water and was placed on a low intensity UV transilluminator. Gel pieces containing plasmid bands were excised with a scalpel. Each gel piece was placed inside a separate 6000-8000 molecular weight cutoff dialysis membrane tube, 0.5×TBE buffer was added to cover the each piece, and each membrane was sealed with plastic clips. Each membrane was submerged in 0.5×TBE buffer in an electrophoresis apparatus. A current of 2.2 V/cm was applied for 3.5 hours. The buffer was removed from each dialysis membrane and transferred to a centrifuge tube. One-tenth volume 3 M sodium acetate pH 5.4 and one volume isopropanol were added, mixed chilled on ice for several minutes, and then centrifuged at 13,000×g for 30 minutes. The supernatant was carefully decanted from each tube leaving behind a small plasmid pellet. Three milliliters of 70% v/v ethanol were added to each tube and centrifuged a 13,000×g for 5 minutes. The 70% ethanol was carefully decanted from each tube and each small plasmid pellet was allowed to stand inverted for 10 minutes. Each plasmid pellet was resuspended into 50 μL 10 mM Tris-HCl pH 8 buffer and stored at 4 C.

An alternative method that also provided satisfactory results employed standard electrophoresis conditions and a 0.6% agarose gel prepared in 1×TBE (1×TBE=89 mM Tris toborate, pH approx. 8.3, 2 mM EDTA) buffer. *B. thuringiensis* cultures were inoculated into 2 mL Terrific broth (Sigma) in 12 mL culture tubes and incubated at 30° C. with shaking (250 rpm) for 20 hours. Using a Bio-Rad Protean II® gel electrophoresis apparatus or similar device, a 0.6% agarose gel with the dimensions 16×20×0.3 cm (or approximate equivalent size) was prepared in 1×TBE and cast using a comb with five teeth of 2.4 cm×0.3 cm dimensions. Using 1×TBE as the running buffer, the agarose gel was pre-run at 110V for 10 min. Two-hundred fifty microliters of TSB (5% sucrose/1×TBE/2% SDS/0.05% bromophenol blue) were added to each well and allowed to sit at room temperature for approximately 20 min. The TSB was blown out of the wells with a pipet to eliminate all gel fragments from the wells. Another 250 μL TSB were added to each well and allowed to stand for an additional 20 min. Concurrently, 1 mL aliquots of the overnight *B. thuringiensis* cultures were centrifuged in a microtube for 1 min., the supernatants discarded, and the cell pellets resuspended in 400 μL TSL (20% sucrose, 20 mM Tris pH 8, 1 mM EDTA, 2 mg/mL lysozyme, 10 ug/mL RNAse A). The suspended cells were incubated at 37° C. for 60 minutes with occasional inversion to keep the cells in suspension. Following this incubation period, 150 μL of the cell suspensions were gently pipetted underneath the TSB solution in the gel wells. Gel electrophoresis was conducted at 25V/4 mA for 1 hour, followed by 60V/10 mA for 30 minutes, followed by 110V/22 mA for 5.5 hours. The agarose gel was immersed for 30 minutes with gentle rocking in 150 mL 1× GelStar® in 1×TBE, then rinsed in water. The plasmid bands were visualized in a darkroom using a low-intensity UV transilluminator and excised from the gel. Gel slices were stored separately in 12 mL tubes at −20° C. Plasmid DNAs were purified from the gel slices using a Qiaex II purification kit and protocol described by the manufacturer (Qiagen, Valencia, Calif.).

Example 2

This example illustrates the preparation of libraries from the mega dalton sized plasmids purified from *B. thuringiensis* strains.

Libraries were constructed from the purified *B. thuringiensis* plasmid DNA using a procedure that incorporates random priming, PCR amplification and ligation independent cloning. The purified plasmid DNA was heat denatured and annealed to a redundant oligonucleotide primer composition in which each primer consisted of a uridine-rich cohesive 5' terminal sequence followed by nine random nucleotides at the 3' end. Random primers anneal to the plasmid DNA and are extended using Klenow enzyme. A 20 μL reaction was set up with 6 ng of various plasmid DNA isolated from strain EG5858 containing 2 μL of Klenow 10× buffer, 1 mM dNTPs, 50 ng primer and deionized water to a final volume of 19 μL. The reaction mix was heated to 93° C. for 3 minutes and immediately chilled on ice for 2 minutes. Five units (1 μL) of Klenow enzyme were added to the reaction on ice and then incubated in a thermal cycler for 25 minutes at 25° C., 30 minutes at 37° C. and 5 minutes at 50° C. The reaction was then heated to 93° C. for 3 minutes and placed on ice for 2 minutes. An additional 0.5 μL of Klenow 10× buffer, 3.5 μL of deionized water and 1 μL (5 units) of Klenow enzyme was added to the reaction on ice. The reaction was again incubated in a thermal cycler for 25 minutes at 25° C., 30 minutes at 37° C. and 5 minutes at 50° C. A population of amplicons were produced using this method which contain cohesive termini at both ends. The products of the reaction were purified using a QIAquick® PCR Purification Kit (Qiagen) following the manufacturer's protocol and eluted with 50 μL of 10 mM Tris-HCl, pH 8.5.

The amplicons produced using the method above were then amplified further in a 100 μL thermal amplification reaction volume containing, 10 μL of 10×PCR buffer, 2 mM $MgCl_2$, 0.5M Betaine, 1 uM PCR primer, 0.2 mM dNTPs, 10 μL of the eluted DNA template and 5 units of Taq Polymerase Enzyme. The reaction was incubated in a thermal cycler for 3 minutes at 94° C., followed by 10 cycles of 94° C. for 1 minutes, 50° C. for 1 minutes and 72° C. for 3 minutes. An additional 20 cycles were performed at 94° C. for 1 minutes, 45° C. for 1 minutes and 72° C. for 3 minutes. A final incubation at 72° C. for 10 minutes completed the amplification process. A total of about 380 ng of product was obtained from this reaction.

Plasmid libraries were produced using pUC19. The plasmid vector was linearized with BglII restriction endonucleases and dephosphorylated. A phosphorylated nucleotide primer as set forth in SEQ ID NO:21 was used as a ligation primer and mixed with the linearized plasmid, partially overlapping with the dephosphorylated BglII overhanging ends. The plasmid and primer were mixed together and ligated overnight at 16° C. in the presence of 2.5% PEG 8000, the then gel purified after extraction with an equal volume of phenol:chloroform:isoamyl alcohol (25:24:1).

Plasmid libraries were prepared in a 15 μL reaction containing 1.5 μL of 10× Uracil-DNA Glycosylase (UDG) buffer, 22.8 ng of amplification product, 56 ng of the adapter ligated vector and 2 units of UDG (New England Biolabs). The reaction was incubated for 3 hours at 37° C. The reaction was then precipitated and resuspended in 5 μL of 1×UDG buffer. DH10B electrocompetent cells (Invitrogen) were transformed with 1 μL of the resuspended reaction. A titer of 100,000 colony-forming units (CFU) was obtained from this transformation. DNA sequencing of the positive clones was performed on an Applied Biosystems 3730xl DNA Analyzer, using Big Dye® Terminator v3.0. Base-calling of sequencing traces was accomplished using Phred (0.000925.c), assembled with Phrap (0.990319) and edited in Consed (13.0, 030425).

Amino acid sequences deduced from open reading frames present in the nucleotide sequences obtained from the plasmid inserts were compared to amino acid sequences in the non-redundant protein database ("NRAA") using the program BLASTX (Gish and States, Nat. Genet. 3(3):266-272, 1993). Numerous partial open reading frames were identified in the nucleotide sequences within the inserted DNA in the plasmid library. Deduced amino acid sequences exhibited similarity to proteins previously observed to be expressed only from genes present in gram-negative entomopathogenic bacteria such as *Photorhabdus* species, *Xenorhabdus species, Serratia* entomophila, and in *Yersinia pestis*. The top BLASTX hits from these comparisons were to *Photorhabdus* species proteins such as TcaA, TcaB, TcaC, and TccC as well as homologs of these proteins previously identified in *Serratia, Xenorhabdus*, and *Yersinia* species. However, none of the deduced amino acid sequences exhibiting similarity to these Tc protein homologs exhibited an amino acid sequence similarity greater than 50% to any of the previously known Tc proteins, suggesting that these Bt amino acid sequences are at best only distantly related.

Example 3

This example illustrates the identification of insecticidal protein coding sequences from the plasmid sequences cloned in Example 2.

The complete open reading frames encoding the homologous sequences for each of the proteins identified in Example 2 were obtained using thermal amplification procedures, essentially walking out from the sequences first identified in Example 2. Nucleotide sequences as set forth in SEQ ID NO:1 from EG5858 were identified as open reading frames encoding the proteins designated herein as TIC813, TIC814, TIC816, TIC817, and TIC818 respectively. The deduced amino acid sequences from each of these nucleotide sequences is set forth respectively at SEQ ID NO:2, SEQ ID NO:3, SEQ ID NO:4, SEQ ID NO:5, and SEQ ID NO:6. TIC813 exhibited about 39% amino acid sequence identity to *Photorhabdus* species TcaA protein (GenBank Accession No. AAC38623), TIC814 exhibited about 49% amino acid sequence identity to *Photorhabdus* species TcaB protein (GenBank Accession No. AAC38624), TIC816 exhibited about 43% amino acid sequence identity to *Photorhabdus* species TcaC protein (GenBank Accession No. AAC38625), TIC817 exhibited about 34% amino acid sequence identity to *Photorhabdus* species TccC protein (GenBank Accession No. AAC38630), and TIC818 exhibited about 43% amino acid sequence identity also to *Photorhabdus* species TccC protein (GenBank Accession No. AAC38630).

As a consequence of the thermal amplification methods used to identify the complete open reading frame for each of the TC protein homologs, sequence analysis of the aligned amplicon sequences revealed a large gene cluster form which all five of the TIC proteins are apparently expressed in a single polycistronic operon. Surprisingly, the arrangement of the coding sequences within this operon is substantially similar to the arrangement of the genes encoding the *Photorhabdus* species TC proteins. The 5' region of the tcaA-like gene and the 3' end of the tccC-like gene, defining the 5' and 3' ends of the gene cluster, respectively, were amplified and cloned using an inverse PCR strategy. Briefly, EG5858 genomic DNA (0.1 μg/μL) was digested with the restriction endonuclease EcoRI at 37° C. for 2 hours and then incubated at 70° C. for 20 min. to inactivate the restriction enzyme. The restricted DNA fragments were diluted to 0.01 μg/μL and ligated together with T4 ligase at 4° C. overnight. The ligation products served as the template for a PCR using the Elongase kit and protocols provided by Invitrogen. Each PCR included 100 ng template DNA and employed the following cycling parameters for 35 cycles: 94° C., 2 min.; 92° C., 10 sec.; 50° C., 30 sec.; and 68° C., 15 min. The amplified DNA fragments were cloned into the TOPO-TA vector pCR2.1 (Invitrogen) and sequenced to obtain the remainder of the tcaA-like coding region.

A similar inverse PCR reaction was used to amplify and clone a ~8 kb HindIII fragment that includes the 3' end of the EG5858 tccC-like gene. In this instance, the EG5858 DNA was digested with HindIII rather than EcoRI. The amplified DNA fragments were cloned into the TOPO-TA vector pCR2.1 (Invitrogen) and sequenced to obtain the remaining 3' sequence of the tccC-like gene. The derived sequences were assembled with the existing sequences to generate a contiguous nucleotide sequence comprising a cluster of five genes, encoding from 5' to 3', proteins with sequence similarity to the TcaA-, TcaB-, TcaC-, TccC-like genes of *Photorhabdus luminescens*. These genes have been designated herein as tic813, tic814, tic816, tic817 and tic818 and proteins encoded by these genes have been designated as TIC813, TIC814, TIC816, TIC817 and TIC818, respectively. The relationship of these genes isolated from the EG5858 is illustrated in FIG. 1. The complete polynucleotide sequence of the gene cluster is set forth in SEQ ID NO:1.

A related gene was identified and isolated from *B. thuringiensis* strain EG4332 using the methods similar to those developed for EG5858. The related gene was determined to exhibit similarity to *P. luminescens* tcaB and was designated as tic815. The amino acid sequence deduced from the tic815 ORF was designated as TIC815.

Example 4

This example illustrates the identification of insecticidal coding sequences from EG4096.

*B. thuringiensis* strain EG4096 contained two large plasmids of ~60- and ~150 kb, each of which contained a copy of a gene encoding ET29 (Cyt2Ca1) (WO 97/17507). DNA from these two toxin plasmids were isolated using procedures described in Example 1 and used to construct libraries as described in Example 2. The nucleotide sequences obtained from the plasmid sequence analysis were used to search the NRAA database using the program BLASTX. Numerous plasmid sequences were identified that encoded protein sequences displaying amino acid sequence identity to insecticidal proteins from gram-negative bacteria such as *Photorhabdus luminescens, Xenorhabdus nematophila, Serratia entomophila*, and *Yersinia pestis*. The top BLASTX hits from these searches included the tcaA, tcaB, tcaC, and tccC proteins from *Photorhabdus luminescens* as well as homologs of these proteins found in *Xenorhabdus, Serratia*, and *Yersinia* species.

Assembly of the EG4096 nucleotide sequences yielded incomplete coding regions. Nucleotide sequences corresponding to the 5' and 3' ends of the ORF'S exhibiting a relationship to tcaA, tcaB, and tcaC genes were identified using TFASTA alignments to the *Photorhabdus* homologs. Based on this sequence data, oligonucleotide primers were designed to amplify and clone the complete coding regions for the as well as flanking nucleotide sequences for these partial ORF's using an inverse PCR cloning strategy. In this manner, the order of the genes within an operon could be deduced as well.

Primers were used to amplify and clone the tcaA homologous gene into the directional expression vector pET101/D-TOPO® expression vector (Invitrogen). The 5' "cacc" sequence of pr380 was provided for base-pairing with and directional cloning into the pET101/D-TOPO® vector. The tcaA homologous gene is designated as tic904 and the protein encoded the ORF as TIC904.

Primers were used to amplify and clone the tcaB homologous gene into the directional expression vector pET101/D-TOPO® expression vector (Invitrogen). The 5' "cacc" sequence of pr842 was provided for base-pairing with and directional cloning into the pET101/D-TOPO® vector. The tcaB homologous gene was designated as tic905 and the protein encoded by the ORF as TIC905.

Primers were used to amplify and clone the tcaC homologous gene into the directional expression vector pET101/D-TOPO® expression vector (Invitrogen). The 5' cacc sequence of pr854 provides for base-pairing with and directional cloning into the pET101/D-TOPO® vector. The tcaC homologous gene was designated as tic906 and the protein encoded by the ORF as TIC906.

The nucleotide sequences for the tic904 (SEQ ID NO:10), tic905 (SEQ ID NO:12), and tic906 (SEQ ID NO:14) genes were determined by sequencing multiple clones. The TIC904, TIC905, and TIC906 coding sequences were organized in an operon or gene cluster with the gene order being 5' tic904-tic905-tic906 3'. The protein sequences were each compared to their corresponding *Photorhabdus* homolog and the percentage amino acid sequence identities determined. The EG4096 proteins shared only 39-50% amino acid sequence identity with the *Photorhabdus tca* homologous proteins. Pairwise sequence comparisons between the EG5858 and EG4332 related insecticidal proteins showed substantial sequence identity. For example, the amino acid sequence of TIC814 isolated from EG5858 is identical to that of TIC815 isolated from EG4332. Pairwise sequence comparisons between the EG4096 and EG5858 proteins demonstrated significant sequence diversity. TIC813 appeared to be most closely related to TIC904 yet these only exhibited about 61% amino acid sequence identity. TIC814 appeared to be most closely related to TIC905 yet these exhibited only about 63 amino acid sequence identity. Discounting the identity between TIC814 and TIC815, the strongest identity existed between TIC816 and TIC906 in which these exhibited only about 68% amino acid sequence identity.

Example 5

This example illustrates the identification, cloning and expression of TIC912 from EG4096, a protein that exhibits similarity to a TccC3 protein expressed in *Photorhabdus luminescens*.

Overlapping DNA sequences from the large plasmid of *B. thuringiensis* strain EG4096 revealed an open reading frame, designated tic912 (SEQ ID NO:16), whose deduced amino acid sequence (TIC912 as set forth at SEQ ID NO:17) exhibited about 43% identity to a *Photorhabdus luminescens* insecticidal protein TccC3. Two DNA primers corresponding to the 5' and 3' ends of the tic912 coding sequence were used to PCR amplify the tic912 ORF from EG4096 total genomic DNA. The amplicon was cloned into the expression vector pET101/D-TOPO (Invitrogen) yielding plasmids pMON74072 and pMON74100. pMON74072 contains the unaltered tic912 gene. pMON74100 contains the tic912 gene with a 6×HIS (six histidine residues) coding sequence linked in frame to the 3' end of tic912 coding sequence, which when expressed in *E. coli*, would produce a fusion protein consisting of TIC912-$HIS_6$. An advantage of expression of TIC912-$HIS_6$ in pMON74100 is that soluble TIC912-$HIS_6$ protein may be produced and purified over a nickel column. *E. coli* cells harboring pMON74100 produced TIC912-$HIS_6$ in inclusion bodies but did not produce TIC912-$HIS_6$ in a soluble form. The TIC912-$HIS_6$ inclusion bodies have not been found to exhibit insecticidal activity.

Example 6

This example illustrates the expression of the insecticidal protein coding sequences described in Examples 1-4.

The expression of individual *B. thuringiensis* genes set forth herein may be accomplished by a variety of means known in the art. Using the nucleotide sequences determined for each gene, oligonucleotide primers may be designed that enable the amplification of these genes from *B. thuringiensis* genomic or plasmid DNA and the cloning of these genes into appropriate vectors for expression in *B. thuringiensis* (e.g. Baum et al., Appl. Environ. Microbiol. 56:3420-3428, 1990). High-fidelity thermostable polymerases may be used to reduce the frequency of errors generated during the amplification process. Appropriate restriction endonuclease sites may be incorporated at the ends of the amplified DNA to facilitate cloning into specialized vectors. The native promoters for the genes may be used to direct the transcription of these genes in *B. thuringiensis* or, alternatively, cry gene promoters may be used (Baum and Malvar, Mol. Microbiol. 18:1-12, 1995). Recombinant strains expressing these genes may be grown under a variety of different culture conditions to optimize the production of individual or multiple proteins. Insecticidal proteins of the present invention that form inclusion bodies within *B. thuringiensis* may be recovered and partially purified by discontinuous sucrose gradient centrifugation. Recombinant proteins bearing a C-terminal HIS-tag fusion may be purified using a nickel-charged resin.

The *B. thuringiensis* proteins of the present invention were expressed in heterologous hosts such as *E. coli*. pET Directional TOPO® vectors (Invitrogen) such as pET100/D-TOPO®, pET101/D-TOPO®, and pET102/D-TOPO® were used for convenient cloning and expression in *E. coli*. Protein bands corresponding to the TIC904, TIC905, and TIC906 proteins could be visualized by Coomassie blue staining after resolution in an SDS gel.

Similar strategies can be employed to express the tic genes of the present invention in alternative expression vector systems such as the pBAD Directional TOPO® vectors that allow modulation of induction conditions (Invitrogen). Alternatively, the genes in *B. thuringiensis* may be disrupted using procedures that employ homologous recombination to generate deletions or insertions within the target gene as described in U.S. Pat. No. 5,759,538. *B. thuringiensis* strains containing knockouts of specific genes such as those of the present invention can then be assessed in insect bioassay to determine the contribution of specific genes towards insecticidal activity.

Example 7

Detection of sequences homologous to the sequences identified in Examples 1-5.

Oligonucleotide primers were designed for use in thermal amplification reactions to identify homologs of the genes of the present invention isolated from *B. thuringiensis* strains EG4096, EG4332, and EG5858. Full length nucleotide sequences for the *B. thuringiensis* genes were aligned with the full length nucleotide sequence of the most closely related gram negative species homolog using the multiple sequence alignment program ClustalW (Higgins et al. Nucleic Acids Res. 22:4673-4680, 1994). Regions of nucleotide sequence conservation were noted and used to design oligonucleotide primers for thermal amplification-based screening. Total DNA was isolated from *B. thuringiensis* strains and used as a template for thermal amplification reactions. Alternatively, *B. thuringiensis* strains may be grown under culture conditions that provide vegetative cells suitable for inclusion in a thermal amplification reaction as a source of DNA template. Vegetative *B. thuringiensis* cells can be lysed at 94° C., releasing total DNA that serves as a template for DNA amplification. The examples provided below illustrate how large numbers of *B. thuringiensis* strains may be screened in a thermal amplification reaction for homologs of *B. thuringiensis* genes of the present invention using oligonucleotide primers specific for the *B. thuringiensis* genes. Primers sufficient for such screening include nucleotide sequences of from about 15 to about 50 or more contiguous nucleotides selected from the group consisting of SEQ ID NO:1 within the coding region of any of the open reading frames encoding TIC813, TIC814, TIC816, TIC817, and TIC818; SEQ ID NO:8, SEQ ID NO:10, SEQ ID NO:12, and SEQ ID NO:14.

Example 8

This example illustrates evaluations of the insecticidal proteins of the present invention.

Recombinant strains producing the proteins of the present invention are grown under inducing conditions and protein production assessed by SDS polyacrylamide gel electrophoresis. Spent cultures of the recombinant strains may be used directly in insect bioassay or, alternatively, the expressed proteins may be purified or partially purified as desired. Mixtures of different protein preparations, whether purified or not, may then be tested in insect bioassay to identify the optimal protein composition for insecticidal activity. The proteins of the present invention, alone or in combination, may also be tested for insecticidal activity by microinjection into insect larvae, for instance, as described by Lee et al. (Biochem. Biophys. Res. Comm. 319:1110-1116, 2004).

Bioassays for coleopteran insect pests may be conducted as follows, using Southern corn rootworm (SCR, *Diabrotica undecimpunctata howardi*) and Western corn rootworm (WCR, *Diabrotica virgifera virgifera*) as examples. The bioassays may be performed via surface inoculation of an artificial diet (Marrone et al., J. Econ. Entomol. 78:290-293, 1985), but without formalin. Protein actives may be prepared in a diluent (an aqueous 0.005% Triton X-100® solution) and applied to the surface of the diet. After the diluent has dried, first instar larvae are placed on the diet and incubated at 28° C. Typically, thirty-two larvae are tested per concentration. Mortality is scored after 5-7 days using the diluent-only treatment as the untreated check.

Two different bioassays may be run with Western corn rootworm (WCR) larvae. For the first WCR bioassay protocol, 200 mL of WCR diet is prepared in a manner similar to that described by Pleau et al. (Entomol. Exp. Appl. 105:1-11, 2002). Dilutions of the test samples are prepared using water as a diluent and as an untreated control. Twenty-five microliters of the test sample are applied per well. Plates are allowed to dry before adding insect larvae. One WCR neonate larva is added per well with a fine paintbrush. Plates are sealed with mylar and ventilated using an insect pin. Twenty-four larvae are tested per concentration. The bioassay plates are incubated at a 27° C., 60% RH, in complete darkness for 5-7 days. The number of surviving larvae per concentration is recorded at the end of the experiment. The masses of the surviving larvae are recorded on a suitable microbalance (Cahn C-33). Data are analyzed using JMP® 4 statistical software (SAS Institute, Cary, N.C., USA). Levene's test for homogeneity of variances is conducted on each data set and, where a significant lack of homogeneity is detected, masses are log transformed. General linear regressions are performed on the data sets to look for concentration-response effects. In an alternative WCR bioassay, protein actives are prepared in a diluent [10 mM Tris-HCl (pH 7.0), 0.1 mM EDTA, 0.005% Triton X-100®, 50 ug/mL rifamycin] and 20 uL applied to the surface of the WCR artificial diet (without formalin), dispensed in 200 uL aliquots in 96-well plates. After the diluent has dried, one neonate WCR larva is added per well with a fine paintbrush and the plates covered with a perforated mylar seal. Twenty-four larvae are tested per concentration. The bioassay plates are incubated at a 27° C., 60% RH, in complete darkness for 5-7 days. Mortality is scored and the masses of the surviving larvae recorded using a microbalance.

Procedures for conducting insect bioassays for lepidopteran insect pests are known in the art. Examples of lepidopteran bioassay protocols are described in Chambers et al. (J. Bacteriol. 173:3966-3976, 1991) and Von Tersch et al. (Appl. Environ. Microbiol. 57:349-358, 1991) and in U.S. Pat. No. 5,942,658.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations may be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. An isolated nucleotide sequence encoding a *Bacillus thuringiensis* strain EG5858 protein, wherein said protein is selected from the group consisting of SEQ ID NO:2, SEQ ID NO:3, SEQ ID NO:4, SEQ ID NO:5, and SEQ ID NO:6.

2. A vector comprising an isolated nucleotide sequence encoding a *Bacillus thuringiensis* strain EG5858 protein, wherein said protein is selected from the group consisting of SEQ ID NO:2, SEQ ID NO:3, SEQ ID NO:4, SEQ ID NO:5, and SEQ ID NO:6.

3. A host cell transformed with a vector of claim 2, wherein said host cell is selected from the group consisting of a bacterial cell and a plant cell.

4. The host cell of claim 3 wherein said plant cell is a dicot plant cell or a monocot plant cell.

5. The host cell of claim 4 wherein said dicot plant cell is selected from the group consisting of a cotton plant cell, a canola plant cell, a soybean plant cell, an alfalfa plant cell, a tree plant cell, a grape plant cell, and a fruit plant cell, and wherein said monocot plant cell is selected from the group consisting of a corn plant cell, a rice plant cell, an oat plant cell, a wheat plant cell, a banana plant cell, and a grass plant cell.

6. A transgenic plant, said plant having been transformed with a nucleic acid sequence encoding a *Bacillus thuringiensis* strain EG5858 protein, said protein comprising an amino acid sequence selected from the group consisting of SEQ ID NO:2, SEQ ID NO:3, SEQ ID NO:4, SEQ ID NO:5, and SEQ ID NO:6.

7. A seed produced from the plant of claim 6, wherein said seed comprises said nucleic acid sequence.

8. A progeny plant produced from the seed of claim 7.

* * * * *

SEQUENCE LISTING

<160> NUMBER OF SEQ ID NOS: 17

<210> SEQ ID NO 1
<211> LENGTH: 20944
<212> TYPE: DNA
<213> ORGANISM: Bacillus thuringiensis EG5858
<220> FEATURE:
<221> NAME/KEY: CDS
<222> LOCATION: (1428)..(4691)
<223> OTHER INFORMATION: TIC813 ORF
<220> FEATURE:
<221> NAME/KEY: CDS
<222> LOCATION: (4722)..(8336)
<223> OTHER INFORMATION: TIC814 ORF
<220> FEATURE:
<221> NAME/KEY: CDS
<222> LOCATION: (8400)..(12773)
<223> OTHER INFORMATION: TIC816 ORF
<220> FEATURE:
<221> NAME/KEY: CDS
<222> LOCATION: (12981)..(15743)

-continued

```
<223> OTHER INFORMATION: TIC817 ORF
<220> FEATURE:
<221> NAME/KEY: CDS
<222> LOCATION: (15803)..(18583)
<223> OTHER INFORMATION: TIC818 ORF
<220> FEATURE:
<221> NAME/KEY: CDS
<222> LOCATION: (19886)..(20944)
<223> OTHER INFORMATION: TICXAX ORF

<400> SEQUENCE: 1

gaattcttat tagtaataca tgcaagttgt ttaagagata tttcttgata tatgcttttg     60

gaaatataat tctggcaagt aataatgggt ttcgaatgat ttttgcctct atgtgctttt    120

acatgttcag tgaaagtaca aaaagcttct tgtattaaat ccaatataga gttaatctta    180

tttaatttct caaggctctg tatgtataaa tctccaagag caaaagcaat ctcagaaggg    240

agacctccct ctattgcata tctagaagcg atagcaatgc cagtaattgc ttgatttttt    300

cgattgcgta attcactcgt taagcataat actccaacct tttcataggg aaatgccttc    360

aaatgtttta atacttcttc tagattccca gctttaattg cttcaaacat tttggttgaa    420

accgatacct cattacgtgc atgatcattt tgatgacaag ctgaaataaa taaacccgga    480

tttttttactt cacgggacat agtgttaaga aaattatttc ttttctcaac ggttttaacg    540

tctatttttt taaaataaat catgtaatac agtaaaatgc tgacatgaat tagatttgat    600

ttttttatga ctggtattga atgataataa ttcataactt tatgtttatt tgctataaca    660

tgacaatcat ttatgatcct atttatcatt ttttctaacg gttttgagaa tatacagggt    720

ccaatgataa aagctccttc agtgttctcc tggatattta agtgtattaa gatgaaactt    780

tcaagaaaat tatttgttcg aataattgga aagttaaaag gatcatcatc catataaagt    840

tcatttagat gttctacttt agaggaataa aaggggttag ggatatcact agatacattt    900

tcatgaagga tctttttgtt cttatcacaa aaacgaacag gtatctcaaa tgtttgaaat    960

agcaactgac aaatgtattc tttatttact gagtgatctg ctttattcat agtatgcacc   1020

tcttataatc ataatgactt ttagaattgt gtataaaata caatttacac aaggcttaat   1080

ggaactaact taatctcaca caattactaa attcaagtaa aaatagttat atttttctag   1140

taatcttatc aaataacaac tgaaatttca tgtaatatta gtaacgaaat catgtaataa   1200

tgcatattta gcgttacata tgctaattca tgtttatcta gtcaaaagaa ttgaataatt   1260

attttattag gagtgataaa tgtgaatggc attcaacaat atctaacttg atacatattt   1320

atttaaactt aattgataag aagaacatct gggatacacg cgacataata ttattaaatt   1380

ttaatatata atttaaaact taataaatac aaaaggagga atttatt gtg tca aca     1436
                                                    Val Ser Thr
                                                    1

aca gaa aat aac gta ggc ata ttc cag att gga acc gat aga tta aca     1484
Thr Glu Asn Asn Val Gly Ile Phe Gln Ile Gly Thr Asp Arg Leu Thr
    5                   10                  15

gta aca ctt aat caa tct ggc tat caa aca gta ttt gat att aca tcc     1532
Val Thr Leu Asn Gln Ser Gly Tyr Gln Thr Val Phe Asp Ile Thr Ser
20                  25                  30                  35

gaa agt tat ttg gag ttt gaa gaa aat aat cct gag att ccg tcc tca     1580
Glu Ser Tyr Leu Glu Phe Glu Glu Asn Asn Pro Glu Ile Pro Ser Ser
                40                  45                  50

gat gct aag gag att tat aaa tta gcc gtc aaa agg aca gaa aat tta     1628
Asp Ala Lys Glu Ile Tyr Lys Leu Ala Val Lys Arg Thr Glu Asn Leu
            55                  60                  65

aga atg ctc ttt aag gca tgg caa cta cac aat gat cca att ttc aaa     1676
```

-continued

```
Arg Met Leu Phe Lys Ala Trp Gln Leu His Asn Asp Pro Ile Phe Lys
        70                  75                  80

gat att cca aaa tta tcc tca aat att gga atg caa ggc atg cgc tct      1724
Asp Ile Pro Lys Leu Ser Ser Asn Ile Gly Met Gln Gly Met Arg Ser
    85                  90                  95

gcg tta aaa cgt agt ctt ggg gga gga gcc aat ttt gaa gat cta ttt      1772
Ala Leu Lys Arg Ser Leu Gly Gly Gly Ala Asn Phe Glu Asp Leu Phe
100                 105                 110                 115

cca gag cgt tct ctt gaa gga tat gca gaa tca tcc tcc ata cag tcg      1820
Pro Glu Arg Ser Leu Glu Gly Tyr Ala Glu Ser Ser Ser Ile Gln Ser
                120                 125                 130

ctt ttc tca cca ggt cgc tac tta act gta ttg tac aaa att gct cga      1868
Leu Phe Ser Pro Gly Arg Tyr Leu Thr Val Leu Tyr Lys Ile Ala Arg
            135                 140                 145

caa ctg cac agt aca gaa gac aaa tta cat att gac aat cgt cga cct      1916
Gln Leu His Ser Thr Glu Asp Lys Leu His Ile Asp Asn Arg Arg Pro
        150                 155                 160

gat ttg cag tca cta gta ctt tcc gaa gat aac atg aat aag gaa gta      1964
Asp Leu Gln Ser Leu Val Leu Ser Glu Asp Asn Met Asn Lys Glu Val
    165                 170                 175

tct tct ttg gat att ttg cta gat gtg tta caa ccc gaa gat ttc aat      2012
Ser Ser Leu Asp Ile Leu Leu Asp Val Leu Gln Pro Glu Asp Phe Asn
180                 185                 190                 195

aca tta aag act cta aaa gat aca tat tat cct atg aat ctt cct tac      2060
Thr Leu Lys Thr Leu Lys Asp Thr Tyr Tyr Pro Met Asn Leu Pro Tyr
                200                 205                 210

gat gat gat ctt act caa att aat gca gta gct gag gct cat tct acc      2108
Asp Asp Asp Leu Thr Gln Ile Asn Ala Val Ala Glu Ala His Ser Thr
            215                 220                 225

aat ttg ata ggg att tgg gat att ttg tta gac aaa cag caa aaa agt      2156
Asn Leu Ile Gly Ile Trp Asp Ile Leu Leu Asp Lys Gln Gln Lys Ser
        230                 235                 240

att ctg caa gac gtg aac act ttt cca cga ata agt aag aaa cgc aga      2204
Ile Leu Gln Asp Val Asn Thr Phe Pro Arg Ile Ser Lys Lys Arg Arg
    245                 250                 255

gat tca ctt tca aat acc cct gaa tcg ttg gaa tta ata gaa gga gaa      2252
Asp Ser Leu Ser Asn Thr Pro Glu Ser Leu Glu Leu Ile Glu Gly Glu
260                 265                 270                 275

gaa ttc tat ttg gag gct aaa ggc aag caa atc tat ttt gcg aat gta      2300
Glu Phe Tyr Leu Glu Ala Lys Gly Lys Gln Ile Tyr Phe Ala Asn Val
                280                 285                 290

atg gaa act gct tat acc ata agt act cac att acc gtt gga aag ccg      2348
Met Glu Thr Ala Tyr Thr Ile Ser Thr His Ile Thr Val Gly Lys Pro
            295                 300                 305

caa gct gct gca act gca cca gca aag ttt caa ttg att tac gat atc      2396
Gln Ala Ala Ala Thr Ala Pro Ala Lys Phe Gln Leu Ile Tyr Asp Ile
        310                 315                 320

aaa agg ggc gac tac ttc tta cgt gtt gca gaa aat att tca atc gat      2444
Lys Arg Gly Asp Tyr Phe Leu Arg Val Ala Glu Asn Ile Ser Ile Asp
    325                 330                 335

gga aaa tct ctg aag gat tgt tat cta acc agt gac aat gga gag cac      2492
Gly Lys Ser Leu Lys Asp Cys Tyr Leu Thr Ser Asp Asn Gly Glu His
340                 345                 350                 355

aat ggt aaa aaa gga ttt tat tgt cta atg aag aat ccc cgg aat aat      2540
Asn Gly Lys Lys Gly Phe Tyr Cys Leu Met Lys Asn Pro Arg Asn Asn
                360                 365                 370

ttt cct gta aaa att gag agg ttg aca gat aca tcc att cgt att ttc      2588
Phe Pro Val Lys Ile Glu Arg Leu Thr Asp Thr Ser Ile Arg Ile Phe
            375                 380                 385
```

-continued

```
gtt cca caa tct ggc tat tgg gga cca ggt gaa act gta gca agc cat      2636
Val Pro Gln Ser Gly Tyr Trp Gly Pro Gly Glu Thr Val Ala Ser His
        390                 395                 400

tgg gaa aat cct tta gcg ctt aat ctt gat tta gct gaa gct tta acc      2684
Trp Glu Asn Pro Leu Ala Leu Asn Leu Asp Leu Ala Glu Ala Leu Thr
    405                 410                 415

ttt act tta aaa aag aat gag act gga ggc gaa aca att tct gta tct      2732
Phe Thr Leu Lys Lys Asn Glu Thr Gly Gly Glu Thr Ile Ser Val Ser
420                 425                 430                 435

gag gtg atg ccg ccg gtg gcg gat act acc ccg tct ccg cca gca aga      2780
Glu Val Met Pro Pro Val Ala Asp Thr Thr Pro Ser Pro Pro Ala Arg
                440                 445                 450

gaa act ctt tct tta aca cct aac agt ttt cag cta cta gtc aat cct      2828
Glu Thr Leu Ser Leu Thr Pro Asn Ser Phe Gln Leu Leu Val Asn Pro
            455                 460                 465

aat cca aca gta gaa gat att gct aat cac tat gat gtt aag gct act      2876
Asn Pro Thr Val Glu Asp Ile Ala Asn His Tyr Asp Val Lys Ala Thr
        470                 475                 480

aag aat ctt gat tct acg gat ctg acc act gtt tta aac aat gtc gat      2924
Lys Asn Leu Asp Ser Thr Asp Leu Thr Thr Val Leu Asn Asn Val Asp
    485                 490                 495

aat ttt tgc ctg aaa aca agc ttg agt ttt aat aaa tta ttg gaa ctt      2972
Asn Phe Cys Leu Lys Thr Ser Leu Ser Phe Asn Lys Leu Leu Glu Leu
500                 505                 510                 515

acc atg cag aaa gat tat cag aca aaa agt ggt gag tat aaa agt cga      3020
Thr Met Gln Lys Asp Tyr Gln Thr Lys Ser Gly Glu Tyr Lys Ser Arg
                520                 525                 530

ttt tta aag ttt agt agt acg gaa aat gtt cca gtt tcc aca tat ggt      3068
Phe Leu Lys Phe Ser Ser Thr Glu Asn Val Pro Val Ser Thr Tyr Gly
            535                 540                 545

gct gct ttt ttg aca ggt aca gaa caa att cct tta tgg gtg aaa cag      3116
Ala Ala Phe Leu Thr Gly Thr Glu Gln Ile Pro Leu Trp Val Lys Gln
        550                 555                 560

tat aac ggc aaa ggt aat gca aca aat acc cca gtt tta aat ttt aca      3164
Tyr Asn Gly Lys Gly Asn Ala Thr Asn Thr Pro Val Leu Asn Phe Thr
    565                 570                 575

gca gat aat gtt gta gat tta gca gga aga gca gaa aaa ctt gtt aga      3212
Ala Asp Asn Val Val Asp Leu Ala Gly Arg Ala Glu Lys Leu Val Arg
580                 585                 590                 595

ttg gag cat agc aca gat ctt tca ttt gag cag tta gac tgg ata atc      3260
Leu Glu His Ser Thr Asp Leu Ser Phe Glu Gln Leu Asp Trp Ile Ile
                600                 605                 610

act aat gcc agc aaa tcc ata ttc gaa cac ggt aaa aat atc att ttg      3308
Thr Asn Ala Ser Lys Ser Ile Phe Glu His Gly Lys Asn Ile Ile Leu
            615                 620                 625

gat aaa cca gta ctt ggt gca ata gct gaa tat aaa aag ttc aat aat      3356
Asp Lys Pro Val Leu Gly Ala Ile Ala Glu Tyr Lys Lys Phe Asn Asn
        630                 635                 640

cac tat ggc atc aca tct gat atg ttc gtc aca ttt ata ggt gaa ata      3404
His Tyr Gly Ile Thr Ser Asp Met Phe Val Thr Phe Ile Gly Glu Ile
    645                 650                 655

aat aca tat gcg gaa gaa ggt aag aac agt ttt tat cag gat act ttc      3452
Asn Thr Tyr Ala Glu Glu Gly Lys Asn Ser Phe Tyr Gln Asp Thr Phe
660                 665                 670                 675

agt aat gtg gat ggt act aca gtt cct ttg ggg gca tct tta caa ttc      3500
Ser Asn Val Asp Gly Thr Thr Val Pro Leu Gly Ala Ser Leu Gln Phe
                680                 685                 690

gca att gat aaa caa ggg tta tat gaa tcc att tgc tgt ggg gca atg      3548
Ala Ile Asp Lys Gln Gly Leu Tyr Glu Ser Ile Cys Cys Gly Ala Met
            695                 700                 705
```

-continued

```
ggg gtt act gct gat gag ttt tct cgt att ggt gca tac tgt ttt ggt      3596
Gly Val Thr Ala Asp Glu Phe Ser Arg Ile Gly Ala Tyr Cys Phe Gly
        710                 715                 720

gat gca aca caa caa att act gct gat gaa gct tcc att gca caa ctc      3644
Asp Ala Thr Gln Gln Ile Thr Ala Asp Glu Ala Ser Ile Ala Gln Leu
    725                 730                 735

tat cgt cta ggt aaa atc cct cag atg ctg ggg tta agc ttt aga gaa      3692
Tyr Arg Leu Gly Lys Ile Pro Gln Met Leu Gly Leu Ser Phe Arg Glu
740                 745                 750                 755

gct gaa tta tta tgg aaa aca atg gcc agc ggt aaa aat act ttg ctt      3740
Ala Glu Leu Leu Trp Lys Thr Met Ala Ser Gly Lys Asn Thr Leu Leu
                760                 765                 770

cgt aac atc ggg gct agt cca cat agc tta caa act ttg gat att atc      3788
Arg Asn Ile Gly Ala Ser Pro His Ser Leu Gln Thr Leu Asp Ile Ile
            775                 780                 785

cgt cga act gaa gtc ctt tta gat tgg atg gat act cat cag ctt gat      3836
Arg Arg Thr Glu Val Leu Leu Asp Trp Met Asp Thr His Gln Leu Asp
        790                 795                 800

gtt gtc tcg cta caa gtc atg att act aat cag tac agt agt acg gct      3884
Val Val Ser Leu Gln Val Met Ile Thr Asn Gln Tyr Ser Ser Thr Ala
    805                 810                 815

aca ccg gag tta tac aat ttt ttg aaa aat gta tac caa tct aca att      3932
Thr Pro Glu Leu Tyr Asn Phe Leu Lys Asn Val Tyr Gln Ser Thr Ile
820                 825                 830                 835

agt gtc gag cgt act tct agg ata agt aat cac aaa agt atg cct gca      3980
Ser Val Glu Arg Thr Ser Arg Ile Ser Asn His Lys Ser Met Pro Ala
                840                 845                 850

gaa aaa atg tcc aga gca tta gca gca ggt ttc aat ctg aag gta aac      4028
Glu Lys Met Ser Arg Ala Leu Ala Ala Gly Phe Asn Leu Lys Val Asn
            855                 860                 865

gtg atg gga aaa gta atg aaa tgg atg gac aaa gct caa cca acg ttt      4076
Val Met Gly Lys Val Met Lys Trp Met Asp Lys Ala Gln Pro Thr Phe
        870                 875                 880

atg tcg caa gat ttc tat act aaa ctt cac tgg tat ttt agt aca gat      4124
Met Ser Gln Asp Phe Tyr Thr Lys Leu His Trp Tyr Phe Ser Thr Asp
    885                 890                 895

cat gaa gat gaa cta act acc tta gaa aag cat cct gaa ttg ttg gaa      4172
His Glu Asp Glu Leu Thr Thr Leu Glu Lys His Pro Glu Leu Leu Glu
900                 905                 910                 915

tgg tgc cag aaa gtc agt caa tat gtg ctc att gtt cgt tgg tct gga      4220
Trp Cys Gln Lys Val Ser Gln Tyr Val Leu Ile Val Arg Trp Ser Gly
                920                 925                 930

cta aac gag cag gag ttg aca atg atg att gaa cat cct gac tgg ctt      4268
Leu Asn Glu Gln Glu Leu Thr Met Met Ile Glu His Pro Asp Trp Leu
            935                 940                 945

tta gag gga tat gat acg gta cct caa cct tca tta cat ctt cta ttg      4316
Leu Glu Gly Tyr Asp Thr Val Pro Gln Pro Ser Leu His Leu Leu Leu
        950                 955                 960

ata cta tct cgc ttg aaa gag tgg gaa caa cgt gtt caa gtt tcc agt      4364
Ile Leu Ser Arg Leu Lys Glu Trp Glu Gln Arg Val Gln Val Ser Ser
    965                 970                 975

gat gag gca atc cgt tac ttt gct cag gct aat tcg aaa aat atc aat      4412
Asp Glu Ala Ile Arg Tyr Phe Ala Gln Ala Asn Ser Lys Asn Ile Asn
980                 985                 990                 995

tca gat gct gca gta  aag ctt ctt gct cat  atc cat ggt tgg aat        4457
Ser Asp Ala Ala Val  Lys Leu Leu Ala His  Ile His Gly Trp Asn
                1000                 1005                 1010

gaa gag ggg acg tct  tct atg aat aac tat  ctg ttt ggt gat gac        4502
Glu Glu Gly Thr Ser  Ser Met Asn Asn Tyr  Leu Phe Gly Asp Asp
```

-continued

```
                1015                1020                1025

tca tat cca aag aac  ttt gag cag gta ttt  aca tta gaa agc tgg      4547
Ser Tyr Pro Lys Asn  Phe Glu Gln Val Phe  Thr Leu Glu Ser Trp
                1030                1035                1040

gtc aac tta ggg aaa  cag cta aac gtt ggt  agt aga act cta gga      4592
Val Asn Leu Gly Lys  Gln Leu Asn Val Gly  Ser Arg Thr Leu Gly
                1045                1050                1055

gag cta gtt gat tta  gta gaa gaa aac gaa  act gca gaa agc act      4637
Glu Leu Val Asp Leu  Val Glu Glu Asn Glu  Thr Ala Glu Ser Thr
                1060                1065                1070

gat tta atc att tca  gta gca caa gcc ctg  atg gct aca gta caa      4682
Asp Leu Ile Ile Ser  Val Ala Gln Ala Leu  Met Ala Thr Val Gln
                1075                1080                1085

tct gaa aaa taatattagt aaagaaaggt ggtaaagagt atg tct  aat tca acc  4736
Ser Glu Lys                                 Met Ser  Asn Ser Thr
                                                1090

gta ttg  caa tct att aaa gaa  tcc cgt cgt gat gtg  ttg gtg gac      4781
Val Leu  Gln Ser Ile Lys Glu  Ser Arg Arg Asp Val  Leu Val Asp
    1095                1100                1105

cat tat  atc gcc aac aat gtt  ccc aaa gat cta aca  gat aag att      4826
His Tyr  Ile Ala Asn Asn Val  Pro Lys Asp Leu Thr  Asp Lys Ile
    1110                1115                1120

act gat  gcg gag agt ctt tat  gaa tat ttg tta cta  gat act aaa      4871
Thr Asp  Ala Glu Ser Leu Tyr  Glu Tyr Leu Leu Leu  Asp Thr Lys
    1125                1130                1135

ata agt  gat ctt gtc aaa aca  tct ccg ata gca gag  gct att agt      4916
Ile Ser  Asp Leu Val Lys Thr  Ser Pro Ile Ala Glu  Ala Ile Ser
    1140                1145                1150

agc gta  cag tta tat ata aat  cgc tgt ata caa ggc  tat gaa ggg      4961
Ser Val  Gln Leu Tyr Ile Asn  Arg Cys Ile Gln Gly  Tyr Glu Gly
    1155                1160                1165

gag tta  acc acg caa agt aaa  agt cat ttt gca cca  gga aag ttc      5006
Glu Leu  Thr Thr Gln Ser Lys  Ser His Phe Ala Pro  Gly Lys Phe
    1170                1175                1180

tta tcc  aat tgg gac aat tat  aac aag cgc tat acc  act tgg tca      5051
Leu Ser  Asn Trp Asp Asn Tyr  Asn Lys Arg Tyr Thr  Thr Trp Ser
    1185                1190                1195

ggt aaa  gaa cgt cta aaa tat  tat gca ggc agc tac  att gat cca      5096
Gly Lys  Glu Arg Leu Lys Tyr  Tyr Ala Gly Ser Tyr  Ile Asp Pro
    1200                1205                1210

tca tca  cgt tac aat aaa aca  aac tta ttc aaa aat  tta gaa cag      5141
Ser Ser  Arg Tyr Asn Lys Thr  Asn Leu Phe Lys Asn  Leu Glu Gln
    1215                1220                1225

agt ata  agt caa ggg aga ctt  acc gaa gaa agt atc  aaa aat gca      5186
Ser Ile  Ser Gln Gly Arg Leu  Thr Glu Glu Ser Ile  Lys Asn Ala
    1230                1235                1240

cta cac  aac tat ttg gac gaa  tat gaa act tta gca  aat ttg gaa      5231
Leu His  Asn Tyr Leu Asp Glu  Tyr Glu Thr Leu Ala  Asn Leu Glu
    1245                1250                1255

tat ata  agc gta aat aaa ggt  gat ggt gag gat gct  gaa agt gta      5276
Tyr Ile  Ser Val Asn Lys Gly  Asp Gly Glu Asp Ala  Glu Ser Val
    1260                1265                1270

ttg ttc  ttt gtt ggt cga act  caa aca ttt ccc tat  gaa tat tac      5321
Leu Phe  Phe Val Gly Arg Thr  Gln Thr Phe Pro Tyr  Glu Tyr Tyr
    1275                1280                1285

tgg cga  agc ttg atc cta aaa  aag aac agt aac aat  ata ctg att      5366
Trp Arg  Ser Leu Ile Leu Lys  Lys Asn Ser Asn Asn  Ile Leu Ile
    1290                1295                1300

cca gaa  aaa tgg act cag tgg  gaa aaa atc act gcg  aat atc ggc      5411
```

-continued

```
Pro Glu  Lys Trp Thr Gln Trp  Glu Lys Ile Thr Ala  Asn Ile Gly
    1305                 1310                 1315

gaa gca  gtt gac agc tac gta  gta att tac tgt tat  aaa aaa cgc      5456
Glu Ala  Val Asp Ser Tyr Val  Val Ile Tyr Cys Tyr  Lys Lys Arg
    1320                 1325                 1330

ttg cat  gtg cag tgg tct tct  tca gag aaa aaa caa  aat att aac      5501
Leu His  Val Gln Trp Ser Ser  Ser Glu Lys Lys Gln  Asn Ile Asn
    1335                 1340                 1345

aaa gaa  tct att gat ata cag  tat cta aat gat tgg  gtc atg aat      5546
Lys Glu  Ser Ile Asp Ile Gln  Tyr Leu Asn Asp Trp  Val Met Asn
    1350                 1355                 1360

agt tct  gga gtg tgg tct gcc  ttc cag aag tca cct  ttc aaa agt      5591
Ser Ser  Gly Val Trp Ser Ala  Phe Gln Lys Ser Pro  Phe Lys Ser
    1365                 1370                 1375

ttt gat  tac atc cct aat tca  ata acc ggt ttt tct  aaa gaa aat      5636
Phe Asp  Tyr Ile Pro Asn Ser  Ile Thr Gly Phe Ser  Lys Glu Asn
    1380                 1385                 1390

atc cat  att gtt gat aat aaa  gta atc tgt gat gat  cca aac agt      5681
Ile His  Ile Val Asp Asn Lys  Val Ile Cys Asp Asp  Pro Asn Ser
    1395                 1400                 1405

att aaa  gta aag gtg act tca  tta cca ggt aat aga  gta cgt att      5726
Ile Lys  Val Lys Val Thr Ser  Leu Pro Gly Asn Arg  Val Arg Ile
    1410                 1415                 1420

tat ttc  gaa aag att tac aat  agc gaa tta tca ggt  tct act ctc      5771
Tyr Phe  Glu Lys Ile Tyr Asn  Ser Glu Leu Ser Gly  Ser Thr Leu
    1425                 1430                 1435

tct ttt  tgg ccc gct cta tct  tca gac cca gaa att  aat gag ggg      5816
Ser Phe  Trp Pro Ala Leu Ser  Ser Asp Pro Glu Ile  Asn Glu Gly
    1440                 1445                 1450

gaa caa  aaa gat tat att ata  gat ttt gat agt gaa  cct tat tat      5861
Glu Gln  Lys Asp Tyr Ile Ile  Asp Phe Asp Ser Glu  Pro Tyr Tyr
    1455                 1460                 1465

ggg tta  ctg gtg agg tta aat  ttc gat caa aaa gag  tat tat ttc      5906
Gly Leu  Leu Val Arg Leu Asn  Phe Asp Gln Lys Glu  Tyr Tyr Phe
    1470                 1475                 1480

agt gtt  ttg tat tac cca agt  cct tat caa gaa tta  tat ggg tca      5951
Ser Val  Leu Tyr Tyr Pro Ser  Pro Tyr Gln Glu Leu  Tyr Gly Ser
    1485                 1490                 1495

att atc  aat gat caa ttt att  ccc cca tca aat agt  aaa ata ata      5996
Ile Ile  Asn Asp Gln Phe Ile  Pro Pro Ser Asn Ser  Lys Ile Ile
    1500                 1505                 1510

gaa cct  ata agt ctt act ctt  aaa aat aat att gat  tta gct aac      6041
Glu Pro  Ile Ser Leu Thr Leu  Lys Asn Asn Ile Asp  Leu Ala Asn
    1515                 1520                 1525

tta tgt  gaa aat agc att gat  aca ttg ttt gaa tat  aca gtt cag      6086
Leu Cys  Glu Asn Ser Ile Asp  Thr Leu Phe Glu Tyr  Thr Val Gln
    1530                 1535                 1540

ggg gag  ttg ggg gac acc att  gct ttt tat gga cct  tac gga att      6131
Gly Glu  Leu Gly Asp Thr Ile  Ala Phe Tyr Gly Pro  Tyr Gly Ile
    1545                 1550                 1555

tat tta  tgg gaa att ttt ttc  tat ata cct ttt tta  ata gct gtg      6176
Tyr Leu  Trp Glu Ile Phe Phe  Tyr Ile Pro Phe Leu  Ile Ala Val
    1560                 1565                 1570

agg ctt  cta ata gaa caa cga  tac gaa ctg gtg gaa  cgt tgg tac      6221
Arg Leu  Leu Ile Glu Gln Arg  Tyr Glu Leu Val Glu  Arg Trp Tyr
    1575                 1580                 1585

aaa ttt  ata ttt aac agc gct  ggc tac cgt gac gaa  aat ggt aat      6266
Lys Phe  Ile Phe Asn Ser Ala  Gly Tyr Arg Asp Glu  Asn Gly Asn
    1590                 1595                 1600
```

-continued

```
ttg ttg  aaa gat aaa aat gga  aat gta cgt tat tgg  aat gta gta      6311
Leu Leu  Lys Asp Lys Asn Gly  Asn Val Arg Tyr Trp  Asn Val Val
    1605                 1610                 1615

ccg tta  caa gaa gat act gag  tgg gat gaa aca ttg  tct ctt gca      6356
Pro Leu  Gln Glu Asp Thr Glu  Trp Asp Glu Thr Leu  Ser Leu Ala
    1620                 1625                 1630

atc act  gat cca gat gaa ata  gct atg gcc gac cca  atg caa tac      6401
Ile Thr  Asp Pro Asp Glu Ile  Ala Met Ala Asp Pro  Met Gln Tyr
    1635                 1640                 1645

aaa ctg  gct ata ttc att cat  act tta gat ttt ctc  atc aat cgc      6446
Lys Leu  Ala Ile Phe Ile His  Thr Leu Asp Phe Leu  Ile Asn Arg
    1650                 1655                 1660

gga gat  cat gcc tat aga atg  tta gaa cgt gat act  ctt act gag      6491
Gly Asp  His Ala Tyr Arg Met  Leu Glu Arg Asp Thr  Leu Thr Glu
    1665                 1670                 1675

gct aag  atg tat tat ata cag  gct aaa caa ata ttg  ggg ccc cga      6536
Ala Lys  Met Tyr Tyr Ile Gln  Ala Lys Gln Ile Leu  Gly Pro Arg
    1680                 1685                 1690

cct gaa  att cgt att aat aat  agt tgg gat aat ccg  acc ttg caa      6581
Pro Glu  Ile Arg Ile Asn Asn  Ser Trp Asp Asn Pro  Thr Leu Gln
    1695                 1700                 1705

agc gaa  gca ggt gct atg act  gct gaa cca aca aga  aat aat ttg      6626
Ser Glu  Ala Gly Ala Met Thr  Ala Glu Pro Thr Arg  Asn Asn Leu
    1710                 1715                 1720

gac ata  aca cca atc atg caa  tta caa gca ttt ctg  aaa tct gaa      6671
Asp Ile  Thr Pro Ile Met Gln  Leu Gln Ala Phe Leu  Lys Ser Glu
    1725                 1730                 1735

aat gga  cat ttt tta tct cca  tat aat gat gag ctg  tta gct ttc      6716
Asn Gly  His Phe Leu Ser Pro  Tyr Asn Asp Glu Leu  Leu Ala Phe
    1740                 1745                 1750

tgg gat  aaa atc gaa cta cgt  tta tac aac tta cgt  cac aat ctg      6761
Trp Asp  Lys Ile Glu Leu Arg  Leu Tyr Asn Leu Arg  His Asn Leu
    1755                 1760                 1765

agt tta  gat gga caa cct ctt  aat tta ccg cta ttt  gtt gaa ccg      6806
Ser Leu  Asp Gly Gln Pro Leu  Asn Leu Pro Leu Phe  Val Glu Pro
    1770                 1775                 1780

atg aac  ccg cgt gat ttg cag  att cag tat agt aca  gga gat ggc      6851
Met Asn  Pro Arg Asp Leu Gln  Ile Gln Tyr Ser Thr  Gly Asp Gly
    1785                 1790                 1795

atg ggg  ggg agt gta gct tct  tct caa agt tca cag  agt atc tat      6896
Met Gly  Gly Ser Val Ala Ser  Ser Gln Ser Ser Gln  Ser Ile Tyr
    1800                 1805                 1810

cgt ttc  cct att gta att gat  aaa gca cgt act gca  gtt aat agc      6941
Arg Phe  Pro Ile Val Ile Asp  Lys Ala Arg Thr Ala  Val Asn Ser
    1815                 1820                 1825

gtg atc  caa ttt gga agt gcc  tta gaa aat gca ttc  gca aaa caa      6986
Val Ile  Gln Phe Gly Ser Ala  Leu Glu Asn Ala Phe  Ala Lys Gln
    1830                 1835                 1840

gat acc  gag gcg atg aca tta  tta tta caa tct cag  cag caa gtt      7031
Asp Thr  Glu Ala Met Thr Leu  Leu Leu Gln Ser Gln  Gln Gln Val
    1845                 1850                 1855

att cta  cag caa act cgt gat  atg cag gaa aag aac  cta gat tcg      7076
Ile Leu  Gln Gln Thr Arg Asp  Met Gln Glu Lys Asn  Leu Asp Ser
    1860                 1865                 1870

ttg caa  gca agt ctt gaa gct  aca acg ata gca aaa  gca agt gcc      7121
Leu Gln  Ala Ser Leu Glu Ala  Thr Thr Ile Ala Lys  Ala Ser Ala
    1875                 1880                 1885

gaa tca  act aag aca cat tat  gct ggt tta gtg gaa  aac tgg atg      7166
Glu Ser  Thr Lys Thr His Tyr  Ala Gly Leu Val Glu  Asn Trp Met
    1890                 1895                 1900
```

```
tca gat  aat gaa act agc tca  cta aaa tta cgt tca  gat gct gga      7211
Ser Asp  Asn Glu Thr Ser Ser  Leu Lys Leu Arg Ser  Asp Ala Gly
    1905                 1910                 1915

ata atc  cac acg agc tca gaa  gtg gca atg act att  gct gct gca      7256
Ile Ile  His Thr Ser Ser Glu  Val Ala Met Thr Ile  Ala Ala Ala
    1920                 1925                 1930

tta gat  atg gct cct aat gtg  ttt ggt atg gca gtg  ggg gga tcc      7301
Leu Asp  Met Ala Pro Asn Val  Phe Gly Met Ala Val  Gly Gly Ser
    1935                 1940                 1945

cga tgg  gga gca gct agc act  gct gtg gca cag gga  ttg caa att      7346
Arg Trp  Gly Ala Ala Ser Thr  Ala Val Ala Gln Gly  Leu Gln Ile
    1950                 1955                 1960

agt gct  aat gta atg gaa cag  aca gct aat atc atg  gat atc agc      7391
Ser Ala  Asn Val Met Glu Gln  Thr Ala Asn Ile Met  Asp Ile Ser
    1965                 1970                 1975

gaa agt  tac cgc cga cgt cgt  gag gat tgg atg tta  cag aga gat      7436
Glu Ser  Tyr Arg Arg Arg Arg  Glu Asp Trp Met Leu  Gln Arg Asp
    1980                 1985                 1990

gct gcc  gag gca gaa gaa tcg  cag ttg aat tta caa  att aag gct      7481
Ala Ala  Glu Ala Glu Glu Ser  Gln Leu Asn Leu Gln  Ile Lys Ala
    1995                 2000                 2005

ctg caa  gaa cag att aac atg  gcc cgt aaa caa att  ttc ctg tcg      7526
Leu Gln  Glu Gln Ile Asn Met  Ala Arg Lys Gln Ile  Phe Leu Ser
    2010                 2015                 2020

gaa act  gaa cag gca cat gct  caa gca atc tac caa  ttg caa tgt      7571
Glu Thr  Glu Gln Ala His Ala  Gln Ala Ile Tyr Gln  Leu Gln Cys
    2025                 2030                 2035

act cgt  ttt tcg agt caa gct  tta tat aat tgg atg  gtt gga cgc      7616
Thr Arg  Phe Ser Ser Gln Ala  Leu Tyr Asn Trp Met  Val Gly Arg
    2040                 2045                 2050

tta tct  tct ctt tac tat caa  atg tat gac gca aca  tta tcc tta      7661
Leu Ser  Ser Leu Tyr Tyr Gln  Met Tyr Asp Ala Thr  Leu Ser Leu
    2055                 2060                 2065

tgt ttt  atg gca aag aat gct  tta gaa aaa gaa tta  gga aag gat      7706
Cys Phe  Met Ala Lys Asn Ala  Leu Glu Lys Glu Leu  Gly Lys Asp
    2070                 2075                 2080

aaa aca  aca gga atg ttt act  ctc cct gct tgg gat  gat ttg tat      7751
Lys Thr  Thr Gly Met Phe Thr  Leu Pro Ala Trp Asp  Asp Leu Tyr
    2085                 2090                 2095

caa ggg  cta ctt gct ggg gaa  atg tta atg gtg gaa  ctt caa aaa      7796
Gln Gly  Leu Leu Ala Gly Glu  Met Leu Met Val Glu  Leu Gln Lys
    2100                 2105                 2110

tta gaa  aat cta tgg cta gag  gaa aat aaa tgg ggt  atg gaa gca      7841
Leu Glu  Asn Leu Trp Leu Glu  Glu Asn Lys Trp Gly  Met Glu Ala
    2115                 2120                 2125

gtg aaa  act gta tcc tta gat  act ctt atc cgt aaa  aag aac cca      7886
Val Lys  Thr Val Ser Leu Asp  Thr Leu Ile Arg Lys  Lys Asn Pro
    2130                 2135                 2140

gag ttt  gct ttt gta gat ctt  gtt cag gaa gtt cta  agt ggc aaa      7931
Glu Phe  Ala Phe Val Asp Leu  Val Gln Glu Val Leu  Ser Gly Lys
    2145                 2150                 2155

att cct  gaa ggt gtg agt gga  ata gaa gtt aag ttg  caa aat aat      7976
Ile Pro  Glu Gly Val Ser Gly  Ile Glu Val Lys Leu  Gln Asn Asn
    2160                 2165                 2170

atc ttt  agt gca agt ctt gac  cta tcc tca ctt ggc  ttg gag aac      8021
Ile Phe  Ser Ala Ser Leu Asp  Leu Ser Ser Leu Gly  Leu Glu Asn
    2175                 2180                 2185

tct tat  aat cta aag gaa aag  aat cgt aaa atc aaa  aat ctg tca      8066
Ser Tyr  Asn Leu Lys Glu Lys  Asn Arg Lys Ile Lys  Asn Leu Ser
```

-continued

```
    2190                2195                2200

gtt acc  tta cca gca ctt tta  gga cct tat cag gat  gtg gaa gca      8111
Val Thr  Leu Pro Ala Leu Leu  Gly Pro Tyr Gln Asp  Val Glu Ala
    2205                2210                2215

acc tta  tca cta ggc ggt gaa  act gtt acg ctt tct  cat gga gta      8156
Thr Leu  Ser Leu Gly Gly Glu  Thr Val Thr Leu Ser  His Gly Val
    2220                2225                2230

gat gat  agt ggc tta ttc ata  aca gat ttc aat gac  agc cgt ttt      8201
Asp Asp  Ser Gly Leu Phe Ile  Thr Asp Phe Asn Asp  Ser Arg Phe
    2235                2240                2245

cta cct  ttc gag gga atg aat  ttg cta tcg ggg aca  ctt act tta      8246
Leu Pro  Phe Glu Gly Met Asn  Leu Leu Ser Gly Thr  Leu Thr Leu
    2250                2255                2260

gct att  ttc cat aca gga aaa  gat ggt gac cag cgc  tct tta cta      8291
Ala Ile  Phe His Thr Gly Lys  Asp Gly Asp Gln Arg  Ser Leu Leu
    2265                2270                2275

gaa agc  tta aat gat gtc ata  ttc cac att cga tat  gta atg aaa      8336
Glu Ser  Leu Asn Asp Val Ile  Phe His Ile Arg Tyr  Val Met Lys
    2280                2285                2290

tagttaagta attatatata ttcagaggct tgtaaaacag gcccttaag gaggatttgg   8396

att atg tca  cag act aac acc aat  gta gga tta ttt tca  cca tca      8441
    Met Ser  Gln Thr Asn Thr Asn  Val Gly Leu Phe Ser  Pro Ser
        2295                2300                2305

tta cca aaa  ggc gga gga tca att  aaa gga atg gag ggg  agc gtt      8486
Leu Pro Lys  Gly Gly Gly Ser Ile  Lys Gly Met Glu Gly  Ser Val
        2310                2315                2320

aca gct ccc  ggt tcc gat ggt atg  gca cgt ttt aac gtg  cca tta      8531
Thr Ala Pro  Gly Ser Asp Gly Met  Ala Arg Phe Asn Val  Pro Leu
        2325                2330                2335

cca gtc act  cct ggt cga acg att  act cca gat gta aac  ctt tcc      8576
Pro Val Thr  Pro Gly Arg Thr Ile  Thr Pro Asp Val Asn  Leu Ser
        2340                2345                2350

tat agc agt  gga aat gga aat ggt  cct ttt ggt atg ggt  tgg cac      8621
Tyr Ser Ser  Gly Asn Gly Asn Gly  Pro Phe Gly Met Gly  Trp His
        2355                2360                2365

atg gga ttc  atg tcc att cgc cga  aga aca aac act ggg  ata cct      8666
Met Gly Phe  Met Ser Ile Arg Arg  Arg Thr Asn Thr Gly  Ile Pro
        2370                2375                2380

agt tat aaa  tct gga gac cat ttt  att gga cct gat ggg  gaa gtg      8711
Ser Tyr Lys  Ser Gly Asp His Phe  Ile Gly Pro Asp Gly  Glu Val
        2385                2390                2395

cta gtt ccc  gaa agt gac gaa aat  gga caa gtt att act  cgt caa      8756
Leu Val Pro  Glu Ser Asp Glu Asn  Gly Gln Val Ile Thr  Arg Gln
        2400                2405                2410

aca gat act  act gct caa gga ata  tca tta ggt gaa cct  ttt att      8801
Thr Asp Thr  Thr Ala Gln Gly Ile  Ser Leu Gly Glu Pro  Phe Ile
        2415                2420                2425

gtt act cgc  tat ttc cca cga att  gaa agt aac ttt aac  ttg ata      8846
Val Thr Arg  Tyr Phe Pro Arg Ile  Glu Ser Asn Phe Asn  Leu Ile
        2430                2435                2440

gaa tat tgg  gaa gca aaa gaa gat  agt cac aca tca cca  ttt tgg      8891
Glu Tyr Trp  Glu Ala Lys Glu Asp  Ser His Thr Ser Pro  Phe Trp
        2445                2450                2455

ttg att cat  tct gct gat gga ata  ctc cat tgt ttt ggg  aaa act      8936
Leu Ile His  Ser Ala Asp Gly Ile  Leu His Cys Phe Gly  Lys Thr
        2460                2465                2470

gtc caa gca  aaa ata gct tcg cct  gat gat cct acc aag  ata gct      8981
Val Gln Ala  Lys Ile Ala Ser Pro  Asp Asp Pro Thr Lys  Ile Ala
        2475                2480                2485
```

-continued

```
gaa tgg cta  ctt gaa gag tct gta  tca cct ttt ggg gaa  cat gtt      9026
Glu Trp Leu  Leu Glu Glu Ser Val  Ser Pro Phe Gly Glu  His Val
        2490                 2495                 2500

tat tac caa  tac aaa gaa gaa gac  aac ata ggg att aat  cta aag      9071
Tyr Tyr Gln  Tyr Lys Glu Glu Asp  Asn Ile Gly Ile Asn  Leu Lys
        2505                 2510                 2515

cag gat act  cat caa tat ggg ggc  aac cgt tac ctt aaa  acc att      9116
Gln Asp Thr  His Gln Tyr Gly Gly  Asn Arg Tyr Leu Lys  Thr Ile
        2520                 2525                 2530

cgt tat ggg  aat aag gtt gca tat  cat tct ctt tac cta  tgg aat      9161
Arg Tyr Gly  Asn Lys Val Ala Tyr  His Ser Leu Tyr Leu  Trp Asn
        2535                 2540                 2545

ggg gaa atc  ccc atg gat agc caa  tgg ctt tat ttt gtg  atg cta      9206
Gly Glu Ile  Pro Met Asp Ser Gln  Trp Leu Tyr Phe Val  Met Leu
        2550                 2555                 2560

gat tat gga  gag aat gat aca tca  gta aac ggt tca cct  caa tat      9251
Asp Tyr Gly  Glu Asn Asp Thr Ser  Val Asn Gly Ser Pro  Gln Tyr
        2565                 2570                 2575

aca tat caa  ggt gaa tgg tta gcg  cgt gca gac tgt ttt  tct cgt      9296
Thr Tyr Gln  Gly Glu Trp Leu Ala  Arg Ala Asp Cys Phe  Ser Arg
        2580                 2585                 2590

tat gag tat  ggg ttt gaa acc cgt  acc tgc cga tta tgt  cgc caa      9341
Tyr Glu Tyr  Gly Phe Glu Thr Arg  Thr Cys Arg Leu Cys  Arg Gln
        2595                 2600                 2605

gta cta atg  ttt cat aac ttt aca  gag ttg aat gag gaa  ccc aca      9386
Val Leu Met  Phe His Asn Phe Thr  Glu Leu Asn Glu Glu  Pro Thr
        2610                 2615                 2620

tta att tgg  aag atg caa ttt gaa  tat gat gaa aat ccc  gcg gta      9431
Leu Ile Trp  Lys Met Gln Phe Glu  Tyr Asp Glu Asn Pro  Ala Val
        2625                 2630                 2635

tcc atg ttg  act gca gtt cag caa  ttg gct tat gaa aca  gac gga      9476
Ser Met Leu  Thr Ala Val Gln Gln  Leu Ala Tyr Glu Thr  Asp Gly
        2640                 2645                 2650

aaa ccg cta  agt atg cca cca cta  gaa ttt gat tat acg  cca ttt      9521
Lys Pro Leu  Ser Met Pro Pro Leu  Glu Phe Asp Tyr Thr  Pro Phe
        2655                 2660                 2665

gaa att cat  caa cct att gat tgg  caa cct ttt tta cca  gca cct      9566
Glu Ile His  Gln Pro Ile Asp Trp  Gln Pro Phe Leu Pro  Ala Pro
        2670                 2675                 2680

gaa tta aat  aat ggt gaa caa tat  caa att gtc gat ttg  tac gga      9611
Glu Leu Asn  Asn Gly Glu Gln Tyr  Gln Ile Val Asp Leu  Tyr Gly
        2685                 2690                 2695

gag ggt ata  cca ggt tta ttg tat  cga gac aaa agt cat  tgg cat      9656
Glu Gly Ile  Pro Gly Leu Leu Tyr  Arg Asp Lys Ser His  Trp His
        2700                 2705                 2710

tat cgt tct  cct gtt cga agt gac  aca cta gat ggt ata  aca tac      9701
Tyr Arg Ser  Pro Val Arg Ser Asp  Thr Leu Asp Gly Ile  Thr Tyr
        2715                 2720                 2725

gaa agc tgg  aag tcc tta cct caa  atc ccg gtg aac gtc  cag aat      9746
Glu Ser Trp  Lys Ser Leu Pro Gln  Ile Pro Val Asn Val  Gln Asn
        2730                 2735                 2740

gga atg tta  tta gat atg aat ggt  gat gga tat ttg gaa  tgg ctg      9791
Gly Met Leu  Leu Asp Met Asn Gly  Asp Gly Tyr Leu Glu  Trp Leu
        2745                 2750                 2755

ata gca caa  tcg gga gta ata gga  agc tac acc atg aat  cca gat      9836
Ile Ala Gln  Ser Gly Val Ile Gly  Ser Tyr Thr Met Asn  Pro Asp
        2760                 2765                 2770

aaa aca tgg  tcc aat ttt gta cca  ttc aaa gct ctg cca  aca gag      9881
Lys Thr Trp  Ser Asn Phe Val Pro  Phe Lys Ala Leu Pro  Thr Glu
```

-continued

```
        2775                2780                2785

ttt ttc cat  cca aag gca cag ctt  tct aat gtt act ggc  tca ggt      9926
Phe Phe His  Pro Lys Ala Gln Leu  Ser Asn Val Thr Gly  Ser Gly
        2790                2795                2800

tta cca gat  tta gtt atg att gga  cct aaa agc gtt cga  ttt tat      9971
Leu Pro Asp  Leu Val Met Ile Gly  Pro Lys Ser Val Arg  Phe Tyr
        2805                2810                2815

gca ggg gaa  gaa tcg ggt ttc aaa  cga tca cgt gaa gtg  tgg caa     10016
Ala Gly Glu  Glu Ser Gly Phe Lys  Arg Ser Arg Glu Val  Trp Gln
        2820                2825                2830

aaa gcg ggt  att act ttg cca att  gaa ggc ttg aat gag  aaa gaa     10061
Lys Ala Gly  Ile Thr Leu Pro Ile  Glu Gly Leu Asn Glu  Lys Glu
        2835                2840                2845

ctg ata gca  ttt agt gat atg tta  ggg tct gga cag tca  cat tta     10106
Leu Ile Ala  Phe Ser Asp Met Leu  Gly Ser Gly Gln Ser  His Leu
        2850                2855                2860

gta cgt ata  cga cat gat ggt gtt  acg tgc tgg ccg aat  atg gga     10151
Val Arg Ile  Arg His Asp Gly Val  Thr Cys Trp Pro Asn  Met Gly
        2865                2870                2875

caa gga ata  ttt ggg gaa cca ttg  gta ctt cca gga ttc  act ata     10196
Gln Gly Ile  Phe Gly Glu Pro Leu  Val Leu Pro Gly Phe  Thr Ile
        2880                2885                2890

aat gaa agg  gat ttt gat cca aag  cgt gta tat ctt gcg  gat ctt     10241
Asn Glu Arg  Asp Phe Asp Pro Lys  Arg Val Tyr Leu Ala  Asp Leu
        2895                2900                2905

gat ggt tct  ggt act tct gac gtg  att tat gcg tct cat  gat gca     10286
Asp Gly Ser  Gly Thr Ser Asp Val  Ile Tyr Ala Ser His  Asp Ala
        2910                2915                2920

ttg cac att  tat caa aat ctt tct  gga aat agc ttt gcg  gat ccg     10331
Leu His Ile  Tyr Gln Asn Leu Ser  Gly Asn Ser Phe Ala  Asp Pro
        2925                2930                2935

gta cag att  cca ctt cct gcc ggt  gta cat ttt gat aat  tta tgc     10376
Val Gln Ile  Pro Leu Pro Ala Gly  Val His Phe Asp Asn  Leu Cys
        2940                2945                2950

cgg ttg caa  cct gct gat atc agc  gga aga ggt ata tct  aat cta     10421
Arg Leu Gln  Pro Ala Asp Ile Ser  Gly Arg Gly Ile Ser  Asn Leu
        2955                2960                2965

gta cta aat  gta ccc tac ata tcc  ccg cgt agt tgg tat  ttg gat     10466
Val Leu Asn  Val Pro Tyr Ile Ser  Pro Arg Ser Trp Tyr  Leu Asp
        2970                2975                2980

tta tgc tct  ata aag ccc tat tta  ttg aaa agt act agc  aac aat     10511
Leu Cys Ser  Ile Lys Pro Tyr Leu  Leu Lys Ser Thr Ser  Asn Asn
        2985                2990                2995

ctt gga gct  tct aac gaa ttc ttt  tat cga agt tcc gca  cag tat     10556
Leu Gly Ala  Ser Asn Glu Phe Phe  Tyr Arg Ser Ser Ala  Gln Tyr
        3000                3005                3010

tgg ctt gat  gaa aaa cag tct gat  tca tcg gtt gtt tgc  aca tta     10601
Trp Leu Asp  Glu Lys Gln Ser Asp  Ser Ser Val Val Cys  Thr Leu
        3015                3020                3025

ccg ttt ccg  ata aac gtt ata tct  tgt att caa aca cta  gat gaa     10646
Pro Phe Pro  Ile Asn Val Ile Ser  Cys Ile Gln Thr Leu  Asp Glu
        3030                3035                3040

att agc ggt  agt acg aaa ata caa  gaa tat act tac cgt  aat ggt     10691
Ile Ser Gly  Ser Thr Lys Ile Gln  Glu Tyr Thr Tyr Arg  Asn Gly
        3045                3050                3055

gtg tat gat  cga atg gaa aaa gaa  ttt gct gga ttt ggt  tac att     10736
Val Tyr Asp  Arg Met Glu Lys Glu  Phe Ala Gly Phe Gly  Tyr Ile
        3060                3065                3070

gtt aca aag  gta gaa gaa aga gac  tac gaa gga agc att  agt aaa     10781
```

-continued

```
Val Thr Lys  Val Glu Glu Arg Asp  Tyr Glu Gly Ser Ile  Ser Lys
        3075                 3080                 3085

aat act caa  ccg ata cta aca cgt  agt tgg tat cat acc  gga caa      10826
Asn Thr Gln  Pro Ile Leu Thr Arg  Ser Trp Tyr His Thr  Gly Gln
        3090                 3095                 3100

caa gag gac  gat act cgt aca ttt  act caa tct tgg aaa  gga gat      10871
Gln Glu Asp  Asp Thr Arg Thr Phe  Thr Gln Ser Trp Lys  Gly Asp
        3105                 3110                 3115

cct atc gct  ttt cat ctc aaa cca  agt cga ttt aca aca  ttt gat      10916
Pro Ile Ala  Phe His Leu Lys Pro  Ser Arg Phe Thr Thr  Phe Asp
        3120                 3125                 3130

tta aat gtg  aca aag gat gta cca  ctg gat tcc cta aat  gaa cga      10961
Leu Asn Val  Thr Lys Asp Val Pro  Leu Asp Ser Leu Asn  Glu Arg
        3135                 3140                 3145

caa gaa tat  tgg ctg tat cgc tca  tta aaa gga atg cca  cta cgt      11006
Gln Glu Tyr  Trp Leu Tyr Arg Ser  Leu Lys Gly Met Pro  Leu Arg
        3150                 3155                 3160

acg gaa atc  ttt aga gga gat atg  tta gaa tcg tct cct  tat cta      11051
Thr Glu Ile  Phe Arg Gly Asp Met  Leu Glu Ser Ser Pro  Tyr Leu
        3165                 3170                 3175

gta gag agc  tac cgt tat caa gta  cgg ttg gta cag agt  act gat      11096
Val Glu Ser  Tyr Arg Tyr Gln Val  Arg Leu Val Gln Ser  Thr Asp
        3180                 3185                 3190

tca gaa tgt  gtt gta ttg cca tta  caa ttg gaa cag ctt  act tat      11141
Ser Glu Cys  Val Val Leu Pro Leu  Gln Leu Glu Gln Leu  Thr Tyr
        3195                 3200                 3205

aat tat gag  caa att tct tct gat  cca caa tgt acg cag  caa ata      11186
Asn Tyr Glu  Gln Ile Ser Ser Asp  Pro Gln Cys Thr Gln  Gln Ile
        3210                 3215                 3220

cag caa ttc  ttc gac gag tat ggt  tct tcg aca caa agt  gtc aca      11231
Gln Gln Phe  Phe Asp Glu Tyr Gly  Ser Ser Thr Gln Ser  Val Thr
        3225                 3230                 3235

att cac tac  ccg cgt cgg gaa cag  cca aat gaa aac ccg  tat cct      11276
Ile His Tyr  Pro Arg Arg Glu Gln  Pro Asn Glu Asn Pro  Tyr Pro
        3240                 3245                 3250

gat aca cta  cca gat act agt tgg  agt agc agc tat gat  tct caa      11321
Asp Thr Leu  Pro Asp Thr Ser Trp  Ser Ser Ser Tyr Asp  Ser Gln
        3255                 3260                 3265

caa atg tta  cta cgc ttt aca cga  caa aga gaa aaa gcg  tat cac      11366
Gln Met Leu  Leu Arg Phe Thr Arg  Gln Arg Glu Lys Ala  Tyr His
        3270                 3275                 3280

ctt aca aat  tct gag aac tgg cgt  cta gga ata cct cat  cag aac      11411
Leu Thr Asn  Ser Glu Asn Trp Arg  Leu Gly Ile Pro His  Gln Asn
        3285                 3290                 3295

cgc cta gat  gct ttt gtc tat cct  gct gaa agt gta ccg  aat gaa      11456
Arg Leu Asp  Ala Phe Val Tyr Pro  Ala Glu Ser Val Pro  Asn Glu
        3300                 3305                 3310

ggc ata agt  act gag tta ctg ggg  gat gac ggt act tta  caa act      11501
Gly Ile Ser  Thr Glu Leu Leu Gly  Asp Asp Gly Thr Leu  Gln Thr
        3315                 3320                 3325

cct gcg cag  gaa cag gct tat gga  gga cag aca gag gtc  att tat      11546
Pro Ala Gln  Glu Gln Ala Tyr Gly  Gly Gln Thr Glu Val  Ile Tyr
        3330                 3335                 3340

gtg ggg gat  aac aaa cca gat ttg  cgt gca ctg att tat  tac acg      11591
Val Gly Asp  Asn Lys Pro Asp Leu  Arg Ala Leu Ile Tyr  Tyr Thr
        3345                 3350                 3355

aga agc gca  gtt ctt gat gaa gtc  tgt tta caa gct tat  gaa gga      11636
Arg Ser Ala  Val Leu Asp Glu Val  Cys Leu Gln Ala Tyr  Glu Gly
        3360                 3365                 3370
```

-continued

```
ata ctt agt  gat gaa caa tta aac  ttg ctt ctt aca tca  gct ggt     11681
Ile Leu Ser  Asp Glu Gln Leu Asn  Leu Leu Leu Thr Ser  Ala Gly
        3375                 3380                 3385

tat aaa caa  agt aca cgg ata tta  gga ttt gaa gac gaa  cca gat     11726
Tyr Lys Gln  Ser Thr Arg Ile Leu  Gly Phe Glu Asp Glu  Pro Asp
        3390                 3395                 3400

gta tta gtg  gca gaa caa gga ttt  act cgt tat aca aat  aaa gag     11771
Val Leu Val  Ala Glu Gln Gly Phe  Thr Arg Tyr Thr Asn  Lys Glu
        3405                 3410                 3415

ggc ttt tat  cga atg gta ggg caa  caa gct tct atg tta  act gga     11816
Gly Phe Tyr  Arg Met Val Gly Gln  Gln Ala Ser Met Leu  Thr Gly
        3420                 3425                 3430

gag caa gta  ttg tca tgg gat gat  aat tgg tgt gtg gtg  ata tca     11861
Glu Gln Val  Leu Ser Trp Asp Asp  Asn Trp Cys Val Val  Ile Ser
        3435                 3440                 3445

gct gaa gac  gct gtg aaa aat aaa  acc cag att gca tat  gat tat     11906
Ala Glu Asp  Ala Val Lys Asn Lys  Thr Gln Ile Ala Tyr  Asp Tyr
        3450                 3455                 3460

cgc ttt ttg  caa gcc aat caa att  ata gat gcc aat aac  aat gta     11951
Arg Phe Leu  Gln Ala Asn Gln Ile  Ile Asp Ala Asn Asn  Asn Val
        3465                 3470                 3475

agt cag gtt  caa ttg gat gct ctc  ggc cga gta ata tat  agc cgt     11996
Ser Gln Val  Gln Leu Asp Ala Leu  Gly Arg Val Ile Tyr  Ser Arg
        3480                 3485                 3490

atc tgg gga  acc gaa aaa gga gaa  gat gta ggt ttt aac  cca gca     12041
Ile Trp Gly  Thr Glu Lys Gly Glu  Asp Val Gly Phe Asn  Pro Ala
        3495                 3500                 3505

tta caa ttt  tca tca cct gaa acg  att gac caa gcg ctt  act ttg     12086
Leu Gln Phe  Ser Ser Pro Glu Thr  Ile Asp Gln Ala Leu  Thr Leu
        3510                 3515                 3520

gta cca cct  tta cct gtt gga tct  tgt tat gta tac gat  acg aat     12131
Val Pro Pro  Leu Pro Val Gly Ser  Cys Tyr Val Tyr Asp  Thr Asn
        3525                 3530                 3535

agt tgg atg  ggg aaa ata tca ttt  gaa caa ctt tct gaa  ctc gtc     12176
Ser Trp Met  Gly Lys Ile Ser Phe  Glu Gln Leu Ser Glu  Leu Val
        3540                 3545                 3550

tca gat ggt  aca gaa ttg tgg aat  ttc ctg ata gcc aat  cgt ttt     12221
Ser Asp Gly  Thr Glu Leu Trp Asn  Phe Leu Ile Ala Asn  Arg Phe
        3555                 3560                 3565

att acg tta  gac gga aga ata cga  act cgt ggt cgt ttt  caa aag     12266
Ile Thr Leu  Asp Gly Arg Ile Arg  Thr Arg Gly Arg Phe  Gln Lys
        3570                 3575                 3580

gat tta tcc  caa tta tca caa act  gtt tcg aat ata ttc  aaa ggt     12311
Asp Leu Ser  Gln Leu Ser Gln Thr  Val Ser Asn Ile Phe  Lys Gly
        3585                 3590                 3595

gca ata cgc  aat ccg tcc cat act  tta att tta aaa gcg  gat cgt     12356
Ala Ile Arg  Asn Pro Ser His Thr  Leu Ile Leu Lys Ala  Asp Arg
        3600                 3605                 3610

tat cca gat  gat cca gct cag caa  att caa act aca atc  atc ttc     12401
Tyr Pro Asp  Asp Pro Ala Gln Gln  Ile Gln Thr Thr Ile  Ile Phe
        3615                 3620                 3625

agt gat ggt  ttt gga cgt atg tta  cag agt tcc caa aaa  gca gaa     12446
Ser Asp Gly  Phe Gly Arg Met Leu  Gln Ser Ser Gln Lys  Ala Glu
        3630                 3635                 3640

cct aag gga  gat atc tta gat aac  gca aaa gag aat tta  att aag     12491
Pro Lys Gly  Asp Ile Leu Asp Asn  Ala Lys Glu Asn Leu  Ile Lys
        3645                 3650                 3655

agc gaa aat  aaa acg cga tgg att  att tca gaa cgt gca  gat tat     12536
Ser Glu Asn  Lys Thr Arg Trp Ile  Ile Ser Glu Arg Ala  Asp Tyr
        3660                 3665                 3670
```

-continued

```
gat ggg aaa  ggc aca gtg att cga  aac ttt caa cct att  tat ctt     12581
Asp Gly Lys  Gly Thr Val Ile Arg  Asn Phe Gln Pro Ile  Tyr Leu
        3675                 3680                 3685

cat gat tgg  caa tat gtt aat aat  gaa tct att cat agt  cag atg     12626
His Asp Trp  Gln Tyr Val Asn Asn  Glu Ser Ile His Ser  Gln Met
        3690                 3695                 3700

tgt gca aca  aac tat tat tac gat  gct tta tca cga caa  atc aga     12671
Cys Ala Thr  Asn Tyr Tyr Tyr Asp  Ala Leu Ser Arg Gln  Ile Arg
        3705                 3710                 3715

gtg gtg aat  gcg aaa gga tac gag  caa cgt aat gct ttt  tat cca     12716
Val Val Asn  Ala Lys Gly Tyr Glu  Gln Arg Asn Ala Phe  Tyr Pro
        3720                 3725                 3730

tgg ttt aca  gta aat gaa gat gaa  aat gat act tgg aat  aat gga     12761
Trp Phe Thr  Val Asn Glu Asp Glu  Asn Asp Thr Trp Asn  Asn Gly
        3735                 3740                 3745

gga atg gaa  gaa tagtaaatat tttagaggcg ttcctatcca attacaattc       12813
Gly Met Glu  Glu
        3750

ttctttaaat acgtatactg tttggtattt ctatagattc cttgtaactt tgagtatggt  12873

ttctattcaa atcgactaac cacctacaag ggacgtaaac gtcccttact ttttatcact  12933

atttattctc taccgtctct ttacggtaaa tcgagggagg ggaaatt ttg gat aca    12989
                                                    Leu Asp Thr

aat  tct ata tat aat ggg  aca cct acg att tct  gtt ata gat aat     13034
Asn  Ser Ile Tyr Asn Gly  Thr Pro Thr Ile Ser  Val Ile Asp Asn
3755                 3760                 3765

agg  ggc tta cag att cgt  acc ctt gaa tat aat  cgt gtt aca gtt     13079
Arg  Gly Leu Gln Ile Arg  Thr Leu Glu Tyr Asn  Arg Val Thr Val
3770                 3775                 3780

gag  gac ccc ata gat gaa  tat gtc act cga aac  act tat aca ttg     13124
Glu  Asp Pro Ile Asp Glu  Tyr Val Thr Arg Asn  Thr Tyr Thr Leu
3785                 3790                 3795

tta  gga aat ctt gat gat  agt atg gat cct cgt  cta ttt tca caa     13169
Leu  Gly Asn Leu Asp Asp  Ser Met Asp Pro Arg  Leu Phe Ser Gln
3800                 3805                 3810

tat  caa aat aac gat aat  aca cta cca aat atg  aga tac gat cat     13214
Tyr  Gln Asn Asn Asp Asn  Thr Leu Pro Asn Met  Arg Tyr Asp His
3815                 3820                 3825

tct  tta aaa ggg aat ata  cta tgt act gaa agt  gtg gat gct gga     13259
Ser  Leu Lys Gly Asn Ile  Leu Cys Thr Glu Ser  Val Asp Ala Gly
3830                 3835                 3840

caa  aag gta caa atc ttt  aat ata gag gga cga  cca att tgg ttt     13304
Gln  Lys Val Gln Ile Phe  Asn Ile Glu Gly Arg  Pro Ile Trp Phe
3845                 3850                 3855

agg  gat gca aat cgt aca  caa aca act atg gaa  tac gat tta gta     13349
Arg  Asp Ala Asn Arg Thr  Gln Thr Thr Met Glu  Tyr Asp Leu Val
3860                 3865                 3870

gga  aga cca aca gct gtg  ttg gaa aaa ctg gat  ggc aat gaa acc     13394
Gly  Arg Pro Thr Ala Val  Leu Glu Lys Leu Asp  Gly Asn Glu Thr
3875                 3880                 3885

cct  aaa tat agg gag cgt  ttt ttt tac ggt gag  aac gaa agg ggt     13439
Pro  Lys Tyr Arg Glu Arg  Phe Phe Tyr Gly Glu  Asn Glu Arg Gly
3890                 3895                 3900

gcc  caa gcc aac aat tta  tgt ggt cag ttg gtg  tgt cat tac gat     13484
Ala  Gln Ala Asn Asn Leu  Cys Gly Gln Leu Val  Cys His Tyr Asp
3905                 3910                 3915

atc  gca ggt cgt aat caa  aca aaa agc ttt tct  tta tct gga tta     13529
Ile  Ala Gly Arg Asn Gln  Thr Lys Ser Phe Ser  Leu Ser Gly Leu
3920                 3925                 3930
```

-continued

```
cca  ctt tat caa agt cgg  caa ttg tta aag aat  att gat gaa cct     13574
Pro  Leu Tyr Gln Ser Arg  Gln Leu Leu Lys Asn  Ile Asp Glu Pro
3935                3940                3945

agc  aac tgg agc gct gat  ggt gaa agt gct tgg  ata aat ttt ctt     13619
Ser  Asn Trp Ser Ala Asp  Gly Glu Ser Ala Trp  Ile Asn Phe Leu
3950                3955                3960

gat  aca gaa acc tat gat  aca agc tgg caa tat  gac gta caa gga     13664
Asp  Thr Glu Thr Tyr Asp  Thr Ser Trp Gln Tyr  Asp Val Gln Gly
3965                3970                3975

aaa  aaa tta tct caa ata  gat gcc aaa ggt aat  ctt caa aca ttt     13709
Lys  Lys Leu Ser Gln Ile  Asp Ala Lys Gly Asn  Leu Gln Thr Phe
3980                3985                3990

act  tat aat tct att ggt  caa ccc aaa aac att  cat att aaa ctg     13754
Thr  Tyr Asn Ser Ile Gly  Gln Pro Lys Asn Ile  His Ile Lys Leu
3995                4000                4005

tgg  ggt cag ata gaa caa  agt att gta aat ggg  ata gaa tac aat     13799
Trp  Gly Gln Ile Glu Gln  Ser Ile Val Asn Gly  Ile Glu Tyr Asn
4010                4015                4020

gct  gca ggg caa gtg cta  aga act gag gca gga  aat ggt atc gta     13844
Ala  Ala Gly Gln Val Leu  Arg Thr Glu Ala Gly  Asn Gly Ile Val
4025                4030                4035

aca  gaa tat aca tat gaa  gaa agc tca caa cgc  tta atg aga aaa     13889
Thr  Glu Tyr Thr Tyr Glu  Glu Ser Ser Gln Arg  Leu Met Arg Lys
4040                4045                4050

aaa  gat tca cgc aag ata  ccc tct aaa aga aga  gaa ata ctg caa     13934
Lys  Asp Ser Arg Lys Ile  Pro Ser Lys Arg Arg  Glu Ile Leu Gln
4055                4060                4065

gat  tat cat tat gaa tat  gac cct gta ggg aat  atc ttg tct att     13979
Asp  Tyr His Tyr Glu Tyr  Asp Pro Val Gly Asn  Ile Leu Ser Ile
4070                4075                4080

agt  aat gaa atg gat tcg  gtt tgc ttt ttc cgt  aac caa ata att     14024
Ser  Asn Glu Met Asp Ser  Val Cys Phe Phe Arg  Asn Gln Ile Ile
4085                4090                4095

gta  cca aaa cgg caa tat  aca tat gat aca ctg  tat cgg ctt att     14069
Val  Pro Lys Arg Gln Tyr  Thr Tyr Asp Thr Leu  Tyr Arg Leu Ile
4100                4105                4110

tct  agt tca ggg agg gaa  tct gat acg ctt cgc  cag tac caa tcc     14114
Ser  Ser Ser Gly Arg Glu  Ser Asp Thr Leu Arg  Gln Tyr Gln Ser
4115                4120                4125

ttc  cca tcc gtg ata acg  cct att cca cta gat  gat aac cag tat     14159
Phe  Pro Ser Val Ile Thr  Pro Ile Pro Leu Asp  Asp Asn Gln Tyr
4130                4135                4140

gta  aat tat tct gaa aaa  tat agt tat gat cgt  gct gga aat ttg     14204
Val  Asn Tyr Ser Glu Lys  Tyr Ser Tyr Asp Arg  Ala Gly Asn Leu
4145                4150                4155

ata  aaa ctt agt cat act  gga gca act caa tat  act acc aat att     14249
Ile  Lys Leu Ser His Thr  Gly Ala Thr Gln Tyr  Thr Thr Asn Ile
4160                4165                4170

gat  gtc gat gtt gct tca  aat aga ggg ctt ttg  agc cta gaa aat     14294
Asp  Val Asp Val Ala Ser  Asn Arg Gly Leu Leu  Ser Leu Glu Asn
4175                4180                4185

aat  gta tca aat ttt gag  aat tat ctc gat aga  gca ggt aat caa     14339
Asn  Val Ser Asn Phe Glu  Asn Tyr Leu Asp Arg  Ala Gly Asn Gln
4190                4195                4200

aaa  att tta ctt cca gga  ata cct atg gaa tgg  gat gca cga aat     14384
Lys  Ile Leu Leu Pro Gly  Ile Pro Met Glu Trp  Asp Ala Arg Asn
4205                4210                4215

caa  tta agc cgt gtc aat  atg gtg gta cgt gaa  gat aaa gaa aac     14429
Gln  Leu Ser Arg Val Asn  Met Val Val Arg Glu  Asp Lys Glu Asn
```

-continued

```
4220                4225                4230

gat  tgg gaa ggt tat ctc  tat aat agt tca gga  atg aga atc gta     14474
Asp  Trp Glu Gly Tyr Leu  Tyr Asn Ser Ser Gly  Met Arg Ile Val
4235                4240                4245

aaa  cag gat act cga aag  aaa caa gat ata act  aaa act gat acg     14519
Lys  Gln Asp Thr Arg Lys  Lys Gln Asp Ile Thr  Lys Thr Asp Thr
4250                4255                4260

aca  att tat ttg ccg gga  cta gaa ctg cgt aca  cgt caa att ggt     14564
Thr  Ile Tyr Leu Pro Gly  Leu Glu Leu Arg Thr  Arg Gln Ile Gly
4265                4270                4275

gat  aat gtt aca gaa gtc  ctg caa ata gtt aca  gca gca caa gta     14609
Asp  Asn Val Thr Glu Val  Leu Gln Ile Val Thr  Ala Ala Gln Val
4280                4285                4290

agg  gta tta cat tgg aaa  gat gaa acg caa cct  act ggt ata aca     14654
Arg  Val Leu His Trp Lys  Asp Glu Thr Gln Pro  Thr Gly Ile Thr
4295                4300                4305

aat  aat caa tat cga tac  agc gtc acg gat cat  cta ggt tca tct     14699
Asn  Asn Gln Tyr Arg Tyr  Ser Val Thr Asp His  Leu Gly Ser Ser
4310                4315                4320

tca  tta gag tta gat aag  caa ggg aaa atc ata  agt aag gaa gaa     14744
Ser  Leu Glu Leu Asp Lys  Gln Gly Lys Ile Ile  Ser Lys Glu Glu
4325                4330                4335

ttt  tat cca tat ggc ggt  aca gcc tta tgg aca  gct cgt aca gaa     14789
Phe  Tyr Pro Tyr Gly Gly  Thr Ala Leu Trp Thr  Ala Arg Thr Glu
4340                4345                4350

att  gag gca aat tat aag  act att cgc tat tcc  gga aag gaa cga     14834
Ile  Glu Ala Asn Tyr Lys  Thr Ile Arg Tyr Ser  Gly Lys Glu Arg
4355                4360                4365

gat  gct aca ggt ttg tat  tat tat gga cac aga  tac tat atg cca     14879
Asp  Ala Thr Gly Leu Tyr  Tyr Tyr Gly His Arg  Tyr Tyr Met Pro
4370                4375                4380

tgg  gct gga agg tgg tta  aac cct gat cct gct  ggt aca gta gat     14924
Trp  Ala Gly Arg Trp Leu  Asn Pro Asp Pro Ala  Gly Thr Val Asp
4385                4390                4395

gga  tta aat tta tat cgt  atg gtg agg aat aac  ccc ata aat cta     14969
Gly  Leu Asn Leu Tyr Arg  Met Val Arg Asn Asn  Pro Ile Asn Leu
4400                4405                4410

ata  gat cct gat gga aat  gca cca ata caa ata  acg aat tat agt     15014
Ile  Asp Pro Asp Gly Asn  Ala Pro Ile Gln Ile  Thr Asn Tyr Ser
4415                4420                4425

aaa  gaa aat ggt gat tta  ttt tat ggc ctt gct  aac gag aga ggg     15059
Lys  Glu Asn Gly Asp Leu  Phe Tyr Gly Leu Ala  Asn Glu Arg Gly
4430                4435                4440

cga  tat ata gaa gca gcc  ctt aga gga aaa act  ttt gtt tca gat     15104
Arg  Tyr Ile Glu Ala Ala  Leu Arg Gly Lys Thr  Phe Val Ser Asp
4445                4450                4455

tcg  gca gaa agc gaa cct  atg att ata gat caa  tat aac aat gaa     15149
Ser  Ala Glu Ser Glu Pro  Met Ile Ile Asp Gln  Tyr Asn Asn Glu
4460                4465                4470

gtc  tca aag cat ata ttg  aat aaa aac ata aaa  ggt atg aaa att     15194
Val  Ser Lys His Ile Leu  Asn Lys Asn Ile Lys  Gly Met Lys Ile
4475                4480                4485

gcg  gaa cat ccc aaa gta  cca aag gat tta aaa  gat atc att tct     15239
Ala  Glu His Pro Lys Val  Pro Lys Asp Leu Lys  Asp Ile Ile Ser
4490                4495                4500

aca  gat aag aga gga aga  tat cct ttg tgg gac  gat tat ttt act     15284
Thr  Asp Lys Arg Gly Arg  Tyr Pro Leu Trp Asp  Asp Tyr Phe Thr
4505                4510                4515

aga  gga atg gag aac tta  aaa ttt aat ata ggg  gct atc tat aaa     15329
```

-continued

```
Arg  Gly Met Glu Asn Leu  Lys Phe Asn Ile Gly  Ala Ile Tyr Lys
4520                 4525                 4530

gag  act aaa gat aaa att  aat act gat act tat  cat aaa tat tac     15374
Glu  Thr Lys Asp Lys Ile  Asn Thr Asp Thr Tyr  His Lys Tyr Tyr
4535                 4540                 4545

acg  ggc ggc ggg gcg gat  agg gtc cca aag cta  cta tgg aaa cga     15419
Thr  Gly Gly Gly Ala Asp  Arg Val Pro Lys Leu  Leu Trp Lys Arg
4550                 4555                 4560

ggt  agt aaa tta ggc ata  gcg att gct gct tca  aat cag aaa aca     15464
Gly  Ser Lys Leu Gly Ile  Ala Ile Ala Ala Ser  Asn Gln Lys Thr
4565                 4570                 4575

aaa  ata cat ttt gta ctc  gat aat tta gat att  gaa agc ata gtt     15509
Lys  Ile His Phe Val Leu  Asp Asn Leu Asp Ile  Glu Ser Ile Val
4580                 4585                 4590

gct  aag aga ggt gat tct  ggt gaa tca att aca  gct tcc gag tta     15554
Ala  Lys Arg Gly Asp Ser  Gly Glu Ser Ile Thr  Ala Ser Glu Leu
4595                 4600                 4605

cgc  tat gtt tat cga aac  cgt gag aga tta cag  ggg cgt gta gtt     15599
Arg  Tyr Val Tyr Arg Asn  Arg Glu Arg Leu Gln  Gly Arg Val Val
4610                 4615                 4620

ttc  tat aga aac gga gag  aaa cta gag acg act  cca cgg aat gat     15644
Phe  Tyr Arg Asn Gly Glu  Lys Leu Glu Thr Thr  Pro Arg Asn Asp
4625                 4630                 4635

agt  cct gat tta tgg gaa  cag tat agt ccc aaa  aat aga gca ata     15689
Ser  Pro Asp Leu Trp Glu  Gln Tyr Ser Pro Lys  Asn Arg Ala Ile
4640                 4645                 4650

caa  aaa act gtg caa aaa  aat agt ttt gcg ggt  gtt ttc tcc aag     15734
Gln  Lys Thr Val Gln Lys  Asn Ser Phe Ala Gly  Val Phe Ser Lys
4655                 4660                 4665

tgt  att cga tgagataaaa tctttgagaa aaataattat tctacacagt           15783
Cys  Ile Arg
4670

gaaaggagat tataaaaat atg aat aca  cca tct atc tat agc  ggt act     15832
                     Met Asn Thr  Pro Ser Ile Tyr Ser  Gly Thr
                             4675                 4680

cct acg att  tcg gtt gta gat aac  aga aat tta cag att  cgt gac     15877
Pro Thr Ile  Ser Val Val Asp Asn  Arg Asn Leu Gln Ile  Arg Asp
        4685                 4690                 4695

cta aga tat  aat cgt ctt gaa aaa  aga gat tta gta gat  gag tat     15922
Leu Arg Tyr  Asn Arg Leu Glu Lys  Arg Asp Leu Val Asp  Glu Tyr
        4700                 4705                 4710

atc acc cga  aac act tat aca tta  tta gga aat ctt gaa  agt agc     15967
Ile Thr Arg  Asn Thr Tyr Thr Leu  Leu Gly Asn Leu Glu  Ser Ser
        4715                 4720                 4725

ata gat cct  cgc ttg ttt tca caa  tat caa gat gat aac  agt aca     16012
Ile Asp Pro  Arg Leu Phe Ser Gln  Tyr Gln Asp Asp Asn  Ser Thr
        4730                 4735                 4740

tca ccg aat  ata aat agc ttt cct  tct cta aga gga gag  gaa ctc     16057
Ser Pro Asn  Ile Asn Ser Phe Pro  Ser Leu Arg Gly Glu  Glu Leu
        4745                 4750                 4755

cgt act gaa  agt gtg gat gct ggt  cgg aag gta aac cta  ttt aat     16102
Arg Thr Glu  Ser Val Asp Ala Gly  Arg Lys Val Asn Leu  Phe Asn
        4760                 4765                 4770

gca gaa gga  aaa tcc atc tgg ttt  atg gac ccc aat aat  ata gag     16147
Ala Glu Gly  Lys Ser Ile Trp Phe  Met Asp Pro Asn Asn  Ile Glu
        4775                 4780                 4785

aca agt agc  gat tat gat ttg gta  gga cga ccc ata gct  gta ttt     16192
Thr Ser Ser  Asp Tyr Asp Leu Val  Gly Arg Pro Ile Ala  Val Phe
        4790                 4795                 4800
```

-continued

```
gaa aag caa  gaa gac gag gaa ata  cct caa tgt aaa gat  cgg ttt      16237
Glu Lys Gln  Glu Asp Glu Glu Ile  Pro Gln Cys Lys Asp  Arg Phe
        4805                 4810                 4815

att tat ggg  gaa gat gaa aga aat  gcc cta gct aac aat  ttg cgt      16282
Ile Tyr Gly  Glu Asp Glu Arg Asn  Ala Leu Ala Asn Asn  Leu Arg
        4820                 4825                 4830

ggt caa ctt  gta cgt cat tat gat  acc gca ggt cgg ata  caa aca      16327
Gly Gln Leu  Val Arg His Tyr Asp  Thr Ala Gly Arg Ile  Gln Thr
        4835                 4840                 4845

gaa aac ttc  tca ttg aca gga atg  cca ctt aat cag tct  cgg caa      16372
Glu Asn Phe  Ser Leu Thr Gly Met  Pro Leu Asn Gln Ser  Arg Gln
        4850                 4855                 4860

ttg tta aaa  aat atg aat caa tct  agc aac tgg att ata  gat gat      16417
Leu Leu Lys  Asn Met Asn Gln Ser  Ser Asn Trp Ile Ile  Asp Asp
        4865                 4870                 4875

gaa aat act  tgg act aac ctg ctt  gat gct gaa acc tat  agt acc      16462
Glu Asn Thr  Trp Thr Asn Leu Leu  Asp Ala Glu Thr Tyr  Ser Thr
        4880                 4885                 4890

aac tgg caa  tat gat gta caa ggg  aga aaa gtc gct caa  ata gat      16507
Asn Trp Gln  Tyr Asp Val Gln Gly  Arg Lys Val Ala Gln  Ile Asp
        4895                 4900                 4905

gcc aag ggt  aat ctg cag aca gtt  act tac aat att ttg  ggc caa      16552
Ala Lys Gly  Asn Leu Gln Thr Val  Thr Tyr Asn Ile Leu  Gly Gln
        4910                 4915                 4920

cca aaa gct  gtt aat ctt aca tta  caa gac caa tcg gaa  cag agc      16597
Pro Lys Ala  Val Asn Leu Thr Leu  Gln Asp Gln Ser Glu  Gln Ser
        4925                 4930                 4935

att gca aac  agg ata gaa tac aat  gct gct ggg caa gtg  caa aga      16642
Ile Ala Asn  Arg Ile Glu Tyr Asn  Ala Ala Gly Gln Val  Gln Arg
        4940                 4945                 4950

act gaa gct  ggt aat ggt ata ttg  aca gaa tat aca tat  gaa gaa      16687
Thr Glu Ala  Gly Asn Gly Ile Leu  Thr Glu Tyr Thr Tyr  Glu Glu
        4955                 4960                 4965

agt acg cag  cgc tta atg aga aaa  aaa gat tca cgt gag  cta tct      16732
Ser Thr Gln  Arg Leu Met Arg Lys  Lys Asp Ser Arg Glu  Leu Ser
        4970                 4975                 4980

tct gag aag  ata gaa gta ctg cag  gat tat cgt tat gaa  tat gac      16777
Ser Glu Lys  Ile Glu Val Leu Gln  Asp Tyr Arg Tyr Glu  Tyr Asp
        4985                 4990                 4995

cca gta ggt  aat atc ctg tct att  agt aat gac tct gat  ttg gtt      16822
Pro Val Gly  Asn Ile Leu Ser Ile  Ser Asn Asp Ser Asp  Leu Val
        5000                 5005                 5010

cgc ttt ttc  cgc aat cag gcc gtc  tta cca aaa cgt caa  tac aca      16867
Arg Phe Phe  Arg Asn Gln Ala Val  Leu Pro Lys Arg Gln  Tyr Thr
        5015                 5020                 5025

tat gat gct  tta tat caa ctt gtt  tct aat tct gga agg  gaa tct      16912
Tyr Asp Ala  Leu Tyr Gln Leu Val  Ser Asn Ser Gly Arg  Glu Ser
        5030                 5035                 5040

gat gct ctt  cgt cag cat caa tct  ttc tct tca tta ata  aca cct      16957
Asp Ala Leu  Arg Gln His Gln Ser  Phe Ser Ser Leu Ile  Thr Pro
        5045                 5050                 5055

att cca cta  gat gat agt aaa tac  gta aat tat ttt gag  aaa tat      17002
Ile Pro Leu  Asp Asp Ser Lys Tyr  Val Asn Tyr Phe Glu  Lys Tyr
        5060                 5065                 5070

cat tac gat  cgc gct gga aat ttg  ata aaa ctt aac cat  aaa gga      17047
His Tyr Asp  Arg Ala Gly Asn Leu  Ile Lys Leu Asn His  Lys Gly
        5075                 5080                 5085

gcg agt caa  tat aca acg gat att  tat att gat gat act  tca aac      17092
Ala Ser Gln  Tyr Thr Thr Asp Ile  Tyr Ile Asp Asp Thr  Ser Asn
        5090                 5095                 5100
```

-continued

```
aag gga gtc  tgg agg caa aaa gat  gaa ata cca gat att  tca tct     17137
Lys Gly Val  Trp Arg Gln Lys Asp  Glu Ile Pro Asp Ile  Ser Ser
        5105                 5110                 5115

tct ttt gat  aga gca ggc aat caa  aaa gtt tta cgg act  ggg ata     17182
Ser Phe Asp  Arg Ala Gly Asn Gln  Lys Val Leu Arg Thr  Gly Ile
        5120                 5125                 5130

cca ctg gac  tgg gat tca cgt aat  caa tta agt tgt gtc  aat atg     17227
Pro Leu Asp  Trp Asp Ser Arg Asn  Gln Leu Ser Cys Val  Asn Met
        5135                 5140                 5145

gtt tta cgt  gaa aat gaa gat aat  gat tgg gag agc tat  atc cac     17272
Val Leu Arg  Glu Asn Glu Asp Asn  Asp Trp Glu Ser Tyr  Ile His
        5150                 5155                 5160

gat agc aca  gga ata cgc ata gta  aaa tgg aat aac cga  aag aca     17317
Asp Ser Thr  Gly Ile Arg Ile Val  Lys Trp Asn Asn Arg  Lys Thr
        5165                 5170                 5175

aag aat acc  act caa act gat act  act gtc tat tta cct  ggt ttg     17362
Lys Asn Thr  Thr Gln Thr Asp Thr  Thr Val Tyr Leu Pro  Gly Leu
        5180                 5185                 5190

gaa tta cgt  aca cgt caa acg ggt  gaa aaa ttc aca gag  ctc cta     17407
Glu Leu Arg  Thr Arg Gln Thr Gly  Glu Lys Phe Thr Glu  Leu Leu
        5195                 5200                 5205

cat gta gtt  act gca gat acg gaa  ata gca caa gta aga  gtt cta     17452
His Val Val  Thr Ala Asp Thr Glu  Ile Ala Gln Val Arg  Val Leu
        5210                 5215                 5220

cat tgg gag  gat gga acc cag ccg  aat gag gtt tct aat  gat caa     17497
His Trp Glu  Asp Gly Thr Gln Pro  Asn Glu Val Ser Asn  Asp Gln
        5225                 5230                 5235

tat cga tac  agt att aac gat cat  ttg gga tca tcg atg  ttg gag     17542
Tyr Arg Tyr  Ser Ile Asn Asp His  Leu Gly Ser Ser Met  Leu Glu
        5240                 5245                 5250

ttg gat ata  caa ggt caa atc ata  agt aaa gaa gag ttt  tat cct     17587
Leu Asp Ile  Gln Gly Gln Ile Ile  Ser Lys Glu Glu Phe  Tyr Pro
        5255                 5260                 5265

tat ggt gga  aca gcc gtg tgg aca  gcg cgg acg aaa gta  gag gca     17632
Tyr Gly Gly  Thr Ala Val Trp Thr  Ala Arg Thr Lys Val  Glu Ala
        5270                 5275                 5280

aat tat aag  acc ata cgt tat tca  gga aag gaa ctg gat  gct aca     17677
Asn Tyr Lys  Thr Ile Arg Tyr Ser  Gly Lys Glu Leu Asp  Ala Thr
        5285                 5290                 5295

ggt ctc tat  tat tac gga tac agg  tat tat atg cca tgg  ttg ggg     17722
Gly Leu Tyr  Tyr Tyr Gly Tyr Arg  Tyr Tyr Met Pro Trp  Leu Gly
        5300                 5305                 5310

cgc tgg ttg  aat ccg gat cct gcc  ggt aca gta gat gga  atg aac     17767
Arg Trp Leu  Asn Pro Asp Pro Ala  Gly Thr Val Asp Gly  Met Asn
        5315                 5320                 5325

tta tat cga  atg gtc ggg aat aac  cct ata aat tca ata  gat aaa     17812
Leu Tyr Arg  Met Val Gly Asn Asn  Pro Ile Asn Ser Ile  Asp Lys
        5330                 5335                 5340

atg gga ttg  ctc cca gaa aaa cca  aat atc ttt act tta  tcc tct     17857
Met Gly Leu  Leu Pro Glu Lys Pro  Asn Ile Phe Thr Leu  Ser Ser
        5345                 5350                 5355

caa gaa gtt  act gaa att aaa aca  aaa acg gat ctt tct  aac atg     17902
Gln Glu Val  Thr Glu Ile Lys Thr  Lys Thr Asp Leu Ser  Asn Met
        5360                 5365                 5370

aaa ata aat  ctt tct tca ata aaa  atg ggt aat act gat  gca aaa     17947
Lys Ile Asn  Leu Ser Ser Ile Lys  Met Gly Asn Thr Asp  Ala Lys
        5375                 5380                 5385

tgg aat gat  att aga gag aat ttt  gat gat ata gaa act  aat ctt     17992
Trp Asn Asp  Ile Arg Glu Asn Phe  Asp Asp Ile Glu Thr  Asn Leu
```

-continued

```
        5390                5395                5400

gta aag ata  gct ata cat tat gaa  aga gag tat aag gat  aaa tat     18037
Val Lys Ile  Ala Ile His Tyr Glu  Arg Glu Tyr Lys Asp  Lys Tyr
        5405                5410                5415

tca aaa aat  aat tta ggt ccg gca  gtt gca gtt gca tat  aat tta     18082
Ser Lys Asn  Asn Leu Gly Pro Ala  Val Ala Val Ala Tyr  Asn Leu
        5420                5425                5430

aat tca aaa  aaa tat cat gtt gga  ttt aat cac gta gat  ggc aaa     18127
Asn Ser Lys  Lys Tyr His Val Gly  Phe Asn His Val Asp  Gly Lys
        5435                5440                5445

tta cca gaa  aaa aag gat tct aga  ata gca gag agg gtt  cct gat     18172
Leu Pro Glu  Lys Lys Asp Ser Arg  Ile Ala Glu Arg Val  Pro Asp
        5450                5455                5460

caa atg tca  aaa ggt gtt agt aaa  tta tat aaa gac tgg  aca aaa     18217
Gln Met Ser  Lys Gly Val Ser Lys  Leu Tyr Lys Asp Trp  Thr Lys
        5465                5470                5475

gga gca ggt  tcg cat gca gaa gtt  tat gca atc aac agc  gca ctt     18262
Gly Ala Gly  Ser His Ala Glu Val  Tyr Ala Ile Asn Ser  Ala Leu
        5480                5485                5490

tta gat aag  ggg aag aca gat tac  aag gat aca aat cca  gaa gac     18307
Leu Asp Lys  Gly Lys Thr Asp Tyr  Lys Asp Thr Asn Pro  Glu Asp
        5495                5500                5505

ctt ata tta  tat gtt aat aga gtg  aat caa gga aaa aca  aaa cct     18352
Leu Ile Leu  Tyr Val Asn Arg Val  Asn Gln Gly Lys Thr  Lys Pro
        5510                5515                5520

gca gaa ata  agg ccg ttt att act  tgt acg gac tgt gca  tat act     18397
Ala Glu Ile  Arg Pro Phe Ile Thr  Cys Thr Asp Cys Ala  Tyr Thr
        5525                5530                5535

ctg gta gga  cca gaa gtc tta gga  gac ctc tgg gga ggg  ata gcg     18442
Leu Val Gly  Pro Glu Val Leu Gly  Asp Leu Trp Gly Gly  Ile Ala
        5540                5545                5550

agc gta ata  aac caa gat agt gta  cta ggt cta cta aca  cta gaa     18487
Ser Val Ile  Asn Gln Asp Ser Val  Leu Gly Leu Leu Thr  Leu Glu
        5555                5560                5565

ttc ccg gaa  gat aaa att atg gaa  ggt ctt aaa att aag  acg ata     18532
Phe Pro Glu  Asp Lys Ile Met Glu  Gly Leu Lys Ile Lys  Thr Ile
        5570                5575                5580

tct aac att  aaa aag tac tgg gtg  cca aat agc agc gga  caa atg     18577
Ser Asn Ile  Lys Lys Tyr Trp Val  Pro Asn Ser Ser Gly  Gln Met
        5585                5590                5595

gtt gcc taataggagt acttcaaggg aattcattat caattaatgg ttcaagcaaa     18633
Val Ala

aacgcattaa ttcacgtagc tatttaacag gtaatttcta agaaattgaa catcgttatt  18693

taatctaaat aaattatcat tcgaaccaat gaaatcttta atcacgattc acaatgtata  18753

tatattctta aacgaggcag tatactcact ttgttatgtt ctatgtgtct gttcttcaat  18813

atattttcat ggtaaaaaca tcgtttaatc ttttttttaaa aggtgaaaga aagtgctgtg  18873

tgtaatatag tatattacca atattgaaac cgttatatgt ttgtagcgta ccgattgaag  18933

aaggtagcta ctcttcaaca gagactatat ataaaagatt taaataaatt cactaatgaa  18993

gactgtgata cagatttatc atatttgaaa ttttaataga cccattatga taaagatgcg  19053

tgtaactata catgtgaatt ccctttaact tatttaaatt aaatatagct attgaattac  19113

ccacaaaagt agttcatttt gtatccactt tcttgtctta acaaatggac atgaaagtgg  19173

atattttta aaatgaagac aagaatgatt ctgcttaaaa ttcaatctat aaaaggagcc  19233

gggtaatctt tcatgtataa accactaatt accaacgcta gtaagacgtt tggaaataat  19293
```

-continued

```
agatggatcg cgtatagttc taagctacaa cgcgaagttt ttttatttag tgatttagaa  19353

tacgaacatt ggttaattat cgaatcaaac ccaacaatta tagatttttg tgaacaacct  19413

ttactaatga atgcaaatat aaatggcaaa ttaatggcct ctattattga tatgtgggtg  19473

aaatatgata ctggccacga agaattcata gaaattaaat attcatcaga cttaacaaaa  19533

caaagagtaa ttaatcaaat tgctattcaa aaacactggt gtaatgaaca tggattccaa  19593

catcatgtaa gaacagaaga acatattcga acaaatagaa tgttactttc aaacttaaaa  19653

atacttgtaa aaggacataa gcaacaaaaa catcaattag ataccgatag gtatctaatt  19713

atgaaaatcc taaaaggtgc cacagcaaaa ataccactaa ctttttttgat tcaagaaaca  19773

aaaatccctc aaaacagatt attcctttca attggacaaa tgattttaaa tggtgaagta  19833

tattcaaaca tatcgcaaca atattatggg ttaaatacgg aggtgtgggt tg atg      19888
                                                          Met
                                                          5600

tct aaa agg ttt tta  gaa aat tta aat gta  gaa gaa cac ttt tta      19933
Ser Lys Arg Phe Leu  Glu Asn Leu Asn Val  Glu Glu His Phe Leu
                5605                 5610                 5615

gat att tct aat tgg  cct caa gta tta tac  gaa aac ctt aac gaa      19978
Asp Ile Ser Asn Trp  Pro Gln Val Leu Tyr  Glu Asn Leu Asn Glu
                5620                 5625                 5630

gaa gaa aaa gct att  ttt tta aat cga aaa  caa gca gtt gat tta      20023
Glu Glu Lys Ala Ile  Phe Leu Asn Arg Lys  Gln Ala Val Asp Leu
                5635                 5640                 5645

ttc atg aca aca gaa  aca aaa ata tca gat  ata gaa cta caa ttt      20068
Phe Met Thr Thr Glu  Thr Lys Ile Ser Asp  Ile Glu Leu Gln Phe
                5650                 5655                 5660

gga ttt ggc agg agg  cac atc tat aga ttt  gta aaa aga tgt tta      20113
Gly Phe Gly Arg Arg  His Ile Tyr Arg Phe  Val Lys Arg Cys Leu
                5665                 5670                 5675

gaa aag gac gaa ttt  gaa atg ata atg ggt  tat aga gcc cta atc      20158
Glu Lys Asp Glu Phe  Glu Met Ile Met Gly  Tyr Arg Ala Leu Ile
                5680                 5685                 5690

cct tat aaa aga tta  aaa aat tac cat agg  aac tca ttt ccg atg      20203
Pro Tyr Lys Arg Leu  Lys Asn Tyr His Arg  Asn Ser Phe Pro Met
                5695                 5700                 5705

gct aat aca gca aag  gaa aat ttc tct ggt  gct ttt agt tta tta      20248
Ala Asn Thr Ala Lys  Glu Asn Phe Ser Gly  Ala Phe Ser Leu Leu
                5710                 5715                 5720

ctc gat acg tat ccg  tcg cta aga gaa atg  ata ata aat tct tat      20293
Leu Asp Thr Tyr Pro  Ser Leu Arg Glu Met  Ile Ile Asn Ser Tyr
                5725                 5730                 5735

ttt aat aga aat agc  aaa tat aaa gtt aat  gat cca att att aat      20338
Phe Asn Arg Asn Ser  Lys Tyr Lys Val Asn  Asp Pro Ile Ile Asn
                5740                 5745                 5750

att aaa tat ttg cat  aaa aag ttt gtt gac  gag tgt cga cgt ttg      20383
Ile Lys Tyr Leu His  Lys Lys Phe Val Asp  Glu Cys Arg Arg Leu
                5755                 5760                 5765

gga ata aaa aca aat  gag tat cca ctt aac  aca aaa acc tta gca      20428
Gly Ile Lys Thr Asn  Glu Tyr Pro Leu Asn  Thr Lys Thr Leu Ala
                5770                 5775                 5780

aaa aag tca ctg gag  cga ttt gta aaa tcc  tta tct aaa tct cat      20473
Lys Lys Ser Leu Glu  Arg Phe Val Lys Ser  Leu Ser Lys Ser His
                5785                 5790                 5795

ttt att gac gtt gca  aaa agg aat gga gag  caa gca ttt atg att      20518
Phe Ile Asp Val Ala  Lys Arg Asn Gly Glu  Gln Ala Phe Met Ile
                5800                 5805                 5810

gca aaa aat acc gga  aat gga aac aaa aat  aat cct atg act ata      20563
```

-continued

```
Ala Lys Asn Thr Gly  Asn Gly Asn Lys Asn  Asn Pro Met Thr Ile
                5815                 5820                 5825

agg ccc ctt gaa cgt  gtt gaa ttt gat ggt  cat aga att gat gca      20608
Arg Pro Leu Glu Arg  Val Glu Phe Asp Gly  His Arg Ile Asp Ala
                5830                 5835                 5840

tct ata gcc ata att  ttc aaa aca cca gaa  ggt gat gag ata gta      20653
Ser Ile Ala Ile Ile  Phe Lys Thr Pro Glu  Gly Asp Glu Ile Val
                5845                 5850                 5855

gaa gtg atg aat cgt  att tgg ctt ctc gcc  att att gat gtt gct      20698
Glu Val Met Asn Arg  Ile Trp Leu Leu Ala  Ile Ile Asp Val Ala
                5860                 5865                 5870

acg aga act gtg cta  gga tat cac ctt tgt  tta aat aaa gaa tat      20743
Thr Arg Thr Val Leu  Gly Tyr His Leu Cys  Leu Asn Lys Glu Tyr
                5875                 5880                 5885

tcc tca gat gat gtt  cta atg tgt att cga  aat gca att atc cct      20788
Ser Ser Asp Asp Val  Leu Met Cys Ile Arg  Asn Ala Ile Ile Pro
                5890                 5895                 5900

tgg aac ccc aaa aaa  tta acc att gag ggc  tta aaa tat tct cca      20833
Trp Asn Pro Lys Lys  Leu Thr Ile Glu Gly  Leu Lys Tyr Ser Pro
                5905                 5910                 5915

ata gca aac ttt gtt  tct aat gct atc cca  gaa gca agc tat ggt      20878
Ile Ala Asn Phe Val  Ser Asn Ala Ile Pro  Glu Ala Ser Tyr Gly
                5920                 5925                 5930

ata tgg gat gaa ttt  tgt tat gac aat gca  aaa gca aat cta gca      20923
Ile Trp Asp Glu Phe  Cys Tyr Asp Asn Ala  Lys Ala Asn Leu Ala
                5935                 5940                 5945

aaa aat gta caa aat  aag ctt                                       20944
Lys Asn Val Gln Asn  Lys Leu
                5950


<210> SEQ ID NO 2
<211> LENGTH: 1088
<212> TYPE: PRT
<213> ORGANISM: Bacillus thuringiensis EG5858

<400> SEQUENCE: 2

Val Ser Thr Thr Glu Asn Asn Val Gly Ile Phe Gln Ile Gly Thr Asp
1               5                   10                  15

Arg Leu Thr Val Thr Leu Asn Gln Ser Gly Tyr Gln Thr Val Phe Asp
            20                  25                  30

Ile Thr Ser Glu Ser Tyr Leu Glu Phe Glu Glu Asn Asn Pro Glu Ile
        35                  40                  45

Pro Ser Ser Asp Ala Lys Glu Ile Tyr Lys Leu Ala Val Lys Arg Thr
    50                  55                  60

Glu Asn Leu Arg Met Leu Phe Lys Ala Trp Gln Leu His Asn Asp Pro
65                  70                  75                  80

Ile Phe Lys Asp Ile Pro Lys Leu Ser Ser Asn Ile Gly Met Gln Gly
                85                  90                  95

Met Arg Ser Ala Leu Lys Arg Ser Leu Gly Gly Gly Ala Asn Phe Glu
            100                 105                 110

Asp Leu Phe Pro Glu Arg Ser Leu Glu Gly Tyr Ala Glu Ser Ser Ser
        115                 120                 125

Ile Gln Ser Leu Phe Ser Pro Gly Arg Tyr Leu Thr Val Leu Tyr Lys
    130                 135                 140

Ile Ala Arg Gln Leu His Ser Thr Glu Asp Lys Leu His Ile Asp Asn
145                 150                 155                 160

Arg Arg Pro Asp Leu Gln Ser Leu Val Leu Ser Glu Asp Asn Met Asn
                165                 170                 175
```

-continued

```
Lys Glu Val Ser Ser Leu Asp Ile Leu Leu Asp Val Leu Gln Pro Glu
            180                 185                 190

Asp Phe Asn Thr Leu Lys Thr Leu Lys Asp Thr Tyr Tyr Pro Met Asn
        195                 200                 205

Leu Pro Tyr Asp Asp Asp Leu Thr Gln Ile Asn Ala Val Ala Glu Ala
    210                 215                 220

His Ser Thr Asn Leu Ile Gly Ile Trp Asp Ile Leu Leu Asp Lys Gln
225                 230                 235                 240

Gln Lys Ser Ile Leu Gln Asp Val Asn Thr Phe Pro Arg Ile Ser Lys
                245                 250                 255

Lys Arg Arg Asp Ser Leu Ser Asn Thr Pro Glu Ser Leu Glu Leu Ile
            260                 265                 270

Glu Gly Glu Glu Phe Tyr Leu Glu Ala Lys Gly Lys Gln Ile Tyr Phe
        275                 280                 285

Ala Asn Val Met Glu Thr Ala Tyr Thr Ile Ser Thr His Ile Thr Val
    290                 295                 300

Gly Lys Pro Gln Ala Ala Ala Thr Ala Pro Ala Lys Phe Gln Leu Ile
305                 310                 315                 320

Tyr Asp Ile Lys Arg Gly Asp Tyr Phe Leu Arg Val Ala Glu Asn Ile
                325                 330                 335

Ser Ile Asp Gly Lys Ser Leu Lys Asp Cys Tyr Leu Thr Ser Asp Asn
            340                 345                 350

Gly Glu His Asn Gly Lys Lys Gly Phe Tyr Cys Leu Met Lys Asn Pro
        355                 360                 365

Arg Asn Asn Phe Pro Val Lys Ile Glu Arg Leu Thr Asp Thr Ser Ile
    370                 375                 380

Arg Ile Phe Val Pro Gln Ser Gly Tyr Trp Gly Pro Gly Glu Thr Val
385                 390                 395                 400

Ala Ser His Trp Glu Asn Pro Leu Ala Leu Asn Leu Asp Leu Ala Glu
                405                 410                 415

Ala Leu Thr Phe Thr Leu Lys Lys Asn Glu Thr Gly Gly Glu Thr Ile
            420                 425                 430

Ser Val Ser Glu Val Met Pro Pro Val Ala Asp Thr Thr Pro Ser Pro
        435                 440                 445

Pro Ala Arg Glu Thr Leu Ser Leu Thr Pro Asn Ser Phe Gln Leu Leu
    450                 455                 460

Val Asn Pro Asn Pro Thr Val Glu Asp Ile Ala Asn His Tyr Asp Val
465                 470                 475                 480

Lys Ala Thr Lys Asn Leu Asp Ser Thr Asp Leu Thr Thr Val Leu Asn
                485                 490                 495

Asn Val Asp Asn Phe Cys Leu Lys Thr Ser Leu Ser Phe Asn Lys Leu
            500                 505                 510

Leu Glu Leu Thr Met Gln Lys Asp Tyr Gln Thr Lys Ser Gly Glu Tyr
        515                 520                 525

Lys Ser Arg Phe Leu Lys Phe Ser Ser Thr Glu Asn Val Pro Val Ser
    530                 535                 540

Thr Tyr Gly Ala Ala Phe Leu Thr Gly Thr Glu Gln Ile Pro Leu Trp
545                 550                 555                 560

Val Lys Gln Tyr Asn Gly Lys Gly Asn Ala Thr Asn Thr Pro Val Leu
                565                 570                 575

Asn Phe Thr Ala Asp Asn Val Val Asp Leu Ala Gly Arg Ala Glu Lys
            580                 585                 590
```

-continued

```
Leu Val Arg Leu Glu His Ser Thr Asp Leu Ser Phe Glu Gln Leu Asp
        595                 600                 605

Trp Ile Ile Thr Asn Ala Ser Lys Ser Ile Phe Glu His Gly Lys Asn
    610                 615                 620

Ile Ile Leu Asp Lys Pro Val Leu Gly Ala Ile Ala Glu Tyr Lys Lys
625                 630                 635                 640

Phe Asn Asn His Tyr Gly Ile Thr Ser Asp Met Phe Val Thr Phe Ile
                645                 650                 655

Gly Glu Ile Asn Thr Tyr Ala Glu Glu Gly Lys Asn Ser Phe Tyr Gln
            660                 665                 670

Asp Thr Phe Ser Asn Val Asp Gly Thr Thr Val Pro Leu Gly Ala Ser
        675                 680                 685

Leu Gln Phe Ala Ile Asp Lys Gln Gly Leu Tyr Glu Ser Ile Cys Cys
    690                 695                 700

Gly Ala Met Gly Val Thr Ala Asp Glu Phe Ser Arg Ile Gly Ala Tyr
705                 710                 715                 720

Cys Phe Gly Asp Ala Thr Gln Gln Ile Thr Ala Asp Glu Ala Ser Ile
                725                 730                 735

Ala Gln Leu Tyr Arg Leu Gly Lys Ile Pro Gln Met Leu Gly Leu Ser
            740                 745                 750

Phe Arg Glu Ala Glu Leu Leu Trp Lys Thr Met Ala Ser Gly Lys Asn
        755                 760                 765

Thr Leu Leu Arg Asn Ile Gly Ala Ser Pro His Ser Leu Gln Thr Leu
    770                 775                 780

Asp Ile Ile Arg Arg Thr Glu Val Leu Leu Asp Trp Met Asp Thr His
785                 790                 795                 800

Gln Leu Asp Val Val Ser Leu Gln Val Met Ile Thr Asn Gln Tyr Ser
                805                 810                 815

Ser Thr Ala Thr Pro Glu Leu Tyr Asn Phe Leu Lys Asn Val Tyr Gln
            820                 825                 830

Ser Thr Ile Ser Val Glu Arg Thr Ser Arg Ile Ser Asn His Lys Ser
        835                 840                 845

Met Pro Ala Glu Lys Met Ser Arg Ala Leu Ala Ala Gly Phe Asn Leu
    850                 855                 860

Lys Val Asn Val Met Gly Lys Val Met Lys Trp Met Asp Lys Ala Gln
865                 870                 875                 880

Pro Thr Phe Met Ser Gln Asp Phe Tyr Thr Lys Leu His Trp Tyr Phe
                885                 890                 895

Ser Thr Asp His Glu Asp Glu Leu Thr Thr Leu Glu Lys His Pro Glu
            900                 905                 910

Leu Leu Glu Trp Cys Gln Lys Val Ser Gln Tyr Val Leu Ile Val Arg
        915                 920                 925

Trp Ser Gly Leu Asn Glu Gln Glu Leu Thr Met Met Ile Glu His Pro
    930                 935                 940

Asp Trp Leu Leu Glu Gly Tyr Asp Thr Val Pro Gln Pro Ser Leu His
945                 950                 955                 960

Leu Leu Leu Ile Leu Ser Arg Leu Lys Glu Trp Glu Gln Arg Val Gln
                965                 970                 975

Val Ser Ser Asp Glu Ala Ile Arg Tyr Phe Ala Gln Ala Asn Ser Lys
            980                 985                 990

Asn Ile Asn Ser Asp Ala Ala Val  Lys Leu Leu Ala His  Ile His Gly
        995                 1000                 1005

Trp Asn  Glu Glu Gly Thr Ser  Ser Met Asn Asn Tyr  Leu Phe Gly
```

```
    1010                1015                1020

Asp Asp  Ser Tyr Pro Lys Asn  Phe Glu Gln Val Phe  Thr Leu Glu
    1025                1030                1035

Ser Trp  Val Asn Leu Gly Lys  Gln Leu Asn Val Gly  Ser Arg Thr
    1040                1045                1050

Leu Gly  Glu Leu Val Asp Leu  Val Glu Glu Asn Glu  Thr Ala Glu
    1055                1060                1065

Ser Thr  Asp Leu Ile Ile Ser  Val Ala Gln Ala Leu  Met Ala Thr
    1070                1075                1080

Val Gln  Ser Glu Lys
    1085


<210> SEQ ID NO 3
<211> LENGTH: 1205
<212> TYPE: PRT
<213> ORGANISM: Bacillus thuringiensis EG5858

<400> SEQUENCE: 3

Met Ser Asn Ser Thr Val Leu Gln Ser Ile Lys Glu Ser Arg Arg Asp
1               5                   10                  15

Val Leu Val Asp His Tyr Ile Ala Asn Asn Val Pro Lys Asp Leu Thr
            20                  25                  30

Asp Lys Ile Thr Asp Ala Glu Ser Leu Tyr Glu Tyr Leu Leu Leu Asp
        35                  40                  45

Thr Lys Ile Ser Asp Leu Val Lys Thr Ser Pro Ile Ala Glu Ala Ile
    50                  55                  60

Ser Ser Val Gln Leu Tyr Ile Asn Arg Cys Ile Gln Gly Tyr Glu Gly
65                  70                  75                  80

Glu Leu Thr Thr Gln Ser Lys Ser His Phe Ala Pro Gly Lys Phe Leu
                85                  90                  95

Ser Asn Trp Asp Asn Tyr Asn Lys Arg Tyr Thr Thr Trp Ser Gly Lys
            100                 105                 110

Glu Arg Leu Lys Tyr Tyr Ala Gly Ser Tyr Ile Asp Pro Ser Ser Arg
        115                 120                 125

Tyr Asn Lys Thr Asn Leu Phe Lys Asn Leu Glu Gln Ser Ile Ser Gln
    130                 135                 140

Gly Arg Leu Thr Glu Glu Ser Ile Lys Asn Ala Leu His Asn Tyr Leu
145                 150                 155                 160

Asp Glu Tyr Glu Thr Leu Ala Asn Leu Glu Tyr Ile Ser Val Asn Lys
                165                 170                 175

Gly Asp Gly Glu Asp Ala Glu Ser Val Leu Phe Phe Val Gly Arg Thr
            180                 185                 190

Gln Thr Phe Pro Tyr Glu Tyr Tyr Trp Arg Ser Leu Ile Leu Lys Lys
        195                 200                 205

Asn Ser Asn Asn Ile Leu Ile Pro Glu Lys Trp Thr Gln Trp Glu Lys
    210                 215                 220

Ile Thr Ala Asn Ile Gly Glu Ala Val Asp Ser Tyr Val Val Ile Tyr
225                 230                 235                 240

Cys Tyr Lys Lys Arg Leu His Val Gln Trp Ser Ser Ser Glu Lys Lys
                245                 250                 255

Gln Asn Ile Asn Lys Glu Ser Ile Asp Ile Gln Tyr Leu Asn Asp Trp
            260                 265                 270

Val Met Asn Ser Ser Gly Val Trp Ser Ala Phe Gln Lys Ser Pro Phe
        275                 280                 285
```

-continued

```
Lys Ser Phe Asp Tyr Ile Pro Asn Ser Ile Thr Gly Phe Ser Lys Glu
    290                 295                 300

Asn Ile His Ile Val Asp Asn Lys Val Ile Cys Asp Asp Pro Asn Ser
305                 310                 315                 320

Ile Lys Val Lys Val Thr Ser Leu Pro Gly Asn Arg Val Arg Ile Tyr
                325                 330                 335

Phe Glu Lys Ile Tyr Asn Ser Glu Leu Ser Gly Ser Thr Leu Ser Phe
            340                 345                 350

Trp Pro Ala Leu Ser Ser Asp Pro Glu Ile Asn Glu Gly Glu Gln Lys
        355                 360                 365

Asp Tyr Ile Ile Asp Phe Asp Ser Glu Pro Tyr Tyr Gly Leu Leu Val
    370                 375                 380

Arg Leu Asn Phe Asp Gln Lys Glu Tyr Tyr Phe Ser Val Leu Tyr Tyr
385                 390                 395                 400

Pro Ser Pro Tyr Gln Glu Leu Tyr Gly Ser Ile Ile Asn Asp Gln Phe
                405                 410                 415

Ile Pro Pro Ser Asn Ser Lys Ile Ile Glu Pro Ile Ser Leu Thr Leu
            420                 425                 430

Lys Asn Asn Ile Asp Leu Ala Asn Leu Cys Glu Asn Ser Ile Asp Thr
        435                 440                 445

Leu Phe Glu Tyr Thr Val Gln Gly Glu Leu Gly Asp Thr Ile Ala Phe
    450                 455                 460

Tyr Gly Pro Tyr Gly Ile Tyr Leu Trp Glu Ile Phe Phe Tyr Ile Pro
465                 470                 475                 480

Phe Leu Ile Ala Val Arg Leu Leu Ile Glu Gln Arg Tyr Glu Leu Val
                485                 490                 495

Glu Arg Trp Tyr Lys Phe Ile Phe Asn Ser Ala Gly Tyr Arg Asp Glu
            500                 505                 510

Asn Gly Asn Leu Leu Lys Asp Lys Asn Gly Asn Val Arg Tyr Trp Asn
        515                 520                 525

Val Val Pro Leu Gln Glu Asp Thr Glu Trp Asp Glu Thr Leu Ser Leu
    530                 535                 540

Ala Ile Thr Asp Pro Asp Glu Ile Ala Met Ala Asp Pro Met Gln Tyr
545                 550                 555                 560

Lys Leu Ala Ile Phe Ile His Thr Leu Asp Phe Leu Ile Asn Arg Gly
                565                 570                 575

Asp His Ala Tyr Arg Met Leu Glu Arg Asp Thr Leu Thr Glu Ala Lys
            580                 585                 590

Met Tyr Tyr Ile Gln Ala Lys Gln Ile Leu Gly Pro Arg Pro Glu Ile
        595                 600                 605

Arg Ile Asn Asn Ser Trp Asp Asn Pro Thr Leu Gln Ser Glu Ala Gly
    610                 615                 620

Ala Met Thr Ala Glu Pro Thr Arg Asn Asn Leu Asp Ile Thr Pro Ile
625                 630                 635                 640

Met Gln Leu Gln Ala Phe Leu Lys Ser Glu Asn Gly His Phe Leu Ser
                645                 650                 655

Pro Tyr Asn Asp Glu Leu Leu Ala Phe Trp Asp Lys Ile Glu Leu Arg
            660                 665                 670

Leu Tyr Asn Leu Arg His Asn Leu Ser Leu Asp Gly Gln Pro Leu Asn
        675                 680                 685

Leu Pro Leu Phe Val Glu Pro Met Asn Pro Arg Asp Leu Gln Ile Gln
    690                 695                 700

Tyr Ser Thr Gly Asp Gly Met Gly Gly Ser Val Ala Ser Ser Gln Ser
```

-continued

```
705                 710                 715                 720

Ser Gln Ser Ile Tyr Arg Phe Pro Ile Val Ile Asp Lys Ala Arg Thr
                725                 730                 735

Ala Val Asn Ser Val Ile Gln Phe Gly Ser Ala Leu Glu Asn Ala Phe
            740                 745                 750

Ala Lys Gln Asp Thr Glu Ala Met Thr Leu Leu Leu Gln Ser Gln Gln
        755                 760                 765

Gln Val Ile Leu Gln Gln Thr Arg Asp Met Gln Glu Lys Asn Leu Asp
    770                 775                 780

Ser Leu Gln Ala Ser Leu Glu Ala Thr Thr Ile Ala Lys Ala Ser Ala
785                 790                 795                 800

Glu Ser Thr Lys Thr His Tyr Ala Gly Leu Val Glu Asn Trp Met Ser
                805                 810                 815

Asp Asn Glu Thr Ser Ser Leu Lys Leu Arg Ser Asp Ala Gly Ile Ile
            820                 825                 830

His Thr Ser Ser Glu Val Ala Met Thr Ile Ala Ala Ala Leu Asp Met
        835                 840                 845

Ala Pro Asn Val Phe Gly Met Ala Val Gly Gly Ser Arg Trp Gly Ala
    850                 855                 860

Ala Ser Thr Ala Val Ala Gln Gly Leu Gln Ile Ser Ala Asn Val Met
865                 870                 875                 880

Glu Gln Thr Ala Asn Ile Met Asp Ile Ser Glu Ser Tyr Arg Arg Arg
                885                 890                 895

Arg Glu Asp Trp Met Leu Gln Arg Asp Ala Ala Glu Ala Glu Glu Ser
            900                 905                 910

Gln Leu Asn Leu Gln Ile Lys Ala Leu Gln Glu Gln Ile Asn Met Ala
        915                 920                 925

Arg Lys Gln Ile Phe Leu Ser Glu Thr Glu Gln Ala His Ala Gln Ala
    930                 935                 940

Ile Tyr Gln Leu Gln Cys Thr Arg Phe Ser Ser Gln Ala Leu Tyr Asn
945                 950                 955                 960

Trp Met Val Gly Arg Leu Ser Ser Leu Tyr Tyr Gln Met Tyr Asp Ala
                965                 970                 975

Thr Leu Ser Leu Cys Phe Met Ala Lys Asn Ala Leu Glu Lys Glu Leu
            980                 985                 990

Gly Lys Asp Lys Thr Thr Gly Met  Phe Thr Leu Pro Ala  Trp Asp Asp
        995                 1000                1005

Leu Tyr  Gln Gly Leu Leu Ala  Gly Glu Met Leu Met  Val Glu Leu
    1010                1015                1020

Gln Lys  Leu Glu Asn Leu Trp  Leu Glu Glu Asn Lys  Trp Gly Met
    1025                1030                1035

Glu Ala  Val Lys Thr Val Ser  Leu Asp Thr Leu Ile  Arg Lys Lys
    1040                1045                1050

Asn Pro  Glu Phe Ala Phe Val  Asp Leu Val Gln Glu  Val Leu Ser
    1055                1060                1065

Gly Lys  Ile Pro Glu Gly Val  Ser Gly Ile Glu Val  Lys Leu Gln
    1070                1075                1080

Asn Asn  Ile Phe Ser Ala Ser  Leu Asp Leu Ser Ser  Leu Gly Leu
    1085                1090                1095

Glu Asn  Ser Tyr Asn Leu Lys  Glu Lys Asn Arg Lys  Ile Lys Asn
    1100                1105                1110

Leu Ser  Val Thr Leu Pro Ala  Leu Leu Gly Pro Tyr  Gln Asp Val
    1115                1120                1125
```

```
Glu Ala  Thr Leu Ser Leu Gly  Gly Glu Thr Val Thr  Leu Ser His
    1130                 1135                 1140

Gly Val  Asp Asp Ser Gly Leu  Phe Ile Thr Asp Phe  Asn Asp Ser
    1145                 1150                 1155

Arg Phe  Leu Pro Phe Glu Gly  Met Asn Leu Leu Ser  Gly Thr Leu
    1160                 1165                 1170

Thr Leu  Ala Ile Phe His Thr  Gly Lys Asp Gly Asp  Gln Arg Ser
    1175                 1180                 1185

Leu Leu  Glu Ser Leu Asn Asp  Val Ile Phe His Ile  Arg Tyr Val
    1190                 1195                 1200

Met Lys
    1205


<210> SEQ ID NO 4
<211> LENGTH: 1458
<212> TYPE: PRT
<213> ORGANISM: Bacillus thuringiensis EG5858

<400> SEQUENCE: 4

Met Ser Gln Thr Asn Thr Asn Val Gly Leu Phe Ser Pro Ser Leu Pro
1               5                   10                  15

Lys Gly Gly Gly Ser Ile Lys Gly Met Glu Gly Ser Val Thr Ala Pro
            20                  25                  30

Gly Ser Asp Gly Met Ala Arg Phe Asn Val Pro Leu Pro Val Thr Pro
        35                  40                  45

Gly Arg Thr Ile Thr Pro Asp Val Asn Leu Ser Tyr Ser Ser Gly Asn
    50                  55                  60

Gly Asn Gly Pro Phe Gly Met Gly Trp His Met Gly Phe Met Ser Ile
65                  70                  75                  80

Arg Arg Arg Thr Asn Thr Gly Ile Pro Ser Tyr Lys Ser Gly Asp His
                85                  90                  95

Phe Ile Gly Pro Asp Gly Glu Val Leu Val Pro Glu Ser Asp Glu Asn
            100                 105                 110

Gly Gln Val Ile Thr Arg Gln Thr Asp Thr Thr Ala Gln Gly Ile Ser
        115                 120                 125

Leu Gly Glu Pro Phe Ile Val Thr Arg Tyr Phe Pro Arg Ile Glu Ser
    130                 135                 140

Asn Phe Asn Leu Ile Glu Tyr Trp Glu Ala Lys Glu Asp Ser His Thr
145                 150                 155                 160

Ser Pro Phe Trp Leu Ile His Ser Ala Asp Gly Ile Leu His Cys Phe
                165                 170                 175

Gly Lys Thr Val Gln Ala Lys Ile Ala Ser Pro Asp Asp Pro Thr Lys
            180                 185                 190

Ile Ala Glu Trp Leu Leu Glu Glu Ser Val Ser Pro Phe Gly Glu His
        195                 200                 205

Val Tyr Tyr Gln Tyr Lys Glu Glu Asp Asn Ile Gly Ile Asn Leu Lys
    210                 215                 220

Gln Asp Thr His Gln Tyr Gly Gly Asn Arg Tyr Leu Lys Thr Ile Arg
225                 230                 235                 240

Tyr Gly Asn Lys Val Ala Tyr His Ser Leu Tyr Leu Trp Asn Gly Glu
                245                 250                 255

Ile Pro Met Asp Ser Gln Trp Leu Tyr Phe Val Met Leu Asp Tyr Gly
            260                 265                 270

Glu Asn Asp Thr Ser Val Asn Gly Ser Pro Gln Tyr Thr Tyr Gln Gly
```

-continued

```
        275                 280                 285

Glu Trp Leu Ala Arg Ala Asp Cys Phe Ser Arg Tyr Glu Tyr Gly Phe
    290                 295                 300

Glu Thr Arg Thr Cys Arg Leu Cys Arg Gln Val Leu Met Phe His Asn
305                 310                 315                 320

Phe Thr Glu Leu Asn Glu Glu Pro Thr Leu Ile Trp Lys Met Gln Phe
                325                 330                 335

Glu Tyr Asp Glu Asn Pro Ala Val Ser Met Leu Thr Ala Val Gln Gln
            340                 345                 350

Leu Ala Tyr Glu Thr Asp Gly Lys Pro Leu Ser Met Pro Pro Leu Glu
        355                 360                 365

Phe Asp Tyr Thr Pro Phe Glu Ile His Gln Pro Ile Asp Trp Gln Pro
    370                 375                 380

Phe Leu Pro Ala Pro Glu Leu Asn Asn Gly Glu Gln Tyr Gln Ile Val
385                 390                 395                 400

Asp Leu Tyr Gly Glu Gly Ile Pro Gly Leu Leu Tyr Arg Asp Lys Ser
                405                 410                 415

His Trp His Tyr Arg Ser Pro Val Arg Ser Asp Thr Leu Asp Gly Ile
            420                 425                 430

Thr Tyr Glu Ser Trp Lys Ser Leu Pro Gln Ile Pro Val Asn Val Gln
        435                 440                 445

Asn Gly Met Leu Leu Asp Met Asn Gly Asp Gly Tyr Leu Glu Trp Leu
    450                 455                 460

Ile Ala Gln Ser Gly Val Ile Gly Ser Tyr Thr Met Asn Pro Asp Lys
465                 470                 475                 480

Thr Trp Ser Asn Phe Val Pro Phe Lys Ala Leu Pro Thr Glu Phe Phe
                485                 490                 495

His Pro Lys Ala Gln Leu Ser Asn Val Thr Gly Ser Gly Leu Pro Asp
            500                 505                 510

Leu Val Met Ile Gly Pro Lys Ser Val Arg Phe Tyr Ala Gly Glu Glu
        515                 520                 525

Ser Gly Phe Lys Arg Ser Arg Glu Val Trp Gln Lys Ala Gly Ile Thr
    530                 535                 540

Leu Pro Ile Glu Gly Leu Asn Glu Lys Glu Leu Ile Ala Phe Ser Asp
545                 550                 555                 560

Met Leu Gly Ser Gly Gln Ser His Leu Val Arg Ile Arg His Asp Gly
                565                 570                 575

Val Thr Cys Trp Pro Asn Met Gly Gln Gly Ile Phe Gly Glu Pro Leu
            580                 585                 590

Val Leu Pro Gly Phe Thr Ile Asn Glu Arg Asp Phe Asp Pro Lys Arg
        595                 600                 605

Val Tyr Leu Ala Asp Leu Asp Gly Ser Gly Thr Ser Asp Val Ile Tyr
    610                 615                 620

Ala Ser His Asp Ala Leu His Ile Tyr Gln Asn Leu Ser Gly Asn Ser
625                 630                 635                 640

Phe Ala Asp Pro Val Gln Ile Pro Leu Pro Ala Gly Val His Phe Asp
                645                 650                 655

Asn Leu Cys Arg Leu Gln Pro Ala Asp Ile Ser Gly Arg Gly Ile Ser
            660                 665                 670

Asn Leu Val Leu Asn Val Pro Tyr Ile Ser Pro Arg Ser Trp Tyr Leu
        675                 680                 685

Asp Leu Cys Ser Ile Lys Pro Tyr Leu Leu Lys Ser Thr Ser Asn Asn
    690                 695                 700
```

-continued

```
Leu Gly Ala Ser Asn Glu Phe Phe Tyr Arg Ser Ser Ala Gln Tyr Trp
705                 710                 715                 720

Leu Asp Glu Lys Gln Ser Asp Ser Ser Val Val Cys Thr Leu Pro Phe
                725                 730                 735

Pro Ile Asn Val Ile Ser Cys Ile Gln Thr Leu Asp Glu Ile Ser Gly
            740                 745                 750

Ser Thr Lys Ile Gln Glu Tyr Thr Tyr Arg Asn Gly Val Tyr Asp Arg
        755                 760                 765

Met Glu Lys Glu Phe Ala Gly Phe Gly Tyr Ile Val Thr Lys Val Glu
    770                 775                 780

Glu Arg Asp Tyr Glu Gly Ser Ile Ser Lys Asn Thr Gln Pro Ile Leu
785                 790                 795                 800

Thr Arg Ser Trp Tyr His Thr Gly Gln Gln Glu Asp Asp Thr Arg Thr
                805                 810                 815

Phe Thr Gln Ser Trp Lys Gly Asp Pro Ile Ala Phe His Leu Lys Pro
            820                 825                 830

Ser Arg Phe Thr Thr Phe Asp Leu Asn Val Thr Lys Asp Val Pro Leu
        835                 840                 845

Asp Ser Leu Asn Glu Arg Gln Glu Tyr Trp Leu Tyr Arg Ser Leu Lys
    850                 855                 860

Gly Met Pro Leu Arg Thr Glu Ile Phe Arg Gly Asp Met Leu Glu Ser
865                 870                 875                 880

Ser Pro Tyr Leu Val Glu Ser Tyr Arg Tyr Gln Val Arg Leu Val Gln
                885                 890                 895

Ser Thr Asp Ser Glu Cys Val Val Leu Pro Leu Gln Leu Glu Gln Leu
            900                 905                 910

Thr Tyr Asn Tyr Glu Gln Ile Ser Ser Asp Pro Gln Cys Thr Gln Gln
        915                 920                 925

Ile Gln Gln Phe Phe Asp Glu Tyr Gly Ser Ser Thr Gln Ser Val Thr
    930                 935                 940

Ile His Tyr Pro Arg Arg Glu Gln Pro Asn Glu Asn Pro Tyr Pro Asp
945                 950                 955                 960

Thr Leu Pro Asp Thr Ser Trp Ser Ser Ser Tyr Asp Ser Gln Gln Met
                965                 970                 975

Leu Leu Arg Phe Thr Arg Gln Arg Glu Lys Ala Tyr His Leu Thr Asn
            980                 985                 990

Ser Glu Asn Trp Arg Leu Gly Ile  Pro His Gln Asn Arg  Leu Asp Ala
        995                 1000                1005

Phe Val  Tyr Pro Ala Glu Ser  Val Pro Asn Glu Gly  Ile Ser Thr
    1010                1015                1020

Glu Leu  Leu Gly Asp Asp Gly  Thr Leu Gln Thr Pro  Ala Gln Glu
    1025                1030                1035

Gln Ala  Tyr Gly Gly Gln Thr  Glu Val Ile Tyr Val  Gly Asp Asn
    1040                1045                1050

Lys Pro  Asp Leu Arg Ala Leu  Ile Tyr Tyr Thr Arg  Ser Ala Val
    1055                1060                1065

Leu Asp  Glu Val Cys Leu Gln  Ala Tyr Glu Gly Ile  Leu Ser Asp
    1070                1075                1080

Glu Gln  Leu Asn Leu Leu Leu  Thr Ser Ala Gly Tyr  Lys Gln Ser
    1085                1090                1095

Thr Arg  Ile Leu Gly Phe Glu  Asp Glu Pro Asp Val  Leu Val Ala
    1100                1105                1110
```

-continued

```
Glu Gln  Gly Phe Thr Arg Tyr  Thr Asn Lys Glu Gly  Phe Tyr Arg
    1115                 1120                 1125

Met Val  Gly Gln Gln Ala Ser  Met Leu Thr Gly Glu  Gln Val Leu
    1130                 1135                 1140

Ser Trp  Asp Asp Asn Trp Cys  Val Val Ile Ser Ala  Glu Asp Ala
    1145                 1150                 1155

Val Lys  Asn Lys Thr Gln Ile  Ala Tyr Asp Tyr Arg  Phe Leu Gln
    1160                 1165                 1170

Ala Asn  Gln Ile Ile Asp Ala  Asn Asn Asn Val Ser  Gln Val Gln
    1175                 1180                 1185

Leu Asp  Ala Leu Gly Arg Val  Ile Tyr Ser Arg Ile  Trp Gly Thr
    1190                 1195                 1200

Glu Lys  Gly Glu Asp Val Gly  Phe Asn Pro Ala Leu  Gln Phe Ser
    1205                 1210                 1215

Ser Pro  Glu Thr Ile Asp Gln  Ala Leu Thr Leu Val  Pro Pro Leu
    1220                 1225                 1230

Pro Val  Gly Ser Cys Tyr Val  Tyr Asp Thr Asn Ser  Trp Met Gly
    1235                 1240                 1245

Lys Ile  Ser Phe Glu Gln Leu  Ser Glu Leu Val Ser  Asp Gly Thr
    1250                 1255                 1260

Glu Leu  Trp Asn Phe Leu Ile  Ala Asn Arg Phe Ile  Thr Leu Asp
    1265                 1270                 1275

Gly Arg  Ile Arg Thr Arg Gly  Arg Phe Gln Lys Asp  Leu Ser Gln
    1280                 1285                 1290

Leu Ser  Gln Thr Val Ser Asn  Ile Phe Lys Gly Ala  Ile Arg Asn
    1295                 1300                 1305

Pro Ser  His Thr Leu Ile Leu  Lys Ala Asp Arg Tyr  Pro Asp Asp
    1310                 1315                 1320

Pro Ala  Gln Gln Ile Gln Thr  Thr Ile Ile Phe Ser  Asp Gly Phe
    1325                 1330                 1335

Gly Arg  Met Leu Gln Ser Ser  Gln Lys Ala Glu Pro  Lys Gly Asp
    1340                 1345                 1350

Ile Leu  Asp Asn Ala Lys Glu  Asn Leu Ile Lys Ser  Glu Asn Lys
    1355                 1360                 1365

Thr Arg  Trp Ile Ile Ser Glu  Arg Ala Asp Tyr Asp  Gly Lys Gly
    1370                 1375                 1380

Thr Val  Ile Arg Asn Phe Gln  Pro Ile Tyr Leu His  Asp Trp Gln
    1385                 1390                 1395

Tyr Val  Asn Asn Glu Ser Ile  His Ser Gln Met Cys  Ala Thr Asn
    1400                 1405                 1410

Tyr Tyr  Tyr Asp Ala Leu Ser  Arg Gln Ile Arg Val  Val Asn Ala
    1415                 1420                 1425

Lys Gly  Tyr Glu Gln Arg Asn  Ala Phe Tyr Pro Trp  Phe Thr Val
    1430                 1435                 1440

Asn Glu  Asp Glu Asn Asp Thr  Trp Asn Asn Gly Gly  Met Glu Glu
    1445                 1450                 1455
```

```
<210> SEQ ID NO 5
<211> LENGTH: 921
<212> TYPE: PRT
<213> ORGANISM: Bacillus thuringiensis EG5858

<400> SEQUENCE: 5

Leu Asp Thr Asn Ser Ile Tyr Asn Gly Thr Pro Thr Ile Ser Val Ile
1               5                   10                  15
```

-continued

```
Asp Asn Arg Gly Leu Gln Ile Arg Thr Leu Glu Tyr Asn Arg Val Thr
            20                  25                  30

Val Glu Asp Pro Ile Asp Glu Tyr Val Thr Arg Asn Thr Tyr Thr Leu
        35                  40                  45

Leu Gly Asn Leu Asp Asp Ser Met Asp Pro Arg Leu Phe Ser Gln Tyr
    50                  55                  60

Gln Asn Asn Asp Asn Thr Leu Pro Asn Met Arg Tyr Asp His Ser Leu
65                  70                  75                  80

Lys Gly Asn Ile Leu Cys Thr Glu Ser Val Asp Ala Gly Gln Lys Val
                85                  90                  95

Gln Ile Phe Asn Ile Glu Gly Arg Pro Ile Trp Phe Arg Asp Ala Asn
            100                 105                 110

Arg Thr Gln Thr Thr Met Glu Tyr Asp Leu Val Gly Arg Pro Thr Ala
        115                 120                 125

Val Leu Glu Lys Leu Asp Gly Asn Glu Thr Pro Lys Tyr Arg Glu Arg
    130                 135                 140

Phe Phe Tyr Gly Glu Asn Glu Arg Gly Ala Gln Ala Asn Asn Leu Cys
145                 150                 155                 160

Gly Gln Leu Val Cys His Tyr Asp Ile Ala Gly Arg Asn Gln Thr Lys
                165                 170                 175

Ser Phe Ser Leu Ser Gly Leu Pro Leu Tyr Gln Ser Arg Gln Leu Leu
            180                 185                 190

Lys Asn Ile Asp Glu Pro Ser Asn Trp Ser Ala Asp Gly Glu Ser Ala
        195                 200                 205

Trp Ile Asn Phe Leu Asp Thr Glu Thr Tyr Asp Thr Ser Trp Gln Tyr
    210                 215                 220

Asp Val Gln Gly Lys Lys Leu Ser Gln Ile Asp Ala Lys Gly Asn Leu
225                 230                 235                 240

Gln Thr Phe Thr Tyr Asn Ser Ile Gly Gln Pro Lys Asn Ile His Ile
                245                 250                 255

Lys Leu Trp Gly Gln Ile Glu Gln Ser Ile Val Asn Gly Ile Glu Tyr
            260                 265                 270

Asn Ala Ala Gly Gln Val Leu Arg Thr Glu Ala Gly Asn Gly Ile Val
        275                 280                 285

Thr Glu Tyr Thr Tyr Glu Glu Ser Ser Gln Arg Leu Met Arg Lys Lys
    290                 295                 300

Asp Ser Arg Lys Ile Pro Ser Lys Arg Arg Glu Ile Leu Gln Asp Tyr
305                 310                 315                 320

His Tyr Glu Tyr Asp Pro Val Gly Asn Ile Leu Ser Ile Ser Asn Glu
                325                 330                 335

Met Asp Ser Val Cys Phe Phe Arg Asn Gln Ile Ile Val Pro Lys Arg
            340                 345                 350

Gln Tyr Thr Tyr Asp Thr Leu Tyr Arg Leu Ile Ser Ser Ser Gly Arg
        355                 360                 365

Glu Ser Asp Thr Leu Arg Gln Tyr Gln Ser Phe Pro Ser Val Ile Thr
    370                 375                 380

Pro Ile Pro Leu Asp Asp Asn Gln Tyr Val Asn Tyr Ser Glu Lys Tyr
385                 390                 395                 400

Ser Tyr Asp Arg Ala Gly Asn Leu Ile Lys Leu Ser His Thr Gly Ala
                405                 410                 415

Thr Gln Tyr Thr Thr Asn Ile Asp Val Asp Val Ala Ser Asn Arg Gly
            420                 425                 430
```

-continued

```
Leu Leu Ser Leu Glu Asn Asn Val Ser Asn Phe Glu Asn Tyr Leu Asp
        435                 440                 445

Arg Ala Gly Asn Gln Lys Ile Leu Leu Pro Gly Ile Pro Met Glu Trp
    450                 455                 460

Asp Ala Arg Asn Gln Leu Ser Arg Val Asn Met Val Val Arg Glu Asp
465                 470                 475                 480

Lys Glu Asn Asp Trp Glu Gly Tyr Leu Tyr Asn Ser Ser Gly Met Arg
                485                 490                 495

Ile Val Lys Gln Asp Thr Arg Lys Lys Gln Asp Ile Thr Lys Thr Asp
            500                 505                 510

Thr Thr Ile Tyr Leu Pro Gly Leu Glu Leu Arg Thr Arg Gln Ile Gly
        515                 520                 525

Asp Asn Val Thr Glu Val Leu Gln Ile Val Thr Ala Ala Gln Val Arg
    530                 535                 540

Val Leu His Trp Lys Asp Glu Thr Gln Pro Thr Gly Ile Thr Asn Asn
545                 550                 555                 560

Gln Tyr Arg Tyr Ser Val Thr Asp His Leu Gly Ser Ser Ser Leu Glu
                565                 570                 575

Leu Asp Lys Gln Gly Lys Ile Ile Ser Lys Glu Glu Phe Tyr Pro Tyr
            580                 585                 590

Gly Gly Thr Ala Leu Trp Thr Ala Arg Thr Glu Ile Glu Ala Asn Tyr
        595                 600                 605

Lys Thr Ile Arg Tyr Ser Gly Lys Glu Arg Asp Ala Thr Gly Leu Tyr
    610                 615                 620

Tyr Tyr Gly His Arg Tyr Tyr Met Pro Trp Ala Gly Arg Trp Leu Asn
625                 630                 635                 640

Pro Asp Pro Ala Gly Thr Val Asp Gly Leu Asn Leu Tyr Arg Met Val
                645                 650                 655

Arg Asn Asn Pro Ile Asn Leu Ile Asp Pro Asp Gly Asn Ala Pro Ile
            660                 665                 670

Gln Ile Thr Asn Tyr Ser Lys Glu Asn Gly Asp Leu Phe Tyr Gly Leu
        675                 680                 685

Ala Asn Glu Arg Gly Arg Tyr Ile Glu Ala Ala Leu Arg Gly Lys Thr
    690                 695                 700

Phe Val Ser Asp Ser Ala Glu Ser Glu Pro Met Ile Ile Asp Gln Tyr
705                 710                 715                 720

Asn Asn Glu Val Ser Lys His Ile Leu Asn Lys Asn Ile Lys Gly Met
                725                 730                 735

Lys Ile Ala Glu His Pro Lys Val Pro Lys Asp Leu Lys Asp Ile Ile
            740                 745                 750

Ser Thr Asp Lys Arg Gly Arg Tyr Pro Leu Trp Asp Asp Tyr Phe Thr
        755                 760                 765

Arg Gly Met Glu Asn Leu Lys Phe Asn Ile Gly Ala Ile Tyr Lys Glu
    770                 775                 780

Thr Lys Asp Lys Ile Asn Thr Asp Thr Tyr His Lys Tyr Tyr Thr Gly
785                 790                 795                 800

Gly Gly Ala Asp Arg Val Pro Lys Leu Leu Trp Lys Arg Gly Ser Lys
                805                 810                 815

Leu Gly Ile Ala Ile Ala Ala Ser Asn Gln Lys Thr Lys Ile His Phe
            820                 825                 830

Val Leu Asp Asn Leu Asp Ile Glu Ser Ile Val Ala Lys Arg Gly Asp
        835                 840                 845

Ser Gly Glu Ser Ile Thr Ala Ser Glu Leu Arg Tyr Val Tyr Arg Asn
```

-continued

```
    850                 855                 860

Arg Glu Arg Leu Gln Gly Arg Val Val Phe Tyr Arg Asn Gly Glu Lys
865                 870                 875                 880

Leu Glu Thr Thr Pro Arg Asn Asp Ser Pro Asp Leu Trp Glu Gln Tyr
                885                 890                 895

Ser Pro Lys Asn Arg Ala Ile Gln Lys Thr Val Gln Lys Asn Ser Phe
            900                 905                 910

Ala Gly Val Phe Ser Lys Cys Ile Arg
        915                 920


<210> SEQ ID NO 6
<211> LENGTH: 927
<212> TYPE: PRT
<213> ORGANISM: Bacillus thuringiensis EG5858

<400> SEQUENCE: 6

Met Asn Thr Pro Ser Ile Tyr Ser Gly Thr Pro Thr Ile Ser Val Val
1               5                   10                  15

Asp Asn Arg Asn Leu Gln Ile Arg Asp Leu Arg Tyr Asn Arg Leu Glu
            20                  25                  30

Lys Arg Asp Leu Val Asp Glu Tyr Ile Thr Arg Asn Thr Tyr Thr Leu
        35                  40                  45

Leu Gly Asn Leu Glu Ser Ser Ile Asp Pro Arg Leu Phe Ser Gln Tyr
    50                  55                  60

Gln Asp Asp Asn Ser Thr Ser Pro Asn Ile Asn Ser Phe Pro Ser Leu
65                  70                  75                  80

Arg Gly Glu Glu Leu Arg Thr Glu Ser Val Asp Ala Gly Arg Lys Val
                85                  90                  95

Asn Leu Phe Asn Ala Glu Gly Lys Ser Ile Trp Phe Met Asp Pro Asn
            100                 105                 110

Asn Ile Glu Thr Ser Ser Asp Tyr Asp Leu Val Gly Arg Pro Ile Ala
        115                 120                 125

Val Phe Glu Lys Gln Glu Asp Glu Glu Ile Pro Gln Cys Lys Asp Arg
    130                 135                 140

Phe Ile Tyr Gly Glu Asp Glu Arg Asn Ala Leu Ala Asn Asn Leu Arg
145                 150                 155                 160

Gly Gln Leu Val Arg His Tyr Asp Thr Ala Gly Arg Ile Gln Thr Glu
                165                 170                 175

Asn Phe Ser Leu Thr Gly Met Pro Leu Asn Gln Ser Arg Gln Leu Leu
            180                 185                 190

Lys Asn Met Asn Gln Ser Ser Asn Trp Ile Ile Asp Asp Glu Asn Thr
        195                 200                 205

Trp Thr Asn Leu Leu Asp Ala Glu Thr Tyr Ser Thr Asn Trp Gln Tyr
    210                 215                 220

Asp Val Gln Gly Arg Lys Val Ala Gln Ile Asp Ala Lys Gly Asn Leu
225                 230                 235                 240

Gln Thr Val Thr Tyr Asn Ile Leu Gly Gln Pro Lys Ala Val Asn Leu
                245                 250                 255

Thr Leu Gln Asp Gln Ser Glu Gln Ser Ile Ala Asn Arg Ile Glu Tyr
            260                 265                 270

Asn Ala Ala Gly Gln Val Gln Arg Thr Glu Ala Gly Asn Gly Ile Leu
        275                 280                 285

Thr Glu Tyr Thr Tyr Glu Glu Ser Thr Gln Arg Leu Met Arg Lys Lys
    290                 295                 300
```

-continued

```
Asp Ser Arg Glu Leu Ser Ser Glu Lys Ile Glu Val Leu Gln Asp Tyr
305                 310                 315                 320

Arg Tyr Glu Tyr Asp Pro Val Gly Asn Ile Leu Ser Ile Ser Asn Asp
                325                 330                 335

Ser Asp Leu Val Arg Phe Phe Arg Asn Gln Ala Val Leu Pro Lys Arg
            340                 345                 350

Gln Tyr Thr Tyr Asp Ala Leu Tyr Gln Leu Val Ser Asn Ser Gly Arg
        355                 360                 365

Glu Ser Asp Ala Leu Arg Gln His Gln Ser Phe Ser Ser Leu Ile Thr
    370                 375                 380

Pro Ile Pro Leu Asp Asp Ser Lys Tyr Val Asn Tyr Phe Glu Lys Tyr
385                 390                 395                 400

His Tyr Asp Arg Ala Gly Asn Leu Ile Lys Leu Asn His Lys Gly Ala
                405                 410                 415

Ser Gln Tyr Thr Thr Asp Ile Tyr Ile Asp Asp Thr Ser Asn Lys Gly
            420                 425                 430

Val Trp Arg Gln Lys Asp Glu Ile Pro Asp Ile Ser Ser Ser Phe Asp
        435                 440                 445

Arg Ala Gly Asn Gln Lys Val Leu Arg Thr Gly Ile Pro Leu Asp Trp
    450                 455                 460

Asp Ser Arg Asn Gln Leu Ser Cys Val Asn Met Val Leu Arg Glu Asn
465                 470                 475                 480

Glu Asp Asn Asp Trp Glu Ser Tyr Ile His Asp Ser Thr Gly Ile Arg
                485                 490                 495

Ile Val Lys Trp Asn Asn Arg Lys Thr Lys Asn Thr Thr Gln Thr Asp
            500                 505                 510

Thr Thr Val Tyr Leu Pro Gly Leu Glu Leu Arg Thr Arg Gln Thr Gly
        515                 520                 525

Glu Lys Phe Thr Glu Leu Leu His Val Val Thr Ala Asp Thr Glu Ile
    530                 535                 540

Ala Gln Val Arg Val Leu His Trp Glu Asp Gly Thr Gln Pro Asn Glu
545                 550                 555                 560

Val Ser Asn Asp Gln Tyr Arg Tyr Ser Ile Asn Asp His Leu Gly Ser
                565                 570                 575

Ser Met Leu Glu Leu Asp Ile Gln Gly Gln Ile Ile Ser Lys Glu Glu
            580                 585                 590

Phe Tyr Pro Tyr Gly Gly Thr Ala Val Trp Thr Ala Arg Thr Lys Val
        595                 600                 605

Glu Ala Asn Tyr Lys Thr Ile Arg Tyr Ser Gly Lys Glu Leu Asp Ala
    610                 615                 620

Thr Gly Leu Tyr Tyr Tyr Gly Tyr Arg Tyr Tyr Met Pro Trp Leu Gly
625                 630                 635                 640

Arg Trp Leu Asn Pro Asp Pro Ala Gly Thr Val Asp Gly Met Asn Leu
                645                 650                 655

Tyr Arg Met Val Gly Asn Asn Pro Ile Asn Ser Ile Asp Lys Met Gly
            660                 665                 670

Leu Leu Pro Glu Lys Pro Asn Ile Phe Thr Leu Ser Ser Gln Glu Val
        675                 680                 685

Thr Glu Ile Lys Thr Lys Thr Asp Leu Ser Asn Met Lys Ile Asn Leu
    690                 695                 700

Ser Ser Ile Lys Met Gly Asn Thr Asp Ala Lys Trp Asn Asp Ile Arg
705                 710                 715                 720

Glu Asn Phe Asp Asp Ile Glu Thr Asn Leu Val Lys Ile Ala Ile His
```

-continued

```
                725                 730                 735

Tyr Glu Arg Glu Tyr Lys Asp Lys Tyr Ser Lys Asn Asn Leu Gly Pro
            740                 745                 750

Ala Val Ala Val Ala Tyr Asn Leu Asn Ser Lys Lys Tyr His Val Gly
        755                 760                 765

Phe Asn His Val Asp Gly Lys Leu Pro Glu Lys Lys Asp Ser Arg Ile
    770                 775                 780

Ala Glu Arg Val Pro Asp Gln Met Ser Lys Gly Val Ser Lys Leu Tyr
785                 790                 795                 800

Lys Asp Trp Thr Lys Gly Ala Gly Ser His Ala Glu Val Tyr Ala Ile
                805                 810                 815

Asn Ser Ala Leu Leu Asp Lys Gly Lys Thr Asp Tyr Lys Asp Thr Asn
            820                 825                 830

Pro Glu Asp Leu Ile Leu Tyr Val Asn Arg Val Asn Gln Gly Lys Thr
        835                 840                 845

Lys Pro Ala Glu Ile Arg Pro Phe Ile Thr Cys Thr Asp Cys Ala Tyr
    850                 855                 860

Thr Leu Val Gly Pro Glu Val Leu Gly Asp Leu Trp Gly Gly Ile Ala
865                 870                 875                 880

Ser Val Ile Asn Gln Asp Ser Val Leu Gly Leu Leu Thr Leu Glu Phe
                885                 890                 895

Pro Glu Asp Lys Ile Met Glu Gly Leu Lys Ile Lys Thr Ile Ser Asn
            900                 905                 910

Ile Lys Lys Tyr Trp Val Pro Asn Ser Ser Gly Gln Met Val Ala
        915                 920                 925


<210> SEQ ID NO 7
<211> LENGTH: 353
<212> TYPE: PRT
<213> ORGANISM: Bacillus thuringiensis EG5858

<400> SEQUENCE: 7

Met Ser Lys Arg Phe Leu Glu Asn Leu Asn Val Glu Glu His Phe Leu
1               5                   10                  15

Asp Ile Ser Asn Trp Pro Gln Val Leu Tyr Glu Asn Leu Asn Glu Glu
            20                  25                  30

Glu Lys Ala Ile Phe Leu Asn Arg Lys Gln Ala Val Asp Leu Phe Met
        35                  40                  45

Thr Thr Glu Thr Lys Ile Ser Asp Ile Glu Leu Gln Phe Gly Phe Gly
    50                  55                  60

Arg Arg His Ile Tyr Arg Phe Val Lys Arg Cys Leu Glu Lys Asp Glu
65                  70                  75                  80

Phe Glu Met Ile Met Gly Tyr Arg Ala Leu Ile Pro Tyr Lys Arg Leu
                85                  90                  95

Lys Asn Tyr His Arg Asn Ser Phe Pro Met Ala Asn Thr Ala Lys Glu
            100                 105                 110

Asn Phe Ser Gly Ala Phe Ser Leu Leu Leu Asp Thr Tyr Pro Ser Leu
        115                 120                 125

Arg Glu Met Ile Ile Asn Ser Tyr Phe Asn Arg Asn Ser Lys Tyr Lys
    130                 135                 140

Val Asn Asp Pro Ile Ile Asn Ile Lys Tyr Leu His Lys Lys Phe Val
145                 150                 155                 160

Asp Glu Cys Arg Arg Leu Gly Ile Lys Thr Asn Glu Tyr Pro Leu Asn
                165                 170                 175
```

```
Thr Lys Thr Leu Ala Lys Lys Ser Leu Glu Arg Phe Val Lys Ser Leu
            180                 185                 190

Ser Lys Ser His Phe Ile Asp Val Ala Lys Arg Asn Gly Glu Gln Ala
        195                 200                 205

Phe Met Ile Ala Lys Asn Thr Gly Asn Gly Asn Lys Asn Asn Pro Met
    210                 215                 220

Thr Ile Arg Pro Leu Glu Arg Val Glu Phe Asp Gly His Arg Ile Asp
225                 230                 235                 240

Ala Ser Ile Ala Ile Ile Phe Lys Thr Pro Glu Gly Asp Glu Ile Val
                245                 250                 255

Glu Val Met Asn Arg Ile Trp Leu Leu Ala Ile Ile Asp Val Ala Thr
            260                 265                 270

Arg Thr Val Leu Gly Tyr His Leu Cys Leu Asn Lys Glu Tyr Ser Ser
        275                 280                 285

Asp Asp Val Leu Met Cys Ile Arg Asn Ala Ile Ile Pro Trp Asn Pro
    290                 295                 300

Lys Lys Leu Thr Ile Glu Gly Leu Lys Tyr Ser Pro Ile Ala Asn Phe
305                 310                 315                 320

Val Ser Asn Ala Ile Pro Glu Ala Ser Tyr Gly Ile Trp Asp Glu Phe
                325                 330                 335

Cys Tyr Asp Asn Ala Lys Ala Asn Leu Ala Lys Asn Val Gln Asn Lys
            340                 345                 350

Leu


<210> SEQ ID NO 8
<211> LENGTH: 3618
<212> TYPE: DNA
<213> ORGANISM: Bacillus thuringiensis EG4332
<220> FEATURE:
<221> NAME/KEY: CDS
<222> LOCATION: (1)..(3615)
<223> OTHER INFORMATION: TIC815

<400> SEQUENCE: 8

atg tct aat tca acc gta ttg caa tct att aaa gaa tcc cgt cgt gat       48
Met Ser Asn Ser Thr Val Leu Gln Ser Ile Lys Glu Ser Arg Arg Asp
1               5                   10                  15

gtg ttg gtg gac cat tat atc gcc aac aat gtt ccc aaa gat cta aca       96
Val Leu Val Asp His Tyr Ile Ala Asn Asn Val Pro Lys Asp Leu Thr
            20                  25                  30

gat aag att act gat gcg gag agt ctt tat gaa tat ttg tta cta gat      144
Asp Lys Ile Thr Asp Ala Glu Ser Leu Tyr Glu Tyr Leu Leu Leu Asp
        35                  40                  45

act aaa ata agt gat ctt gtc aaa aca tct ccg ata gca gag gct att      192
Thr Lys Ile Ser Asp Leu Val Lys Thr Ser Pro Ile Ala Glu Ala Ile
    50                  55                  60

agt agc gta cag tta tat ata aat cgc tgt ata caa ggc tat gaa ggg      240
Ser Ser Val Gln Leu Tyr Ile Asn Arg Cys Ile Gln Gly Tyr Glu Gly
65                  70                  75                  80

gag tta acc acg caa agt aaa agt cat ttt gca cca gga aag ttc tta      288
Glu Leu Thr Thr Gln Ser Lys Ser His Phe Ala Pro Gly Lys Phe Leu
                85                  90                  95

tcc aat tgg gac aat tat aac aag cgc tat acc act tgg tca ggt aaa      336
Ser Asn Trp Asp Asn Tyr Asn Lys Arg Tyr Thr Thr Trp Ser Gly Lys
            100                 105                 110

gaa cgt cta aaa tat tat gca ggc agc tac att gat cca tca tca cgt      384
Glu Arg Leu Lys Tyr Tyr Ala Gly Ser Tyr Ile Asp Pro Ser Ser Arg
        115                 120                 125
```

-continued

```
tac aat aaa aca aac tta ttc aaa aat tta gaa cag agt ata agt caa      432
Tyr Asn Lys Thr Asn Leu Phe Lys Asn Leu Glu Gln Ser Ile Ser Gln
    130                 135                 140

ggg aga ctt acc gaa gaa agt atc aaa aat gca cta cac aac tat ttg      480
Gly Arg Leu Thr Glu Glu Ser Ile Lys Asn Ala Leu His Asn Tyr Leu
145                 150                 155                 160

gac gaa tat gaa act tta gca aat ttg gaa tat ata agc gta aat aaa      528
Asp Glu Tyr Glu Thr Leu Ala Asn Leu Glu Tyr Ile Ser Val Asn Lys
                165                 170                 175

ggt gat ggt gag gat gct gaa agt gta ttg ttc ttt gtt ggt cga act      576
Gly Asp Gly Glu Asp Ala Glu Ser Val Leu Phe Phe Val Gly Arg Thr
            180                 185                 190

caa aca ttt ccc tat gaa tat tac tgg cga agc ttg atc cta aaa aag      624
Gln Thr Phe Pro Tyr Glu Tyr Tyr Trp Arg Ser Leu Ile Leu Lys Lys
        195                 200                 205

aac agt aac aat ata ctg att cca gaa aaa tgg act cag tgg gaa aaa      672
Asn Ser Asn Asn Ile Leu Ile Pro Glu Lys Trp Thr Gln Trp Glu Lys
    210                 215                 220

atc act gcg aat atc ggc gaa gca gtt gac agc tac gta gta att tac      720
Ile Thr Ala Asn Ile Gly Glu Ala Val Asp Ser Tyr Val Val Ile Tyr
225                 230                 235                 240

tgt tat aaa aaa cgc ttg cat gtg cag tgg tct tct tca gag aaa aaa      768
Cys Tyr Lys Lys Arg Leu His Val Gln Trp Ser Ser Ser Glu Lys Lys
                245                 250                 255

caa aat att aac aaa gaa tct att gat ata cag tat cta aat gat tgg      816
Gln Asn Ile Asn Lys Glu Ser Ile Asp Ile Gln Tyr Leu Asn Asp Trp
            260                 265                 270

gtc atg aat agt tct gga gtg tgg tct gcc ttc cag aag tca cct ttc      864
Val Met Asn Ser Ser Gly Val Trp Ser Ala Phe Gln Lys Ser Pro Phe
        275                 280                 285

aaa agt ttt gat tac atc cct aat tca ata acc ggt ttt tct aaa gaa      912
Lys Ser Phe Asp Tyr Ile Pro Asn Ser Ile Thr Gly Phe Ser Lys Glu
    290                 295                 300

aat atc cat att gtt gat aat aaa gta atc tgt gat gat cca aac agt      960
Asn Ile His Ile Val Asp Asn Lys Val Ile Cys Asp Asp Pro Asn Ser
305                 310                 315                 320

att aaa gta aag gtg act tca tta cca ggt aat aga gta cgt att tat     1008
Ile Lys Val Lys Val Thr Ser Leu Pro Gly Asn Arg Val Arg Ile Tyr
                325                 330                 335

ttc gaa aag att tac aat agc gaa tta tca ggt tct act ctc tct ttt     1056
Phe Glu Lys Ile Tyr Asn Ser Glu Leu Ser Gly Ser Thr Leu Ser Phe
            340                 345                 350

tgg ccc gct cta tct tca gac cca gaa att aat gag ggg gaa caa aaa     1104
Trp Pro Ala Leu Ser Ser Asp Pro Glu Ile Asn Glu Gly Glu Gln Lys
        355                 360                 365

gat tat att ata gat ttt gat agt gaa cct tat tat ggg tta ctg gtg     1152
Asp Tyr Ile Ile Asp Phe Asp Ser Glu Pro Tyr Tyr Gly Leu Leu Val
    370                 375                 380

agg tta aat ttc gat caa aaa gag tat tat ttc agt gtt ttg tat tac     1200
Arg Leu Asn Phe Asp Gln Lys Glu Tyr Tyr Phe Ser Val Leu Tyr Tyr
385                 390                 395                 400

cca agt cct tat caa gaa tta tat ggg tca att atc aat gat caa ttt     1248
Pro Ser Pro Tyr Gln Glu Leu Tyr Gly Ser Ile Ile Asn Asp Gln Phe
                405                 410                 415

att ccc cca tca aat agt aaa ata ata gaa cct ata agt ctt act ctt     1296
Ile Pro Pro Ser Asn Ser Lys Ile Ile Glu Pro Ile Ser Leu Thr Leu
            420                 425                 430

aaa aat aat att gat tta gct aac tta tgt gaa aat agc att gat aca     1344
Lys Asn Asn Ile Asp Leu Ala Asn Leu Cys Glu Asn Ser Ile Asp Thr
        435                 440                 445
```

-continued

```
ttg ttt gaa tat aca gtt cag ggg gag ttg ggg gac acc att gct ttt      1392
Leu Phe Glu Tyr Thr Val Gln Gly Glu Leu Gly Asp Thr Ile Ala Phe
    450                 455                 460

tat gga cct tac gga att tat tta tgg gaa att ttt ttc tat ata cct      1440
Tyr Gly Pro Tyr Gly Ile Tyr Leu Trp Glu Ile Phe Phe Tyr Ile Pro
465                 470                 475                 480

ttt tta ata gct gtg agg ctt cta ata gaa caa cga tac gaa ctg gtg      1488
Phe Leu Ile Ala Val Arg Leu Leu Ile Glu Gln Arg Tyr Glu Leu Val
                485                 490                 495

gaa cgt tgg tac aaa ttt ata ttt aac agc gct ggc tac cgt gac gaa      1536
Glu Arg Trp Tyr Lys Phe Ile Phe Asn Ser Ala Gly Tyr Arg Asp Glu
            500                 505                 510

aat ggt aat ttg ttg aaa gat aaa aat gga aat gta cgt tat tgg aat      1584
Asn Gly Asn Leu Leu Lys Asp Lys Asn Gly Asn Val Arg Tyr Trp Asn
        515                 520                 525

gta gta ccg tta caa gaa gat act gag tgg gat gaa aca ttg tct ctt      1632
Val Val Pro Leu Gln Glu Asp Thr Glu Trp Asp Glu Thr Leu Ser Leu
    530                 535                 540

gca atc act gat cca gat gaa ata gct atg gcc gac cca atg caa tac      1680
Ala Ile Thr Asp Pro Asp Glu Ile Ala Met Ala Asp Pro Met Gln Tyr
545                 550                 555                 560

aaa ctg gct ata ttc att cat act tta gat ttt ctc atc aat cgc gga      1728
Lys Leu Ala Ile Phe Ile His Thr Leu Asp Phe Leu Ile Asn Arg Gly
                565                 570                 575

gat cat gcc tat aga atg tta gaa cgt gat act ctt act gag gct aag      1776
Asp His Ala Tyr Arg Met Leu Glu Arg Asp Thr Leu Thr Glu Ala Lys
            580                 585                 590

atg tat tat ata cag gct aaa caa ata ttg ggg ccc cga cct gaa att      1824
Met Tyr Tyr Ile Gln Ala Lys Gln Ile Leu Gly Pro Arg Pro Glu Ile
        595                 600                 605

cgt att aat aat agt tgg gat aat ccg acc ttg caa agc gaa gca ggt      1872
Arg Ile Asn Asn Ser Trp Asp Asn Pro Thr Leu Gln Ser Glu Ala Gly
    610                 615                 620

gct atg act gct gaa cca aca aga aat aat ttg gac ata aca cca atc      1920
Ala Met Thr Ala Glu Pro Thr Arg Asn Asn Leu Asp Ile Thr Pro Ile
625                 630                 635                 640

atg caa tta caa gca ttt ctg aaa tct gaa aat gga cat ttt tta tct      1968
Met Gln Leu Gln Ala Phe Leu Lys Ser Glu Asn Gly His Phe Leu Ser
                645                 650                 655

cca tat aat gat gag ctg tta gct ttc tgg gat aaa atc gaa cta cgt      2016
Pro Tyr Asn Asp Glu Leu Leu Ala Phe Trp Asp Lys Ile Glu Leu Arg
            660                 665                 670

tta tac aac tta cgt cac aat ctg agt tta gat gga caa cct ctt aat      2064
Leu Tyr Asn Leu Arg His Asn Leu Ser Leu Asp Gly Gln Pro Leu Asn
        675                 680                 685

tta ccg cta ttt gtt gaa ccg atg aac ccg cgt gat ttg cag att cag      2112
Leu Pro Leu Phe Val Glu Pro Met Asn Pro Arg Asp Leu Gln Ile Gln
    690                 695                 700

tat agt aca gga gat ggc atg ggg ggg agt gta gct tct tct caa agt      2160
Tyr Ser Thr Gly Asp Gly Met Gly Gly Ser Val Ala Ser Ser Gln Ser
705                 710                 715                 720

tca cag agt atc tat cgt ttc cct att gta att gat aaa gca cgt act      2208
Ser Gln Ser Ile Tyr Arg Phe Pro Ile Val Ile Asp Lys Ala Arg Thr
                725                 730                 735

gca gtt aat agc gtg atc caa ttt gga agt gcc tta gaa aat gca ttc      2256
Ala Val Asn Ser Val Ile Gln Phe Gly Ser Ala Leu Glu Asn Ala Phe
            740                 745                 750

gca aaa caa gat acc gag gcg atg aca tta tta tta caa tct cag cag      2304
Ala Lys Gln Asp Thr Glu Ala Met Thr Leu Leu Leu Gln Ser Gln Gln
```

-continued

```
        755                 760                 765

caa gtt att cta cag caa act cgt gat atg cag gaa aag aac cta gat      2352
Gln Val Ile Leu Gln Gln Thr Arg Asp Met Gln Glu Lys Asn Leu Asp
    770                 775                 780

tcg ttg caa gca agt ctt gaa gct aca acg ata gca aaa gca agt gcc      2400
Ser Leu Gln Ala Ser Leu Glu Ala Thr Thr Ile Ala Lys Ala Ser Ala
785                 790                 795                 800

gaa tca act aag aca cat tat gct ggt tta gtg gaa aac tgg atg tca      2448
Glu Ser Thr Lys Thr His Tyr Ala Gly Leu Val Glu Asn Trp Met Ser
                805                 810                 815

gat aat gaa act agc tca cta aaa tta cgt tca gat gct gga ata atc      2496
Asp Asn Glu Thr Ser Ser Leu Lys Leu Arg Ser Asp Ala Gly Ile Ile
            820                 825                 830

cac acg agc tca gaa gtg gca atg act att gct gct gca tta gat atg      2544
His Thr Ser Ser Glu Val Ala Met Thr Ile Ala Ala Ala Leu Asp Met
        835                 840                 845

gct cct aat gtg ttt ggt atg gca gtg ggg gga tcc cga tgg gga gca      2592
Ala Pro Asn Val Phe Gly Met Ala Val Gly Gly Ser Arg Trp Gly Ala
    850                 855                 860

gct agc act gct gtg gca cag gga ttg caa att agt gct aat gta atg      2640
Ala Ser Thr Ala Val Ala Gln Gly Leu Gln Ile Ser Ala Asn Val Met
865                 870                 875                 880

gaa cag aca gct aat atc atg gat atc agc gaa agt tac cgc cga cgt      2688
Glu Gln Thr Ala Asn Ile Met Asp Ile Ser Glu Ser Tyr Arg Arg Arg
                885                 890                 895

cgt gag gat tgg atg tta cag aga gat gct gcc gag gca gaa gaa tcg      2736
Arg Glu Asp Trp Met Leu Gln Arg Asp Ala Ala Glu Ala Glu Glu Ser
            900                 905                 910

cag ttg aat tta caa att aag gct ctg caa gaa cag att aac atg gcc      2784
Gln Leu Asn Leu Gln Ile Lys Ala Leu Gln Glu Gln Ile Asn Met Ala
        915                 920                 925

cgt aaa caa att ttc ctg tcg gaa act gaa cag gca cat gct caa gca      2832
Arg Lys Gln Ile Phe Leu Ser Glu Thr Glu Gln Ala His Ala Gln Ala
    930                 935                 940

atc tac caa ttg caa tgt act cgt ttt tcg agt caa gct tta tat aat      2880
Ile Tyr Gln Leu Gln Cys Thr Arg Phe Ser Ser Gln Ala Leu Tyr Asn
945                 950                 955                 960

tgg atg gtt gga cgc tta tct tct ctt tac tat caa atg tat gac gca      2928
Trp Met Val Gly Arg Leu Ser Ser Leu Tyr Tyr Gln Met Tyr Asp Ala
                965                 970                 975

aca tta tcc tta tgt ttt atg gca aag aat gct tta gaa aaa gaa tta      2976
Thr Leu Ser Leu Cys Phe Met Ala Lys Asn Ala Leu Glu Lys Glu Leu
            980                 985                 990

gga aag gat aaa aca aca gga atg  ttt act ctc cct gct  tgg gat gat    3024
Gly Lys Asp Lys Thr Thr Gly Met  Phe Thr Leu Pro Ala  Trp Asp Asp
        995                 1000                1005

ttg tat  caa ggg cta ctt gct  ggg gaa atg tta atg  gtg gaa ctt      3069
Leu Tyr  Gln Gly Leu Leu Ala  Gly Glu Met Leu Met  Val Glu Leu
    1010                 1015                 1020

caa aaa  tta gaa aat cta tgg  cta gag gaa aat aaa  tgg ggt atg      3114
Gln Lys  Leu Glu Asn Leu Trp  Leu Glu Glu Asn Lys  Trp Gly Met
    1025                 1030                 1035

gaa gca  gtg aaa act gta tcc  tta gat act ctt atc  cgt aaa aag      3159
Glu Ala  Val Lys Thr Val Ser  Leu Asp Thr Leu Ile  Arg Lys Lys
    1040                 1045                 1050

aac cca  gag ttt gct ttt gta  gat ctt gtt cag gaa  gtt cta agt      3204
Asn Pro  Glu Phe Ala Phe Val  Asp Leu Val Gln Glu  Val Leu Ser
    1055                 1060                 1065

ggc aaa  att cct gaa ggt gtg  agt gga ata gaa gtt  aag ttg caa      3249
```

```
Gly Lys  Ile Pro Glu Gly Val  Ser Gly Ile Glu Val  Lys Leu Gln
    1070                 1075                 1080

aat aat  atc ttt agt gca agt  ctt gac cta tcc tca  ctt ggc ttg      3294
Asn Asn  Ile Phe Ser Ala Ser  Leu Asp Leu Ser Ser  Leu Gly Leu
    1085                 1090                 1095

gag aac  tct tat aat cta aag  gaa aag aat cgt aaa  atc aaa aat      3339
Glu Asn  Ser Tyr Asn Leu Lys  Glu Lys Asn Arg Lys  Ile Lys Asn
    1100                 1105                 1110

ctg tca  gtt acc tta cca gca  ctt tta gga cct tat  cag gat gtg      3384
Leu Ser  Val Thr Leu Pro Ala  Leu Leu Gly Pro Tyr  Gln Asp Val
    1115                 1120                 1125

gaa gca  acc tta tca cta ggc  ggt gaa act gtt acg  ctt tct cat      3429
Glu Ala  Thr Leu Ser Leu Gly  Gly Glu Thr Val Thr  Leu Ser His
    1130                 1135                 1140

gga gta  gat gat agt ggc tta  ttc ata aca gat ttc  aat gac agc      3474
Gly Val  Asp Asp Ser Gly Leu  Phe Ile Thr Asp Phe  Asn Asp Ser
    1145                 1150                 1155

cgt ttt  cta cct ttc gag gga  atg aat ttg cta tcg  ggg aca ctt      3519
Arg Phe  Leu Pro Phe Glu Gly  Met Asn Leu Leu Ser  Gly Thr Leu
    1160                 1165                 1170

act tta  gct att ttc cat aca  gga aaa gat ggt gac  cag cgc tct      3564
Thr Leu  Ala Ile Phe His Thr  Gly Lys Asp Gly Asp  Gln Arg Ser
    1175                 1180                 1185

tta cta  gaa agc tta aat gat  gtc ata ttc cac att  cga tat gta      3609
Leu Leu  Glu Ser Leu Asn Asp  Val Ile Phe His Ile  Arg Tyr Val
    1190                 1195                 1200

atg aaa  tag                                                        3618
Met Lys
    1205


<210> SEQ ID NO 9
<211> LENGTH: 1205
<212> TYPE: PRT
<213> ORGANISM: Bacillus thuringiensis EG4332

<400> SEQUENCE: 9

Met Ser Asn Ser Thr Val Leu Gln Ser Ile Lys Glu Ser Arg Arg Asp
1               5                   10                  15

Val Leu Val Asp His Tyr Ile Ala Asn Asn Val Pro Lys Asp Leu Thr
            20                  25                  30

Asp Lys Ile Thr Asp Ala Glu Ser Leu Tyr Glu Tyr Leu Leu Leu Asp
        35                  40                  45

Thr Lys Ile Ser Asp Leu Val Lys Thr Ser Pro Ile Ala Glu Ala Ile
    50                  55                  60

Ser Ser Val Gln Leu Tyr Ile Asn Arg Cys Ile Gln Gly Tyr Glu Gly
65                  70                  75                  80

Glu Leu Thr Thr Gln Ser Lys Ser His Phe Ala Pro Gly Lys Phe Leu
                85                  90                  95

Ser Asn Trp Asp Asn Tyr Asn Lys Arg Tyr Thr Thr Trp Ser Gly Lys
            100                 105                 110

Glu Arg Leu Lys Tyr Tyr Ala Gly Ser Tyr Ile Asp Pro Ser Ser Arg
        115                 120                 125

Tyr Asn Lys Thr Asn Leu Phe Lys Asn Leu Glu Gln Ser Ile Ser Gln
    130                 135                 140

Gly Arg Leu Thr Glu Glu Ser Ile Lys Asn Ala Leu His Asn Tyr Leu
145                 150                 155                 160

Asp Glu Tyr Glu Thr Leu Ala Asn Leu Glu Tyr Ile Ser Val Asn Lys
                165                 170                 175
```

```
Gly Asp Gly Glu Asp Ala Glu Ser Val Leu Phe Phe Val Gly Arg Thr
            180                 185                 190

Gln Thr Phe Pro Tyr Glu Tyr Tyr Trp Arg Ser Leu Ile Leu Lys Lys
        195                 200                 205

Asn Ser Asn Asn Ile Leu Ile Pro Glu Lys Trp Thr Gln Trp Glu Lys
    210                 215                 220

Ile Thr Ala Asn Ile Gly Glu Ala Val Asp Ser Tyr Val Val Ile Tyr
225                 230                 235                 240

Cys Tyr Lys Lys Arg Leu His Val Gln Trp Ser Ser Ser Glu Lys Lys
                245                 250                 255

Gln Asn Ile Asn Lys Glu Ser Ile Asp Ile Gln Tyr Leu Asn Asp Trp
            260                 265                 270

Val Met Asn Ser Ser Gly Val Trp Ser Ala Phe Gln Lys Ser Pro Phe
        275                 280                 285

Lys Ser Phe Asp Tyr Ile Pro Asn Ser Ile Thr Gly Phe Ser Lys Glu
    290                 295                 300

Asn Ile His Ile Val Asp Asn Lys Val Ile Cys Asp Asp Pro Asn Ser
305                 310                 315                 320

Ile Lys Val Lys Val Thr Ser Leu Pro Gly Asn Arg Val Arg Ile Tyr
                325                 330                 335

Phe Glu Lys Ile Tyr Asn Ser Glu Leu Ser Gly Ser Thr Leu Ser Phe
            340                 345                 350

Trp Pro Ala Leu Ser Ser Asp Pro Glu Ile Asn Glu Gly Glu Gln Lys
        355                 360                 365

Asp Tyr Ile Ile Asp Phe Asp Ser Glu Pro Tyr Tyr Gly Leu Leu Val
    370                 375                 380

Arg Leu Asn Phe Asp Gln Lys Glu Tyr Tyr Phe Ser Val Leu Tyr Tyr
385                 390                 395                 400

Pro Ser Pro Tyr Gln Glu Leu Tyr Gly Ser Ile Ile Asn Asp Gln Phe
                405                 410                 415

Ile Pro Pro Ser Asn Ser Lys Ile Ile Glu Pro Ile Ser Leu Thr Leu
            420                 425                 430

Lys Asn Asn Ile Asp Leu Ala Asn Leu Cys Glu Asn Ser Ile Asp Thr
        435                 440                 445

Leu Phe Glu Tyr Thr Val Gln Gly Glu Leu Gly Asp Thr Ile Ala Phe
    450                 455                 460

Tyr Gly Pro Tyr Gly Ile Tyr Leu Trp Glu Ile Phe Phe Tyr Ile Pro
465                 470                 475                 480

Phe Leu Ile Ala Val Arg Leu Leu Ile Glu Gln Arg Tyr Glu Leu Val
                485                 490                 495

Glu Arg Trp Tyr Lys Phe Ile Phe Asn Ser Ala Gly Tyr Arg Asp Glu
            500                 505                 510

Asn Gly Asn Leu Leu Lys Asp Lys Asn Gly Asn Val Arg Tyr Trp Asn
        515                 520                 525

Val Val Pro Leu Gln Glu Asp Thr Glu Trp Asp Glu Thr Leu Ser Leu
    530                 535                 540

Ala Ile Thr Asp Pro Asp Glu Ile Ala Met Ala Asp Pro Met Gln Tyr
545                 550                 555                 560

Lys Leu Ala Ile Phe Ile His Thr Leu Asp Phe Leu Ile Asn Arg Gly
                565                 570                 575

Asp His Ala Tyr Arg Met Leu Glu Arg Asp Thr Leu Thr Glu Ala Lys
            580                 585                 590
```

-continued

```
Met Tyr Tyr Ile Gln Ala Lys Gln Ile Leu Gly Pro Arg Pro Glu Ile
        595                 600                 605

Arg Ile Asn Asn Ser Trp Asp Asn Pro Thr Leu Gln Ser Glu Ala Gly
    610                 615                 620

Ala Met Thr Ala Glu Pro Thr Arg Asn Asn Leu Asp Ile Thr Pro Ile
625                 630                 635                 640

Met Gln Leu Gln Ala Phe Leu Lys Ser Glu Asn Gly His Phe Leu Ser
                645                 650                 655

Pro Tyr Asn Asp Glu Leu Leu Ala Phe Trp Asp Lys Ile Glu Leu Arg
            660                 665                 670

Leu Tyr Asn Leu Arg His Asn Leu Ser Leu Asp Gly Gln Pro Leu Asn
        675                 680                 685

Leu Pro Leu Phe Val Glu Pro Met Asn Pro Arg Asp Leu Gln Ile Gln
    690                 695                 700

Tyr Ser Thr Gly Asp Gly Met Gly Gly Ser Val Ala Ser Ser Gln Ser
705                 710                 715                 720

Ser Gln Ser Ile Tyr Arg Phe Pro Ile Val Ile Asp Lys Ala Arg Thr
                725                 730                 735

Ala Val Asn Ser Val Ile Gln Phe Gly Ser Ala Leu Glu Asn Ala Phe
            740                 745                 750

Ala Lys Gln Asp Thr Glu Ala Met Thr Leu Leu Leu Gln Ser Gln Gln
        755                 760                 765

Gln Val Ile Leu Gln Gln Thr Arg Asp Met Gln Glu Lys Asn Leu Asp
    770                 775                 780

Ser Leu Gln Ala Ser Leu Glu Ala Thr Thr Ile Ala Lys Ala Ser Ala
785                 790                 795                 800

Glu Ser Thr Lys Thr His Tyr Ala Gly Leu Val Glu Asn Trp Met Ser
                805                 810                 815

Asp Asn Glu Thr Ser Ser Leu Lys Leu Arg Ser Asp Ala Gly Ile Ile
            820                 825                 830

His Thr Ser Ser Glu Val Ala Met Thr Ile Ala Ala Ala Leu Asp Met
        835                 840                 845

Ala Pro Asn Val Phe Gly Met Ala Val Gly Gly Ser Arg Trp Gly Ala
    850                 855                 860

Ala Ser Thr Ala Val Ala Gln Gly Leu Gln Ile Ser Ala Asn Val Met
865                 870                 875                 880

Glu Gln Thr Ala Asn Ile Met Asp Ile Ser Glu Ser Tyr Arg Arg Arg
                885                 890                 895

Arg Glu Asp Trp Met Leu Gln Arg Asp Ala Ala Glu Ala Glu Glu Ser
            900                 905                 910

Gln Leu Asn Leu Gln Ile Lys Ala Leu Gln Glu Gln Ile Asn Met Ala
        915                 920                 925

Arg Lys Gln Ile Phe Leu Ser Glu Thr Glu Gln Ala His Ala Gln Ala
    930                 935                 940

Ile Tyr Gln Leu Gln Cys Thr Arg Phe Ser Ser Gln Ala Leu Tyr Asn
945                 950                 955                 960

Trp Met Val Gly Arg Leu Ser Ser Leu Tyr Tyr Gln Met Tyr Asp Ala
                965                 970                 975

Thr Leu Ser Leu Cys Phe Met Ala Lys Asn Ala Leu Glu Lys Glu Leu
            980                 985                 990

Gly Lys Asp Lys Thr Thr Gly Met  Phe Thr Leu Pro Ala  Trp Asp Asp
        995                 1000                1005

Leu Tyr  Gln Gly Leu Leu Ala  Gly Glu Met Leu Met  Val Glu Leu
```

-continued

```
    1010                1015                1020

Gln Lys  Leu Glu Asn Leu Trp  Leu Glu Glu Asn Lys  Trp Gly Met
    1025                1030                1035

Glu Ala  Val Lys Thr Val Ser  Leu Asp Thr Leu Ile  Arg Lys Lys
    1040                1045                1050

Asn Pro  Glu Phe Ala Phe Val  Asp Leu Val Gln Glu  Val Leu Ser
    1055                1060                1065

Gly Lys  Ile Pro Glu Gly Val  Ser Gly Ile Glu Val  Lys Leu Gln
    1070                1075                1080

Asn Asn  Ile Phe Ser Ala Ser  Leu Asp Leu Ser Ser  Leu Gly Leu
    1085                1090                1095

Glu Asn  Ser Tyr Asn Leu Lys  Glu Lys Asn Arg Lys  Ile Lys Asn
    1100                1105                1110

Leu Ser  Val Thr Leu Pro Ala  Leu Leu Gly Pro Tyr  Gln Asp Val
    1115                1120                1125

Glu Ala  Thr Leu Ser Leu Gly  Gly Glu Thr Val Thr  Leu Ser His
    1130                1135                1140

Gly Val  Asp Asp Ser Gly Leu  Phe Ile Thr Asp Phe  Asn Asp Ser
    1145                1150                1155

Arg Phe  Leu Pro Phe Glu Gly  Met Asn Leu Leu Ser  Gly Thr Leu
    1160                1165                1170

Thr Leu  Ala Ile Phe His Thr  Gly Lys Asp Gly Asp  Gln Arg Ser
    1175                1180                1185

Leu Leu  Glu Ser Leu Asn Asp  Val Ile Phe His Ile  Arg Tyr Val
    1190                1195                1200

Met Lys
    1205


<210> SEQ ID NO 10
<211> LENGTH: 3246
<212> TYPE: DNA
<213> ORGANISM: Bacillus thuringiensis EG4096
<220> FEATURE:
<221> NAME/KEY: CDS
<222> LOCATION: (1)..(3243)
<223> OTHER INFORMATION: TIC904

<400> SEQUENCE: 10

atg tca aaa aca gaa cat act gcc ggt gta ttt caa att gga acg caa       48
Met Ser Lys Thr Glu His Thr Ala Gly Val Phe Gln Ile Gly Thr Gln
1               5                   10                  15

act tta aca tcg gtg ttg cat cag tca ggc tac caa acc gta ttt gat       96
Thr Leu Thr Ser Val Leu His Gln Ser Gly Tyr Gln Thr Val Phe Asp
            20                  25                  30

att gcg tct gag aat ctt tcg gaa ttt aag gag aat aat cct gag att      144
Ile Ala Ser Glu Asn Leu Ser Glu Phe Lys Glu Asn Asn Pro Glu Ile
        35                  40                  45

cct tct tct gat gcg aaa gag att tac aga tta gct gta cag aga tca      192
Pro Ser Ser Asp Ala Lys Glu Ile Tyr Arg Leu Ala Val Gln Arg Ser
    50                  55                  60

gaa aat tta ctc atg ctt ttt aaa tct tgg caa tta cac aat gaa cct      240
Glu Asn Leu Leu Met Leu Phe Lys Ser Trp Gln Leu His Asn Glu Pro
65                  70                  75                  80

ctt att cgc aat ata ctg aag tta tct tca gac acc ggg ttg aaa acg      288
Leu Ile Arg Asn Ile Leu Lys Leu Ser Ser Asp Thr Gly Leu Lys Thr
                85                  90                  95

atg cgt act gcg cta gag cgt agt tta gga agt gga tct gat ttt gaa      336
Met Arg Thr Ala Leu Glu Arg Ser Leu Gly Ser Gly Ser Asp Phe Glu
```

```
            100                 105                 110

aat ctg ttt cct gac cgt tcg tta gag gga tat gca gaa atg gct tcc      384
Asn Leu Phe Pro Asp Arg Ser Leu Glu Gly Tyr Ala Glu Met Ala Ser
        115                 120                 125

ata caa tcc ctt ttc tca cca ggc cgg tat cta gct gta ttg tac aaa      432
Ile Gln Ser Leu Phe Ser Pro Gly Arg Tyr Leu Ala Val Leu Tyr Lys
    130                 135                 140

att gca aga caa cta cac gaa aca gga gac cag ctc cat att gat aaa      480
Ile Ala Arg Gln Leu His Glu Thr Gly Asp Gln Leu His Ile Asp Lys
145                 150                 155                 160

cgt cgt ccc gat tta aaa aca cta aca ctg agt aca aac aat atg aac      528
Arg Arg Pro Asp Leu Lys Thr Leu Thr Leu Ser Thr Asn Asn Met Asn
                165                 170                 175

aaa gag gtt tct tcc cta gat att ttg tta gat ata ctg cag ccc gaa      576
Lys Glu Val Ser Ser Leu Asp Ile Leu Leu Asp Ile Leu Gln Pro Glu
            180                 185                 190

ggg att ggg aaa cta tca tct cta aag gat aca tat tat cct atg tct      624
Gly Ile Gly Lys Leu Ser Ser Leu Lys Asp Thr Tyr Tyr Pro Met Ser
        195                 200                 205

ctt ccc tat gat gat gac ctt aag caa att cat gct gtt gtg gaa gaa      672
Leu Pro Tyr Asp Asp Asp Leu Lys Gln Ile His Ala Val Val Glu Glu
    210                 215                 220

aag tca tcc aat tta atg gcg att tgg gac att ctg cta gac aca caa      720
Lys Ser Ser Asn Leu Met Ala Ile Trp Asp Ile Leu Leu Asp Thr Gln
225                 230                 235                 240

cgt gag gcc atc cta cag gtc cca caa aac caa aag tta tct aat aca      768
Arg Glu Ala Ile Leu Gln Val Pro Gln Asn Gln Lys Leu Ser Asn Thr
                245                 250                 255

cca gca ttg cta gag gga caa gag ttt tac ttg gag gct aac ggt caa      816
Pro Ala Leu Leu Glu Gly Gln Glu Phe Tyr Leu Glu Ala Asn Gly Gln
            260                 265                 270

cga tta ttt ttt gca cat aaa ctt gaa ctt gga tca act gta agt tgt      864
Arg Leu Phe Phe Ala His Lys Leu Glu Leu Gly Ser Thr Val Ser Cys
        275                 280                 285

aag gtg aat att ggg aaa cca caa gcc ctt gct gtt gcg ccg gcg aaa      912
Lys Val Asn Ile Gly Lys Pro Gln Ala Leu Ala Val Ala Pro Ala Lys
    290                 295                 300

ttt caa ctt gtg tat tac aaa gga gag tcc ttc tta cgt att gca aat      960
Phe Gln Leu Val Tyr Tyr Lys Gly Glu Ser Phe Leu Arg Ile Ala Asn
305                 310                 315                 320

gat gtt tcc ctt aat ggg aaa ttg ttg gag aat tgt tat cta att agt     1008
Asp Val Ser Leu Asn Gly Lys Leu Leu Glu Asn Cys Tyr Leu Ile Ser
                325                 330                 335

gac aac ggg cag agt agc aat aaa caa ggt cct tat tgt ctt atg tta     1056
Asp Asn Gly Gln Ser Ser Asn Lys Gln Gly Pro Tyr Cys Leu Met Leu
            340                 345                 350

aat gaa agt aat cgg gat acc cct gga gca aag cat tta ccc gtt aaa     1104
Asn Glu Ser Asn Arg Asp Thr Pro Gly Ala Lys His Leu Pro Val Lys
        355                 360                 365

gtt gag aag atg acg gat acc tct atc cgc att ttt gta cca caa cat     1152
Val Glu Lys Met Thr Asp Thr Ser Ile Arg Ile Phe Val Pro Gln His
    370                 375                 380

ggt tac ttt gga aaa ggt gaa ttc atg gct tct gat tgg gac agt cca     1200
Gly Tyr Phe Gly Lys Gly Glu Phe Met Ala Ser Asp Trp Asp Ser Pro
385                 390                 395                 400

ctg gca ctg aat cta gat tta act aat gca gtg act ttt gtc ttg aaa     1248
Leu Ala Leu Asn Leu Asp Leu Thr Asn Ala Val Thr Phe Val Leu Lys
                405                 410                 415

aag aat gca act ggc gat gag aca att tct att cat gac ata ttt cca     1296
```

-continued

```
Lys Asn Ala Thr Gly Asp Glu Thr Ile Ser Ile His Asp Ile Phe Pro
            420                 425                 430

ggt att gtt gat aca acc cca cat cca cca acg agg gaa acg ttg ttt      1344
Gly Ile Val Asp Thr Thr Pro His Pro Pro Thr Arg Glu Thr Leu Phe
        435                 440                 445

ctg acg cca aat agt tat caa ttg tta gtt aat cca gat cca act gca      1392
Leu Thr Pro Asn Ser Tyr Gln Leu Leu Val Asn Pro Asp Pro Thr Ala
    450                 455                 460

tta gac att gcc aat cat tat aat att aaa aca act aaa aat cga ggt      1440
Leu Asp Ile Ala Asn His Tyr Asn Ile Lys Thr Thr Lys Asn Arg Gly
465                 470                 475                 480

atc gct gag tta gtt gag aat tta aat att gtt gat acg ttc tgt tta      1488
Ile Ala Glu Leu Val Glu Asn Leu Asn Ile Val Asp Thr Phe Cys Leu
                485                 490                 495

aaa aca ggt tta aag ttt aat aag ttg tta gaa ctt act atg cag agg      1536
Lys Thr Gly Leu Lys Phe Asn Lys Leu Leu Glu Leu Thr Met Gln Arg
            500                 505                 510

gat tat cag aca cca aat aac gaa tat gag agt aat ttt tta aaa ttt      1584
Asp Tyr Gln Thr Pro Asn Asn Glu Tyr Glu Ser Asn Phe Leu Lys Phe
        515                 520                 525

gga agt gag aaa tat gtt cct gtt tca aca tat gga gct aaa ttt tta      1632
Gly Ser Glu Lys Tyr Val Pro Val Ser Thr Tyr Gly Ala Lys Phe Leu
    530                 535                 540

acg ggt atg gaa aaa att cct ttg tgg gta aaa caa tat aaa gga gca      1680
Thr Gly Met Glu Lys Ile Pro Leu Trp Val Lys Gln Tyr Lys Gly Ala
545                 550                 555                 560

aaa gtc cct gtc tta aac ttt act tcg aat aat gtt gtg tct ttg gca      1728
Lys Val Pro Val Leu Asn Phe Thr Ser Asn Asn Val Val Ser Leu Ala
                565                 570                 575

gga agg gcg gaa aag tta atc cga ctt gcc cag aat aca ggt ctt tca      1776
Gly Arg Ala Glu Lys Leu Ile Arg Leu Ala Gln Asn Thr Gly Leu Ser
            580                 585                 590

ttt gaa cag tta gat tgg ctg att att aat gcg agt cag ggt gta atg      1824
Phe Glu Gln Leu Asp Trp Leu Ile Ile Asn Ala Ser Gln Gly Val Met
        595                 600                 605

gag cat gga aga gaa att att cta gat gga ccg gta ctt gag gca ata      1872
Glu His Gly Arg Glu Ile Ile Leu Asp Gly Pro Val Leu Glu Ala Ile
    610                 615                 620

gct gaa ttt aca aga ctt cat acg cgt tat ggt att aca aca gat atg      1920
Ala Glu Phe Thr Arg Leu His Thr Arg Tyr Gly Ile Thr Thr Asp Met
625                 630                 635                 640

ttt gct gct ttt att ggt gct gta aat cca tat gca gaa aac gga cag      1968
Phe Ala Ala Phe Ile Gly Ala Val Asn Pro Tyr Ala Glu Asn Gly Gln
                645                 650                 655

aaa agt ttt tat caa tct aca ttt tct aaa atg gat gaa tcc ttt acc      2016
Lys Ser Phe Tyr Gln Ser Thr Phe Ser Lys Met Asp Glu Ser Phe Thr
            660                 665                 670

att cct ttg gga gca aat tta aca ttt gca gtg gaa aaa caa ggg gaa      2064
Ile Pro Leu Gly Ala Asn Leu Thr Phe Ala Val Glu Lys Gln Gly Glu
        675                 680                 685

cta gaa tct att tgc tgt aaa gct tta ggc gtt aca cca gat gag ctg      2112
Leu Glu Ser Ile Cys Cys Lys Ala Leu Gly Val Thr Pro Asp Glu Leu
    690                 695                 700

tct cgc att gct gga tac tgc ttt gat gca gca aag ggt gtc aaa caa      2160
Ser Arg Ile Ala Gly Tyr Cys Phe Asp Ala Ala Lys Gly Val Lys Gln
705                 710                 715                 720

aat atg gat gaa gca agc ttt ggt caa ctt ctc cgt atg gga aag att      2208
Asn Met Asp Glu Ala Ser Phe Gly Gln Leu Leu Arg Met Gly Lys Ile
                725                 730                 735
```

-continued

```
cct cac atg ctc gga ttg agt ttt acg gag gcg gaa gta ttg tgg aca      2256
Pro His Met Leu Gly Leu Ser Phe Thr Glu Ala Glu Val Leu Trp Thr
            740                 745                 750

tta atg gca gat ggt aag gat act ttc ctc cgt gcc att ggc caa aca      2304
Leu Met Ala Asp Gly Lys Asp Thr Phe Leu Arg Ala Ile Gly Gln Thr
        755                 760                 765

ttc aat ctc cag gtt cta tct atc atc cgt gac acg gag agg gtt gtg      2352
Phe Asn Leu Gln Val Leu Ser Ile Ile Arg Asp Thr Glu Arg Val Val
    770                 775                 780

gaa tgg atg gaa gct cat cag cta gat att gga gct gta caa gct atg      2400
Glu Trp Met Glu Ala His Gln Leu Asp Ile Gly Ala Val Gln Ala Met
785                 790                 795                 800

gtg aca aat caa tac agc ggt aca gcg aca ccc aca cta tat aac ttt      2448
Val Thr Asn Gln Tyr Ser Gly Thr Ala Thr Pro Thr Leu Tyr Asn Phe
                805                 810                 815

tta gaa acg gtg tat caa tct aca aac ggt ggt gat atg aat cgt agt      2496
Leu Glu Thr Val Tyr Gln Ser Thr Asn Gly Gly Asp Met Asn Arg Ser
            820                 825                 830

ctt aac aat caa atg aca aca aat ctg tac cgc gca ctg gga aca aac      2544
Leu Asn Asn Gln Met Thr Thr Asn Leu Tyr Arg Ala Leu Gly Thr Asn
        835                 840                 845

ttt aac ttg aaa gta aat gtg atg aca caa gtt cta aaa tgg atg gaa      2592
Phe Asn Leu Lys Val Asn Val Met Thr Gln Val Leu Lys Trp Met Glu
    850                 855                 860

aaa aca att aca gga ttt acg atg cag aat ttt tgg aag cag atg caa      2640
Lys Thr Ile Thr Gly Phe Thr Met Gln Asn Phe Trp Lys Gln Met Gln
865                 870                 875                 880

gaa tat ttc cgt gta aat cat gaa gaa tca tta agt gct cta gaa agg      2688
Glu Tyr Phe Arg Val Asn His Glu Glu Ser Leu Ser Ala Leu Glu Arg
                885                 890                 895

cag gct gaa tta ttg aga tgg tgt cag caa atg agt caa tat gtg cta      2736
Gln Ala Glu Leu Leu Arg Trp Cys Gln Gln Met Ser Gln Tyr Val Leu
            900                 905                 910

att gtt caa tgg tgc ggg tta agc gaa caa gat ttg atg ctt gta atg      2784
Ile Val Gln Trp Cys Gly Leu Ser Glu Gln Asp Leu Met Leu Val Met
        915                 920                 925

gaa cac cct gaa cgt gta cta gac aaa caa cat gtg tcg cct gca cct      2832
Glu His Pro Glu Arg Val Leu Asp Lys Gln His Val Ser Pro Ala Pro
    930                 935                 940

tct atg tat cta ctg ctc gtg tta tct cgc ctg aaa gaa tgg cag cag      2880
Ser Met Tyr Leu Leu Leu Val Leu Ser Arg Leu Lys Glu Trp Gln Gln
945                 950                 955                 960

cgc gtt cag gtt tcc agt gat gag gca atg cgc tac ttt gag cag gta      2928
Arg Val Gln Val Ser Ser Asp Glu Ala Met Arg Tyr Phe Glu Gln Val
                965                 970                 975

aat gtt cca gag att aca tct gaa act gca att aag ctc ctt gca cgt      2976
Asn Val Pro Glu Ile Thr Ser Glu Thr Ala Ile Lys Leu Leu Ala Arg
            980                 985                 990

att cat gga tgg aat gaa ggc tat  acc act tct atg aat  gat tac ttg    3024
Ile His Gly Trp Asn Glu Gly Tyr  Thr Thr Ser Met Asn  Asp Tyr Leu
        995                 1000                1005

ctg gaa  gag aag gaa tac ccg  aag aac ttt gaa caa  gtc ttt cga      3069
Leu Glu  Glu Lys Glu Tyr Pro  Lys Asn Phe Glu Gln  Val Phe Arg
    1010                1015                1020

ttg gaa  agc tgg gtg aac cta  gga cgt caa ttt aat  gtt ggt agc      3114
Leu Glu  Ser Trp Val Asn Leu  Gly Arg Gln Phe Asn  Val Gly Ser
    1025                1030                1035

cga aca  tta gga gaa ctt gtt  gat atg gca aaa caa  aat gaa aca      3159
Arg Thr  Leu Gly Glu Leu Val  Asp Met Ala Lys Gln  Asn Glu Thr
    1040                1045                1050
```

```
gcg gaa  aac aac aac tta att  act tca gta gct caa  agc ttg atg      3204
Ala Glu  Asn Asn Asn Leu Ile  Thr Ser Val Ala Gln  Ser Leu Met
    1055                 1060                 1065

gct gcc  gca gca caa cat aca  aat atg gat aag gga  tgg tga         3246
Ala Ala  Ala Ala Gln His Thr  Asn Met Asp Lys Gly  Trp
    1070                 1075                 1080


<210> SEQ ID NO 11
<211> LENGTH: 1081
<212> TYPE: PRT
<213> ORGANISM: Bacillus thuringiensis EG4096

<400> SEQUENCE: 11

Met Ser Lys Thr Glu His Thr Ala Gly Val Phe Gln Ile Gly Thr Gln
1               5                   10                  15

Thr Leu Thr Ser Val Leu His Gln Ser Gly Tyr Gln Thr Val Phe Asp
            20                  25                  30

Ile Ala Ser Glu Asn Leu Ser Glu Phe Lys Glu Asn Asn Pro Glu Ile
        35                  40                  45

Pro Ser Ser Asp Ala Lys Glu Ile Tyr Arg Leu Ala Val Gln Arg Ser
    50                  55                  60

Glu Asn Leu Leu Met Leu Phe Lys Ser Trp Gln Leu His Asn Glu Pro
65                  70                  75                  80

Leu Ile Arg Asn Ile Leu Lys Leu Ser Ser Asp Thr Gly Leu Lys Thr
                85                  90                  95

Met Arg Thr Ala Leu Glu Arg Ser Leu Gly Ser Gly Ser Asp Phe Glu
            100                 105                 110

Asn Leu Phe Pro Asp Arg Ser Leu Glu Gly Tyr Ala Glu Met Ala Ser
        115                 120                 125

Ile Gln Ser Leu Phe Ser Pro Gly Arg Tyr Leu Ala Val Leu Tyr Lys
    130                 135                 140

Ile Ala Arg Gln Leu His Glu Thr Gly Asp Gln Leu His Ile Asp Lys
145                 150                 155                 160

Arg Arg Pro Asp Leu Lys Thr Leu Thr Leu Ser Thr Asn Asn Met Asn
                165                 170                 175

Lys Glu Val Ser Ser Leu Asp Ile Leu Leu Asp Ile Leu Gln Pro Glu
            180                 185                 190

Gly Ile Gly Lys Leu Ser Ser Leu Lys Asp Thr Tyr Tyr Pro Met Ser
        195                 200                 205

Leu Pro Tyr Asp Asp Asp Leu Lys Gln Ile His Ala Val Val Glu Glu
    210                 215                 220

Lys Ser Ser Asn Leu Met Ala Ile Trp Asp Ile Leu Leu Asp Thr Gln
225                 230                 235                 240

Arg Glu Ala Ile Leu Gln Val Pro Gln Asn Gln Lys Leu Ser Asn Thr
                245                 250                 255

Pro Ala Leu Leu Glu Gly Gln Glu Phe Tyr Leu Glu Ala Asn Gly Gln
            260                 265                 270

Arg Leu Phe Phe Ala His Lys Leu Glu Leu Gly Ser Thr Val Ser Cys
        275                 280                 285

Lys Val Asn Ile Gly Lys Pro Gln Ala Leu Ala Val Ala Pro Ala Lys
    290                 295                 300

Phe Gln Leu Val Tyr Tyr Lys Gly Glu Ser Phe Leu Arg Ile Ala Asn
305                 310                 315                 320

Asp Val Ser Leu Asn Gly Lys Leu Leu Glu Asn Cys Tyr Leu Ile Ser
                325                 330                 335
```

-continued

```
Asp Asn Gly Gln Ser Ser Asn Lys Gln Gly Pro Tyr Cys Leu Met Leu
            340                 345                 350

Asn Glu Ser Asn Arg Asp Thr Pro Gly Ala Lys His Leu Pro Val Lys
        355                 360                 365

Val Glu Lys Met Thr Asp Thr Ser Ile Arg Ile Phe Val Pro Gln His
    370                 375                 380

Gly Tyr Phe Gly Lys Gly Glu Phe Met Ala Ser Asp Trp Asp Ser Pro
385                 390                 395                 400

Leu Ala Leu Asn Leu Asp Leu Thr Asn Ala Val Thr Phe Val Leu Lys
                405                 410                 415

Lys Asn Ala Thr Gly Asp Glu Thr Ile Ser Ile His Asp Ile Phe Pro
            420                 425                 430

Gly Ile Val Asp Thr Thr Pro His Pro Pro Thr Arg Glu Thr Leu Phe
        435                 440                 445

Leu Thr Pro Asn Ser Tyr Gln Leu Leu Val Asn Pro Asp Pro Thr Ala
    450                 455                 460

Leu Asp Ile Ala Asn His Tyr Asn Ile Lys Thr Thr Lys Asn Arg Gly
465                 470                 475                 480

Ile Ala Glu Leu Val Glu Asn Leu Asn Ile Val Asp Thr Phe Cys Leu
                485                 490                 495

Lys Thr Gly Leu Lys Phe Asn Lys Leu Leu Glu Leu Thr Met Gln Arg
            500                 505                 510

Asp Tyr Gln Thr Pro Asn Asn Glu Tyr Glu Ser Asn Phe Leu Lys Phe
        515                 520                 525

Gly Ser Glu Lys Tyr Val Pro Val Ser Thr Tyr Gly Ala Lys Phe Leu
    530                 535                 540

Thr Gly Met Glu Lys Ile Pro Leu Trp Val Lys Gln Tyr Lys Gly Ala
545                 550                 555                 560

Lys Val Pro Val Leu Asn Phe Thr Ser Asn Asn Val Val Ser Leu Ala
                565                 570                 575

Gly Arg Ala Glu Lys Leu Ile Arg Leu Ala Gln Asn Thr Gly Leu Ser
            580                 585                 590

Phe Glu Gln Leu Asp Trp Leu Ile Ile Asn Ala Ser Gln Gly Val Met
        595                 600                 605

Glu His Gly Arg Glu Ile Ile Leu Asp Gly Pro Val Leu Glu Ala Ile
    610                 615                 620

Ala Glu Phe Thr Arg Leu His Thr Arg Tyr Gly Ile Thr Thr Asp Met
625                 630                 635                 640

Phe Ala Ala Phe Ile Gly Ala Val Asn Pro Tyr Ala Glu Asn Gly Gln
                645                 650                 655

Lys Ser Phe Tyr Gln Ser Thr Phe Ser Lys Met Asp Glu Ser Phe Thr
            660                 665                 670

Ile Pro Leu Gly Ala Asn Leu Thr Phe Ala Val Glu Lys Gln Gly Glu
        675                 680                 685

Leu Glu Ser Ile Cys Cys Lys Ala Leu Gly Val Thr Pro Asp Glu Leu
    690                 695                 700

Ser Arg Ile Ala Gly Tyr Cys Phe Asp Ala Ala Lys Gly Val Lys Gln
705                 710                 715                 720

Asn Met Asp Glu Ala Ser Phe Gly Gln Leu Leu Arg Met Gly Lys Ile
                725                 730                 735

Pro His Met Leu Gly Leu Ser Phe Thr Glu Ala Glu Val Leu Trp Thr
            740                 745                 750
```

```
Leu Met Ala Asp Gly Lys Asp Thr Phe Leu Arg Ala Ile Gly Gln Thr
        755                 760                 765

Phe Asn Leu Gln Val Leu Ser Ile Ile Arg Asp Thr Glu Arg Val Val
    770                 775                 780

Glu Trp Met Glu Ala His Gln Leu Asp Ile Gly Ala Val Gln Ala Met
785                 790                 795                 800

Val Thr Asn Gln Tyr Ser Gly Thr Ala Thr Pro Thr Leu Tyr Asn Phe
                805                 810                 815

Leu Glu Thr Val Tyr Gln Ser Thr Asn Gly Gly Asp Met Asn Arg Ser
            820                 825                 830

Leu Asn Asn Gln Met Thr Thr Asn Leu Tyr Arg Ala Leu Gly Thr Asn
        835                 840                 845

Phe Asn Leu Lys Val Asn Val Met Thr Gln Val Leu Lys Trp Met Glu
    850                 855                 860

Lys Thr Ile Thr Gly Phe Thr Met Gln Asn Phe Trp Lys Gln Met Gln
865                 870                 875                 880

Glu Tyr Phe Arg Val Asn His Glu Glu Ser Leu Ser Ala Leu Glu Arg
                885                 890                 895

Gln Ala Glu Leu Leu Arg Trp Cys Gln Gln Met Ser Gln Tyr Val Leu
            900                 905                 910

Ile Val Gln Trp Cys Gly Leu Ser Glu Gln Asp Leu Met Leu Val Met
        915                 920                 925

Glu His Pro Glu Arg Val Leu Asp Lys Gln His Val Ser Pro Ala Pro
    930                 935                 940

Ser Met Tyr Leu Leu Leu Val Leu Ser Arg Leu Lys Glu Trp Gln Gln
945                 950                 955                 960

Arg Val Gln Val Ser Ser Asp Glu Ala Met Arg Tyr Phe Glu Gln Val
                965                 970                 975

Asn Val Pro Glu Ile Thr Ser Glu Thr Ala Ile Lys Leu Leu Ala Arg
            980                 985                 990

Ile His Gly Trp Asn Glu Gly Tyr  Thr Thr Ser Met Asn  Asp Tyr Leu
        995                 1000                1005

Leu Glu  Glu Lys Glu Tyr Pro  Lys Asn Phe Glu Gln  Val Phe Arg
    1010                1015                1020

Leu Glu  Ser Trp Val Asn Leu  Gly Arg Gln Phe Asn  Val Gly Ser
    1025                1030                1035

Arg Thr  Leu Gly Glu Leu Val  Asp Met Ala Lys Gln  Asn Glu Thr
    1040                1045                1050

Ala Glu  Asn Asn Asn Leu Ile  Thr Ser Val Ala Gln  Ser Leu Met
    1055                1060                1065

Ala Ala  Ala Ala Gln His Thr  Asn Met Asp Lys Gly  Trp
    1070                1075                1080
```

```
<210> SEQ ID NO 12
<211> LENGTH: 3612
<212> TYPE: DNA
<213> ORGANISM: Bacillus thuringiensis EG4096
<220> FEATURE:
<221> NAME/KEY: CDS
<222> LOCATION: (1)..(3609)
<223> OTHER INFORMATION: TIC905

<400> SEQUENCE: 12

atg tca att gta agt tta tta caa tca att aaa gaa tct cgc agg gat       48
Met Ser Ile Val Ser Leu Leu Gln Ser Ile Lys Glu Ser Arg Arg Asp
1               5                   10                  15
```

-continued

```
gct ttg gtt aat cat tat ctt gcc aat cat acc ccg aag ggg ctt atg       96
Ala Leu Val Asn His Tyr Leu Ala Asn His Thr Pro Lys Gly Leu Met
            20                  25                  30

gat aaa atc aca gat gca gat cgt cta tat gag tat tta ttg tta gat      144
Asp Lys Ile Thr Asp Ala Asp Arg Leu Tyr Glu Tyr Leu Leu Leu Asp
        35                  40                  45

act aag att agt gac ctg gtg aaa aca tca cct gta gca gaa gca atc      192
Thr Lys Ile Ser Asp Leu Val Lys Thr Ser Pro Val Ala Glu Ala Ile
    50                  55                  60

agt agc cta cag cta tac att act cgt tgt agg gaa ggt cag gaa ggg      240
Ser Ser Leu Gln Leu Tyr Ile Thr Arg Cys Arg Glu Gly Gln Glu Gly
65                  70                  75                  80

aga ttg acc tcg aaa ggg aat agt cat ttt gcg cca ggg aaa ttt ctc      288
Arg Leu Thr Ser Lys Gly Asn Ser His Phe Ala Pro Gly Lys Phe Leu
                85                  90                  95

gat aat tgg gat gcc tat aac aag cgt tat gcg act tgg gca ggg aaa      336
Asp Asn Trp Asp Ala Tyr Asn Lys Arg Tyr Ala Thr Trp Ala Gly Lys
            100                 105                 110

gag cgt tta aaa tac tac gca gga agc tac atc aat cca tca ttg cgt      384
Glu Arg Leu Lys Tyr Tyr Ala Gly Ser Tyr Ile Asn Pro Ser Leu Arg
        115                 120                 125

tac aat aaa acg gat ttg ttt caa aat cta gag caa ggt att agt caa      432
Tyr Asn Lys Thr Asp Leu Phe Gln Asn Leu Glu Gln Gly Ile Ser Gln
    130                 135                 140

ggg aga ctg aat gaa gac cat gcg aaa aag gcg ttg caa aac tat ctg      480
Gly Arg Leu Asn Glu Asp His Ala Lys Lys Ala Leu Gln Asn Tyr Leu
145                 150                 155                 160

act gaa tat gaa aca tta gcg gat ttg gaa tat atc agt gtg aat aaa      528
Thr Glu Tyr Glu Thr Leu Ala Asp Leu Glu Tyr Ile Ser Val Asn Lys
                165                 170                 175

ggg aaa gat gaa agt gtc tta ttc ttt att gga cgt acg aaa ata tca      576
Gly Lys Asp Glu Ser Val Leu Phe Phe Ile Gly Arg Thr Lys Ile Ser
            180                 185                 190

cca tat gag tac tac tgg cgc cgc tta aca ata aag aag gat atg aac      624
Pro Tyr Glu Tyr Tyr Trp Arg Arg Leu Thr Ile Lys Lys Asp Met Asn
        195                 200                 205

caa aac ctg att ccg gac aaa tgg tcg cag tgg aaa aag att act gcc      672
Gln Asn Leu Ile Pro Asp Lys Trp Ser Gln Trp Lys Lys Ile Thr Ala
    210                 215                 220

aat att ggt gaa gca gtt gat aac tat gtc gta ccg tac tgg gag aaa      720
Asn Ile Gly Glu Ala Val Asp Asn Tyr Val Val Pro Tyr Trp Glu Lys
225                 230                 235                 240

gat cga ctg cat att caa tgg att tct cga ggg aaa gaa caa gcg gaa      768
Asp Arg Leu His Ile Gln Trp Ile Ser Arg Gly Lys Glu Gln Ala Glu
                245                 250                 255

aat gaa aaa tcc aac gat ata cat att aag aat gat tgg att tta aat      816
Asn Glu Lys Ser Asn Asp Ile His Ile Lys Asn Asp Trp Ile Leu Asn
            260                 265                 270

act tct gaa tta tgg aat tcg ttt agt aag aaa cag gtt ggt cat ttc      864
Thr Ser Glu Leu Trp Asn Ser Phe Ser Lys Lys Gln Val Gly His Phe
        275                 280                 285

gtc aat acg aat aat aat aag tac tgt agc gtc aat gaa aat gaa ttt      912
Val Asn Thr Asn Asn Asn Lys Tyr Cys Ser Val Asn Glu Asn Glu Phe
    290                 295                 300

att att aat aat cca tca caa ttg aag gca acg att aca gca gtt cca      960
Ile Ile Asn Asn Pro Ser Gln Leu Lys Ala Thr Ile Thr Ala Val Pro
305                 310                 315                 320

ggt aaa gga tta gaa gtg ttt tac gaa aaa gac ctt gtt aat atc cag     1008
Gly Lys Gly Leu Glu Val Phe Tyr Glu Lys Asp Leu Val Asn Ile Gln
                325                 330                 335
```

-continued

```
agc aat tca aac tac cta aag ttt cta gat ata aag atg tat tcc gaa      1056
Ser Asn Ser Asn Tyr Leu Lys Phe Leu Asp Ile Lys Met Tyr Ser Glu
            340                 345                 350

gga aag aaa aga tta gta gaa tgt ggt tca tta act agt tac tta cta      1104
Gly Lys Lys Arg Leu Val Glu Cys Gly Ser Leu Thr Ser Tyr Leu Leu
        355                 360                 365

cac ggt tat agc gtt cca agt gga cta tgg cca tgg gaa gag tat tct      1152
His Gly Tyr Ser Val Pro Ser Gly Leu Trp Pro Trp Glu Glu Tyr Ser
    370                 375                 380

tac gca aat tac tat ttt acg tat tat gaa cat atc gtg gat tgc cta      1200
Tyr Ala Asn Tyr Tyr Phe Thr Tyr Tyr Glu His Ile Val Asp Cys Leu
385                 390                 395                 400

gaa aag aca tat ggt tcc att caa tct aat caa tac gtt cca cca aca      1248
Glu Lys Thr Tyr Gly Ser Ile Gln Ser Asn Gln Tyr Val Pro Pro Thr
                405                 410                 415

ggg agt aag ata aaa ggg aaa att aat ctt aag ctc aaa aag aac ata      1296
Gly Ser Lys Ile Lys Gly Lys Ile Asn Leu Lys Leu Lys Lys Asn Ile
            420                 425                 430

gat tta tca tct tta ctg gag aag aat ctt gaa tca cta ttc aac tat      1344
Asp Leu Ser Ser Leu Leu Glu Lys Asn Leu Glu Ser Leu Phe Asn Tyr
        435                 440                 445

gaa att cag act gca aag cat tta ggt ggc aca gag gct ttc tat ggc      1392
Glu Ile Gln Thr Ala Lys His Leu Gly Gly Thr Glu Ala Phe Tyr Gly
    450                 455                 460

cca tat ggc atg tac ttg tgg gaa atc ttt ttc cat att cca ttt ttg      1440
Pro Tyr Gly Met Tyr Leu Trp Glu Ile Phe Phe His Ile Pro Phe Leu
465                 470                 475                 480

atg gcg gtt cgt ttc cag aca gaa caa cgg tat gca ttg gcg gag cgt      1488
Met Ala Val Arg Phe Gln Thr Glu Gln Arg Tyr Ala Leu Ala Glu Arg
                485                 490                 495

tgg ctc aaa ttt att ttt aac agc aca ggt tac cgt gat gga gac ggg      1536
Trp Leu Lys Phe Ile Phe Asn Ser Thr Gly Tyr Arg Asp Gly Asp Gly
            500                 505                 510

aat gtt atc aca gat gaa aaa gga cag gtc cgc tat tgg aac gtg gta      1584
Asn Val Ile Thr Asp Glu Lys Gly Gln Val Arg Tyr Trp Asn Val Val
        515                 520                 525

ccg tta cag gaa gat acg gaa tgg aat gaa acg tta tcc atg gta act      1632
Pro Leu Gln Glu Asp Thr Glu Trp Asn Glu Thr Leu Ser Met Val Thr
    530                 535                 540

gta gat ccg gat gaa att gca atg gcg gat ccc atg cat tat aaa ttg      1680
Val Asp Pro Asp Glu Ile Ala Met Ala Asp Pro Met His Tyr Lys Leu
545                 550                 555                 560

gcg ata ttc atc agt acg tta gat ttc tta att ggc cgt ggt gac aac      1728
Ala Ile Phe Ile Ser Thr Leu Asp Phe Leu Ile Gly Arg Gly Asp Asn
                565                 570                 575

cta tac cgc atg tta gaa cga gat act tta aca gaa gca aag atg tat      1776
Leu Tyr Arg Met Leu Glu Arg Asp Thr Leu Thr Glu Ala Lys Met Tyr
            580                 585                 590

tat atc caa gct agt cag tta cta ggt cct cgt cct gac att cgt gtg      1824
Tyr Ile Gln Ala Ser Gln Leu Leu Gly Pro Arg Pro Asp Ile Arg Val
        595                 600                 605

aat aac agt tgg ccg aat cta aca tta caa ggt gaa gcg gac gcg atg      1872
Asn Asn Ser Trp Pro Asn Leu Thr Leu Gln Gly Glu Ala Asp Ala Met
    610                 615                 620

acc gtt act ccg acg cga ggt aat atg gag gta gat ttg att cgt gtc      1920
Thr Val Thr Pro Thr Arg Gly Asn Met Glu Val Asp Leu Ile Arg Val
625                 630                 635                 640

ttt gaa tct ttt tta caa aaa gaa aat ggt cac ttt ctt ccg cca tac      1968
Phe Glu Ser Phe Leu Gln Lys Glu Asn Gly His Phe Leu Pro Pro Tyr
```

-continued

```
                645                 650                 655

aat gat gaa tta tta gcg tta tgg gat aaa tta gat ctc cgt cta tac     2016
Asn Asp Glu Leu Leu Ala Leu Trp Asp Lys Leu Asp Leu Arg Leu Tyr
            660                 665                 670

aat ttg cgt cat aac cta agc ttg gat ggt cag cca cta cag cta cca     2064
Asn Leu Arg His Asn Leu Ser Leu Asp Gly Gln Pro Leu Gln Leu Pro
        675                 680                 685

tta ttt gct gaa tcg aaa cat cct cga gat tta cag gtg caa cat ggc     2112
Leu Phe Ala Glu Ser Lys His Pro Arg Asp Leu Gln Val Gln His Gly
    690                 695                 700

caa ggc gat gga gta gga gga agt ata gtt tct agt caa agc gtt cag     2160
Gln Gly Asp Gly Val Gly Gly Ser Ile Val Ser Ser Gln Ser Val Gln
705                 710                 715                 720

agt ctg tat cgt ttt ccg att gtg att gat aag gca cgc aat gcg gta     2208
Ser Leu Tyr Arg Phe Pro Ile Val Ile Asp Lys Ala Arg Asn Ala Val
                725                 730                 735

aac agc gtc att caa ttt gga aat acc ttg caa aat gca ttg gaa aag     2256
Asn Ser Val Ile Gln Phe Gly Asn Thr Leu Gln Asn Ala Leu Glu Lys
            740                 745                 750

caa gat gcg gag gca atg act tta ctg ttg caa aag cag caa caa acc     2304
Gln Asp Ala Glu Ala Met Thr Leu Leu Leu Gln Lys Gln Gln Gln Thr
        755                 760                 765

gta ctc aag caa acg cgt gat ata caa gag aaa aat gta gca gcg cta     2352
Val Leu Lys Gln Thr Arg Asp Ile Gln Glu Lys Asn Val Ala Ala Leu
    770                 775                 780

caa tcc aat ctc gaa gca atc atg aca gca aaa aaa ggt gca aag tca     2400
Gln Ser Asn Leu Glu Ala Ile Met Thr Ala Lys Lys Gly Ala Lys Ser
785                 790                 795                 800

aga atg aat cat tat gct ggt tta gta gaa aat tgg atg tct caa aat     2448
Arg Met Asn His Tyr Ala Gly Leu Val Glu Asn Trp Met Ser Gln Asn
                805                 810                 815

gaa acg cat tcc tta aat tta cgt aca aca tcg gca gta ctc cat ggc     2496
Glu Thr His Ser Leu Asn Leu Arg Thr Thr Ser Ala Val Leu His Gly
            820                 825                 830

gct tcc atc gta cct ata gcg gtt gct ggt gct tta gat acg gct cca     2544
Ala Ser Ile Val Pro Ile Ala Val Ala Gly Ala Leu Asp Thr Ala Pro
        835                 840                 845

aat ata ttt ggg tta gct gtt ggc ggt agt cga tgg gga gca gtc agt     2592
Asn Ile Phe Gly Leu Ala Val Gly Gly Ser Arg Trp Gly Ala Val Ser
    850                 855                 860

att gca gta gca caa ggg atg caa att gct gct ggt aca atg gac caa     2640
Ile Ala Val Ala Gln Gly Met Gln Ile Ala Ala Gly Thr Met Asp Gln
865                 870                 875                 880

acg gcg aat atc tta gat gtc agc gag ggc tac cgt cgc cgc cgt gag     2688
Thr Ala Asn Ile Leu Asp Val Ser Glu Gly Tyr Arg Arg Arg Arg Glu
                885                 890                 895

gag tgg atg tta cag cga gac atg gca gaa aat gaa gtc gaa caa ctg     2736
Glu Trp Met Leu Gln Arg Asp Met Ala Glu Asn Glu Val Glu Gln Leu
            900                 905                 910

cag tca caa atc aca gcc tta aaa gaa cag att cag atg gca aag aaa     2784
Gln Ser Gln Ile Thr Ala Leu Lys Glu Gln Ile Gln Met Ala Lys Lys
        915                 920                 925

caa atg gtt cta gca gaa caa gaa caa gcg cat gcg caa gca gtt tat     2832
Gln Met Val Leu Ala Glu Gln Glu Gln Ala His Ala Gln Ala Val Tyr
    930                 935                 940

gac tta caa aga acg cgt ttt act aac caa gcg cta tat aat tgg atg     2880
Asp Leu Gln Arg Thr Arg Phe Thr Asn Gln Ala Leu Tyr Asn Trp Met
945                 950                 955                 960

gtc ggc cgt ctc tcc tgc cta tac cat caa atg tat gac gca aca ttg     2928
```

-continued

```
Val Gly Arg Leu Ser Cys Leu Tyr His Gln Met Tyr Asp Ala Thr Leu
                965                 970                 975

cct ctt tgt ttg atg gct aaa gat gca ttg gta aaa gaa ttg aga aca      2976
Pro Leu Cys Leu Met Ala Lys Asp Ala Leu Val Lys Glu Leu Arg Thr
            980                 985                 990

gat aaa atg aac ggc atc tta acg  gtc cct gcg tgg aat  gac ttg tat    3024
Asp Lys Met Asn Gly Ile Leu Thr  Val Pro Ala Trp Asn  Asp Leu Tyr
        995                 1000                 1005

caa gga  tta tta gct ggt gag  aca ttg cta gta ggt  ctt caa aaa      3069
Gln Gly  Leu Leu Ala Gly Glu  Thr Leu Leu Val Gly  Leu Gln Lys
    1010                 1015                 1020

ctt gag  aat att tgg ctg gag  gaa aat acg cga gga  atg gag gca      3114
Leu Glu  Asn Ile Trp Leu Glu  Glu Asn Thr Arg Gly  Met Glu Ala
    1025                 1030                 1035

gta aaa  aca gtt tct gta gat  acc ctt atg cgt aaa  aag aat cga      3159
Val Lys  Thr Val Ser Val Asp  Thr Leu Met Arg Lys  Lys Asn Arg
    1040                 1045                 1050

gaa tgc  acc ttt gtg gac acg  gta cag aaa gtt ttg  aat ggt aat      3204
Glu Cys  Thr Phe Val Asp Thr  Val Gln Lys Val Leu  Asn Gly Asn
    1055                 1060                 1065

aat gtg  gaa ccg ata aat gga  gtg aaa gtg caa tta  caa aat ggc      3249
Asn Val  Glu Pro Ile Asn Gly  Val Lys Val Gln Leu  Gln Asn Gly
    1070                 1075                 1080

atc ttg  agt gta gct ctt gac  ttg tct tat cta gga  tta gaa aac      3294
Ile Leu  Ser Val Ala Leu Asp  Leu Ser Tyr Leu Gly  Leu Glu Asn
    1085                 1090                 1095

tct tat  aac caa cta gaa aaa  agc cgc aaa atg aaa  acg ata gcg      3339
Ser Tyr  Asn Gln Leu Glu Lys  Ser Arg Lys Met Lys  Thr Ile Ala
    1100                 1105                 1110

gtt acc  ttg cca gcg ctt tta  gga cca tat cag gat  gta gag gct      3384
Val Thr  Leu Pro Ala Leu Leu  Gly Pro Tyr Gln Asp  Val Glu Ala
    1115                 1120                 1125

aca ctg  aca tta ggt gaa gaa  act gtt gca ctt tct  cat ggt gta      3429
Thr Leu  Thr Leu Gly Glu Glu  Thr Val Ala Leu Ser  His Gly Val
    1130                 1135                 1140

gac gac  aca ggc ttg ttt gta  aca gat ttg aat gat  aat aga ttt      3474
Asp Asp  Thr Gly Leu Phe Val  Thr Asp Leu Asn Asp  Asn Arg Phe
    1145                 1150                 1155

tta cct  ttt gag gga gta gat  gtt tta tct ggc aca  tta agt ctg      3519
Leu Pro  Phe Glu Gly Val Asp  Val Leu Ser Gly Thr  Leu Ser Leu
    1160                 1165                 1170

tct att  ttc cgt gcg aat aag  gag gac gag cag cgt  ttc ttc att      3564
Ser Ile  Phe Arg Ala Asn Lys  Glu Asp Glu Gln Arg  Phe Phe Ile
    1175                 1180                 1185

gaa agt  cta aat gat gtc ata  ttc cat att cga tat  gta att aaa      3609
Glu Ser  Leu Asn Asp Val Ile  Phe His Ile Arg Tyr  Val Ile Lys
    1190                 1195                 1200

tga                                                                  3612
```

<210> SEQ ID NO 13
<211> LENGTH: 1203
<212> TYPE: PRT
<213> ORGANISM: Bacillus thuringiensis EG4096

<400> SEQUENCE: 13

```
Met Ser Ile Val Ser Leu Leu Gln Ser Ile Lys Glu Ser Arg Arg Asp
1               5                   10                  15

Ala Leu Val Asn His Tyr Leu Ala Asn His Thr Pro Lys Gly Leu Met
            20                  25                  30
```

-continued

```
Asp Lys Ile Thr Asp Ala Asp Arg Leu Tyr Glu Tyr Leu Leu Leu Asp
        35                  40                  45

Thr Lys Ile Ser Asp Leu Val Lys Thr Ser Pro Val Ala Glu Ala Ile
    50                  55                  60

Ser Ser Leu Gln Leu Tyr Ile Thr Arg Cys Arg Glu Gly Gln Glu Gly
65                  70                  75                  80

Arg Leu Thr Ser Lys Gly Asn Ser His Phe Ala Pro Gly Lys Phe Leu
                85                  90                  95

Asp Asn Trp Asp Ala Tyr Asn Lys Arg Tyr Ala Thr Trp Ala Gly Lys
            100                 105                 110

Glu Arg Leu Lys Tyr Tyr Ala Gly Ser Tyr Ile Asn Pro Ser Leu Arg
        115                 120                 125

Tyr Asn Lys Thr Asp Leu Phe Gln Asn Leu Glu Gln Gly Ile Ser Gln
    130                 135                 140

Gly Arg Leu Asn Glu Asp His Ala Lys Lys Ala Leu Gln Asn Tyr Leu
145                 150                 155                 160

Thr Glu Tyr Glu Thr Leu Ala Asp Leu Glu Tyr Ile Ser Val Asn Lys
                165                 170                 175

Gly Lys Asp Glu Ser Val Leu Phe Phe Ile Gly Arg Thr Lys Ile Ser
            180                 185                 190

Pro Tyr Glu Tyr Tyr Trp Arg Arg Leu Thr Ile Lys Lys Asp Met Asn
        195                 200                 205

Gln Asn Leu Ile Pro Asp Lys Trp Ser Gln Trp Lys Lys Ile Thr Ala
    210                 215                 220

Asn Ile Gly Glu Ala Val Asp Asn Tyr Val Val Pro Tyr Trp Glu Lys
225                 230                 235                 240

Asp Arg Leu His Ile Gln Trp Ile Ser Arg Gly Lys Glu Gln Ala Glu
                245                 250                 255

Asn Glu Lys Ser Asn Asp Ile His Ile Lys Asn Asp Trp Ile Leu Asn
            260                 265                 270

Thr Ser Glu Leu Trp Asn Ser Phe Ser Lys Lys Gln Val Gly His Phe
        275                 280                 285

Val Asn Thr Asn Asn Asn Lys Tyr Cys Ser Val Asn Glu Asn Glu Phe
    290                 295                 300

Ile Ile Asn Asn Pro Ser Gln Leu Lys Ala Thr Ile Thr Ala Val Pro
305                 310                 315                 320

Gly Lys Gly Leu Glu Val Phe Tyr Glu Lys Asp Leu Val Asn Ile Gln
                325                 330                 335

Ser Asn Ser Asn Tyr Leu Lys Phe Leu Asp Ile Lys Met Tyr Ser Glu
            340                 345                 350

Gly Lys Lys Arg Leu Val Glu Cys Gly Ser Leu Thr Ser Tyr Leu Leu
        355                 360                 365

His Gly Tyr Ser Val Pro Ser Gly Leu Trp Pro Trp Glu Glu Tyr Ser
    370                 375                 380

Tyr Ala Asn Tyr Tyr Phe Thr Tyr Tyr Glu His Ile Val Asp Cys Leu
385                 390                 395                 400

Glu Lys Thr Tyr Gly Ser Ile Gln Ser Asn Gln Tyr Val Pro Pro Thr
                405                 410                 415

Gly Ser Lys Ile Lys Gly Lys Ile Asn Leu Lys Leu Lys Lys Asn Ile
            420                 425                 430

Asp Leu Ser Ser Leu Leu Glu Lys Asn Leu Glu Ser Leu Phe Asn Tyr
        435                 440                 445

Glu Ile Gln Thr Ala Lys His Leu Gly Gly Thr Glu Ala Phe Tyr Gly
```

-continued

```
    450                 455                 460

Pro Tyr Gly Met Tyr Leu Trp Glu Ile Phe Phe His Ile Pro Phe Leu
465                 470                 475                 480

Met Ala Val Arg Phe Gln Thr Glu Gln Arg Tyr Ala Leu Ala Glu Arg
                485                 490                 495

Trp Leu Lys Phe Ile Phe Asn Ser Thr Gly Tyr Arg Asp Gly Asp Gly
            500                 505                 510

Asn Val Ile Thr Asp Glu Lys Gly Gln Val Arg Tyr Trp Asn Val Val
        515                 520                 525

Pro Leu Gln Glu Asp Thr Glu Trp Asn Glu Thr Leu Ser Met Val Thr
    530                 535                 540

Val Asp Pro Asp Glu Ile Ala Met Ala Asp Pro Met His Tyr Lys Leu
545                 550                 555                 560

Ala Ile Phe Ile Ser Thr Leu Asp Phe Leu Ile Gly Arg Gly Asp Asn
                565                 570                 575

Leu Tyr Arg Met Leu Glu Arg Asp Thr Leu Thr Glu Ala Lys Met Tyr
            580                 585                 590

Tyr Ile Gln Ala Ser Gln Leu Leu Gly Pro Arg Pro Asp Ile Arg Val
        595                 600                 605

Asn Asn Ser Trp Pro Asn Leu Thr Leu Gln Gly Glu Ala Asp Ala Met
    610                 615                 620

Thr Val Thr Pro Thr Arg Gly Asn Met Glu Val Asp Leu Ile Arg Val
625                 630                 635                 640

Phe Glu Ser Phe Leu Gln Lys Glu Asn Gly His Phe Leu Pro Pro Tyr
                645                 650                 655

Asn Asp Glu Leu Leu Ala Leu Trp Asp Lys Leu Asp Leu Arg Leu Tyr
            660                 665                 670

Asn Leu Arg His Asn Leu Ser Leu Asp Gly Gln Pro Leu Gln Leu Pro
        675                 680                 685

Leu Phe Ala Glu Ser Lys His Pro Arg Asp Leu Gln Val Gln His Gly
    690                 695                 700

Gln Gly Asp Gly Val Gly Gly Ser Ile Val Ser Ser Gln Ser Val Gln
705                 710                 715                 720

Ser Leu Tyr Arg Phe Pro Ile Val Ile Asp Lys Ala Arg Asn Ala Val
                725                 730                 735

Asn Ser Val Ile Gln Phe Gly Asn Thr Leu Gln Asn Ala Leu Glu Lys
            740                 745                 750

Gln Asp Ala Glu Ala Met Thr Leu Leu Leu Gln Lys Gln Gln Gln Thr
        755                 760                 765

Val Leu Lys Gln Thr Arg Asp Ile Gln Glu Lys Asn Val Ala Ala Leu
    770                 775                 780

Gln Ser Asn Leu Glu Ala Ile Met Thr Ala Lys Lys Gly Ala Lys Ser
785                 790                 795                 800

Arg Met Asn His Tyr Ala Gly Leu Val Glu Asn Trp Met Ser Gln Asn
                805                 810                 815

Glu Thr His Ser Leu Asn Leu Arg Thr Thr Ser Ala Val Leu His Gly
            820                 825                 830

Ala Ser Ile Val Pro Ile Ala Val Ala Gly Ala Leu Asp Thr Ala Pro
        835                 840                 845

Asn Ile Phe Gly Leu Ala Val Gly Gly Ser Arg Trp Gly Ala Val Ser
    850                 855                 860

Ile Ala Val Ala Gln Gly Met Gln Ile Ala Ala Gly Thr Met Asp Gln
865                 870                 875                 880
```

-continued

```
Thr Ala Asn Ile Leu Asp Val Ser Glu Gly Tyr Arg Arg Arg Arg Glu
                885                 890                 895

Glu Trp Met Leu Gln Arg Asp Met Ala Glu Asn Glu Val Glu Gln Leu
            900                 905                 910

Gln Ser Gln Ile Thr Ala Leu Lys Glu Gln Ile Gln Met Ala Lys Lys
        915                 920                 925

Gln Met Val Leu Ala Glu Gln Glu Gln Ala His Ala Gln Ala Val Tyr
    930                 935                 940

Asp Leu Gln Arg Thr Arg Phe Thr Asn Gln Ala Leu Tyr Asn Trp Met
945                 950                 955                 960

Val Gly Arg Leu Ser Cys Leu Tyr His Gln Met Tyr Asp Ala Thr Leu
                965                 970                 975

Pro Leu Cys Leu Met Ala Lys Asp Ala Leu Val Lys Glu Leu Arg Thr
            980                 985                 990

Asp Lys Met Asn Gly Ile Leu Thr  Val Pro Ala Trp Asn  Asp Leu Tyr
        995                 1000                1005

Gln Gly  Leu Leu Ala Gly Glu  Thr Leu Leu Val Gly  Leu Gln Lys
    1010                1015                1020

Leu Glu  Asn Ile Trp Leu Glu  Glu Asn Thr Arg Gly  Met Glu Ala
    1025                1030                1035

Val Lys  Thr Val Ser Val Asp  Thr Leu Met Arg Lys  Lys Asn Arg
    1040                1045                1050

Glu Cys  Thr Phe Val Asp Thr  Val Gln Lys Val Leu  Asn Gly Asn
    1055                1060                1065

Asn Val  Glu Pro Ile Asn Gly  Val Lys Val Gln Leu  Gln Asn Gly
    1070                1075                1080

Ile Leu  Ser Val Ala Leu Asp  Leu Ser Tyr Leu Gly  Leu Glu Asn
    1085                1090                1095

Ser Tyr  Asn Gln Leu Glu Lys  Ser Arg Lys Met Lys  Thr Ile Ala
    1100                1105                1110

Val Thr  Leu Pro Ala Leu Leu  Gly Pro Tyr Gln Asp  Val Glu Ala
    1115                1120                1125

Thr Leu  Thr Leu Gly Glu Glu  Thr Val Ala Leu Ser  His Gly Val
    1130                1135                1140

Asp Asp  Thr Gly Leu Phe Val  Thr Asp Leu Asn Asp  Asn Arg Phe
    1145                1150                1155

Leu Pro  Phe Glu Gly Val Asp  Val Leu Ser Gly Thr  Leu Ser Leu
    1160                1165                1170

Ser Ile  Phe Arg Ala Asn Lys  Glu Asp Glu Gln Arg  Phe Phe Ile
    1175                1180                1185

Glu Ser  Leu Asn Asp Val Ile  Phe His Ile Arg Tyr  Val Ile Lys
    1190                1195                1200


<210> SEQ ID NO 14
<211> LENGTH: 4368
<212> TYPE: DNA
<213> ORGANISM: Bacillus thuringiensis EG4096
<220> FEATURE:
<221> NAME/KEY: CDS
<222> LOCATION: (1)..(4365)
<223> OTHER INFORMATION: TIC906

<400> SEQUENCE: 14

atg gaa caa tct agc aat aac gat tta aaa tta ttt tcg cca tct ttg       48
Met Glu Gln Ser Ser Asn Asn Asp Leu Lys Leu Phe Ser Pro Ser Leu
1               5                   10                  15
```

-continued

```
cca aaa ggt ggc gga tct atg aaa gga atg gaa ggg agc atg aca gct       96
Pro Lys Gly Gly Gly Ser Met Lys Gly Met Glu Gly Ser Met Thr Ala
            20                  25                  30

cct ggg tct gat gga gta gca cgt ttt cat gtg cca ctt cct tta acc      144
Pro Gly Ser Asp Gly Val Ala Arg Phe His Val Pro Leu Pro Leu Thr
        35                  40                  45

gct ggt cga cat acg acc cct gat ata agt ctt ttc tat agc agt ggg      192
Ala Gly Arg His Thr Thr Pro Asp Ile Ser Leu Phe Tyr Ser Ser Gly
    50                  55                  60

aac ggc aat ggc ccc ttc ggg att ggt tgg aat atg agt atg atg tcc      240
Asn Gly Asn Gly Pro Phe Gly Ile Gly Trp Asn Met Ser Met Met Ser
65                  70                  75                  80

gtt cgt cga agg acg agc aag gga atc cct tgt tat aca tcg gag gac      288
Val Arg Arg Arg Thr Ser Lys Gly Ile Pro Cys Tyr Thr Ser Glu Asp
                85                  90                  95

cag ttt att ggg cct gac gga gaa gta cta gtt ccg gaa cgt gat gaa      336
Gln Phe Ile Gly Pro Asp Gly Glu Val Leu Val Pro Glu Arg Asp Glu
            100                 105                 110

aca ggt caa ata gtt tct cga cta aca aat cag gca cag ggg att gca      384
Thr Gly Gln Ile Val Ser Arg Leu Thr Asn Gln Ala Gln Gly Ile Ala
        115                 120                 125

ttg gga gaa ctt ttt act gtt acg cgc tat ttc tct cga gtt gaa agt      432
Leu Gly Glu Leu Phe Thr Val Thr Arg Tyr Phe Ser Arg Val Glu Ser
    130                 135                 140

aca ttt cac ttg tta gaa tat tgg gaa gga aaa gaa gaa agt aca aca      480
Thr Phe His Leu Leu Glu Tyr Trp Glu Gly Lys Glu Glu Ser Thr Thr
145                 150                 155                 160

gcg ccg ttt tgg tta ctt cat tcg gcc gat gga caa ctt cac tgc ctg      528
Ala Pro Phe Trp Leu Leu His Ser Ala Asp Gly Gln Leu His Cys Leu
                165                 170                 175

ggt aaa act tca caa gca aga att gct tct tct gat gat cct act aaa      576
Gly Lys Thr Ser Gln Ala Arg Ile Ala Ser Ser Asp Asp Pro Thr Lys
            180                 185                 190

ata gca gaa tgg ttg atg gag gaa tcg tta tct cct ttt ggg gag cac      624
Ile Ala Glu Trp Leu Met Glu Glu Ser Leu Ser Pro Phe Gly Glu His
        195                 200                 205

gtt tat tat cga tat aaa gaa gat agc aaa ggt att tac atg gaa caa      672
Val Tyr Tyr Arg Tyr Lys Glu Asp Ser Lys Gly Ile Tyr Met Glu Gln
    210                 215                 220

aag gat cat gaa tat agt acg aat cgt tat ctt aag tgt gta tat tat      720
Lys Asp His Glu Tyr Ser Thr Asn Arg Tyr Leu Lys Cys Val Tyr Tyr
225                 230                 235                 240

ggg aat aag gtt gca tct cat tca ctt tat cta tgg aaa aag gaa atc      768
Gly Asn Lys Val Ala Ser His Ser Leu Tyr Leu Trp Lys Lys Glu Ile
                245                 250                 255

cct gcg cat gat caa tgg ctt tac ttt gtc cta ttg gac tat ggt gaa      816
Pro Ala His Asp Gln Trp Leu Tyr Phe Val Leu Leu Asp Tyr Gly Glu
            260                 265                 270

aat gat cct tca ttg gat gtt caa cca acc tat aat atg gag ggt acg      864
Asn Asp Pro Ser Leu Asp Val Gln Pro Thr Tyr Asn Met Glu Gly Thr
        275                 280                 285

tgg tta gca cgt aca gac tgt ttt tct cgt tat gaa tat gga ttt gaa      912
Trp Leu Ala Arg Thr Asp Cys Phe Ser Arg Tyr Glu Tyr Gly Phe Glu
    290                 295                 300

gtc cga act tgt cgc ttg tgt cgc caa atc ttg atg ttt cat aac ttt      960
Val Arg Thr Cys Arg Leu Cys Arg Gln Ile Leu Met Phe His Asn Phe
305                 310                 315                 320

gca gaa ctt gga ggg gac ccg act ctc gta tgg cgt atg caa ttg gaa     1008
Ala Glu Leu Gly Gly Asp Pro Thr Leu Val Trp Arg Met Gln Leu Glu
```

-continued

```
            325                 330                 335

tat gat gaa aat gca gcg gtc tcg atg tta agt gct gta caa cag cta     1056
Tyr Asp Glu Asn Ala Ala Val Ser Met Leu Ser Ala Val Gln Gln Leu
            340                 345                 350

gca tat gaa aaa gat ggt aca att aaa agt tta cca cca tta gaa ttt     1104
Ala Tyr Glu Lys Asp Gly Thr Ile Lys Ser Leu Pro Pro Leu Glu Phe
        355                 360                 365

gat tat acg caa ttt gaa atc aaa gaa gtg atg aat tgg gaa cca ttc     1152
Asp Tyr Thr Gln Phe Glu Ile Lys Glu Val Met Asn Trp Glu Pro Phe
    370                 375                 380

ctc acg gta cca gaa tgg aat cgt gga gag cac tat caa ttg gtt gat     1200
Leu Thr Val Pro Glu Trp Asn Arg Gly Glu His Tyr Gln Leu Val Asp
385                 390                 395                 400

ctg tat ggt gag ggt att cca ggt ttg tta tat caa aat aag gat cat     1248
Leu Tyr Gly Glu Gly Ile Pro Gly Leu Leu Tyr Gln Asn Lys Asp His
                405                 410                 415

tgg cat tat cgt tcg cct gta cga agt gaa gca acc gat ggg atc atg     1296
Trp His Tyr Arg Ser Pro Val Arg Ser Glu Ala Thr Asp Gly Ile Met
            420                 425                 430

tac gaa act tgg aaa cct ctt cct aat att cca act cat aca gag aat     1344
Tyr Glu Thr Trp Lys Pro Leu Pro Asn Ile Pro Thr His Thr Glu Asn
        435                 440                 445

ggg atg tta cta gat atg aat ggg aat ggg tat ttg gat tgg ttt gta     1392
Gly Met Leu Leu Asp Met Asn Gly Asn Gly Tyr Leu Asp Trp Phe Val
    450                 455                 460

ata caa tca ggt gtt agg gga aca tat acg atg aaa ccg aac cat aca     1440
Ile Gln Ser Gly Val Arg Gly Thr Tyr Thr Met Lys Pro Asn His Thr
465                 470                 475                 480

tgg tct aac ttt att ccc att aaa tcg ctg cca aca gaa ttt ttt cat     1488
Trp Ser Asn Phe Ile Pro Ile Lys Ser Leu Pro Thr Glu Phe Phe His
                485                 490                 495

cct aaa gca cag ctt tct aat gta act gga tca gga tta aca gat ctg     1536
Pro Lys Ala Gln Leu Ser Asn Val Thr Gly Ser Gly Leu Thr Asp Leu
            500                 505                 510

atc atg att ggt cca aaa agt gtt cgg ttt tac gct gga aaa gaa tta     1584
Ile Met Ile Gly Pro Lys Ser Val Arg Phe Tyr Ala Gly Lys Glu Leu
        515                 520                 525

gga ttt aaa cac gca tgt gaa gtg tgg caa aaa gca ggc att cat ctt     1632
Gly Phe Lys His Ala Cys Glu Val Trp Gln Lys Ala Gly Ile His Leu
    530                 535                 540

ccc att caa gat gtc aat aag aaa gaa ctt gta gca ttt agt gat gta     1680
Pro Ile Gln Asp Val Asn Lys Lys Glu Leu Val Ala Phe Ser Asp Val
545                 550                 555                 560

ata ggc tct gga caa tcc cat ttg gtt cgg gta aat tac gat ggc gtt     1728
Ile Gly Ser Gly Gln Ser His Leu Val Arg Val Asn Tyr Asp Gly Val
                565                 570                 575

aca tgt tgg ccg aac ctt ggt aac ggc atg ttc ggc caa cca ctt ggt     1776
Thr Cys Trp Pro Asn Leu Gly Asn Gly Met Phe Gly Gln Pro Leu Gly
            580                 585                 590

att ccg gga ttt gct ttc aat gaa gac gag ttt gac cct gaa cgt gta     1824
Ile Pro Gly Phe Ala Phe Asn Glu Asp Glu Phe Asp Pro Glu Arg Val
        595                 600                 605

tat ttt gct gat ctt gat ggc tca ggc act tct gat ttg gtt tat gct     1872
Tyr Phe Ala Asp Leu Asp Gly Ser Gly Thr Ser Asp Leu Val Tyr Ala
    610                 615                 620

tct cag cgt gct att ctc atc tat caa aat ctt tct ggg aat aga ttt     1920
Ser Gln Arg Ala Ile Leu Ile Tyr Gln Asn Leu Ser Gly Asn Arg Phe
625                 630                 635                 640

gct gct ccg gta aag att ccg ctt cct gat ggt gtt tat ttt gat aat     1968
```

-continued

```
Ala Ala Pro Val Lys Ile Pro Leu Pro Asp Gly Val Tyr Phe Asp Asn
            645                 650                 655

cta tgt cac ctt cag ttt gct gat att ctt gga aaa ggt gtg tcc aac      2016
Leu Cys His Leu Gln Phe Ala Asp Ile Leu Gly Lys Gly Val Ser Asn
        660                 665                 670

ata gtg ttg cat att ccc cac atg cat tct cgt acc tgg tat ttg gat      2064
Ile Val Leu His Ile Pro His Met His Ser Arg Thr Trp Tyr Leu Asp
    675                 680                 685

tta tgt tcg agt aag cca tat cta tta aaa agc act agc aat aat tta      2112
Leu Cys Ser Ser Lys Pro Tyr Leu Leu Lys Ser Thr Ser Asn Asn Leu
    690                 695                 700

ggt gct tct agt ttg ttt cat tat cga agc tct gcg cag tat tgg ctg      2160
Gly Ala Ser Ser Leu Phe His Tyr Arg Ser Ser Ala Gln Tyr Trp Leu
705                 710                 715                 720

gat gaa aag aaa atg aat tcg tca gct gtt tgc aaa ttg cca ttt tca      2208
Asp Glu Lys Lys Met Asn Ser Ser Ala Val Cys Lys Leu Pro Phe Ser
            725                 730                 735

atc caa ctt gta tct ggt gta gaa aca ttt gat gag att agt ggc aat      2256
Ile Gln Leu Val Ser Gly Val Glu Thr Phe Asp Glu Ile Ser Gly Asn
        740                 745                 750

gtc aaa aat cag gaa ttt act tat cga tat ggc atg tac gat cga gct      2304
Val Lys Asn Gln Glu Phe Thr Tyr Arg Tyr Gly Met Tyr Asp Arg Ala
    755                 760                 765

gaa agg gag ttt tca ggg ttt ggt tat att gaa gta aga gag agt gag      2352
Glu Arg Glu Phe Ser Gly Phe Gly Tyr Ile Glu Val Arg Glu Ser Glu
    770                 775                 780

cta aac cct cag aaa ccc gct agt tgt aat gta tca cca gta ctg act      2400
Leu Asn Pro Gln Lys Pro Ala Ser Cys Asn Val Ser Pro Val Leu Thr
785                 790                 795                 800

cgt act tgg tat cat aca ggg caa aaa gaa gac gag aat cgg gct ttt      2448
Arg Thr Trp Tyr His Thr Gly Gln Lys Glu Asp Glu Asn Arg Ala Phe
            805                 810                 815

tat cag tgt tgg aga ggt gat aat gat gca att tgg tta aca tca acc      2496
Tyr Gln Cys Trp Arg Gly Asp Asn Asp Ala Ile Trp Leu Thr Ser Thr
        820                 825                 830

cga ttt act gta ttt gat tca gaa aca gga gag gat gta cgg tta gag      2544
Arg Phe Thr Val Phe Asp Ser Glu Thr Gly Glu Asp Val Arg Leu Glu
        835                 840                 845

gca cga act gat aat caa gaa tat tgg cta tac cga tgt ttg aaa gga      2592
Ala Arg Thr Asp Asn Gln Glu Tyr Trp Leu Tyr Arg Cys Leu Lys Gly
    850                 855                 860

atg cct ctt tat act gaa att ttt gat gaa ggc ggt tac gaa tct cat      2640
Met Pro Leu Tyr Thr Glu Ile Phe Asp Glu Gly Gly Tyr Glu Ser His
865                 870                 875                 880

cct tat caa gtc gag agc ttc cgt tat caa gta aga ttg att caa agt      2688
Pro Tyr Gln Val Glu Ser Phe Arg Tyr Gln Val Arg Leu Ile Gln Ser
            885                 890                 895

acg gat tcg gaa tgt gtt gta ctg ccg tta caa ctg gaa ctc ttg tct      2736
Thr Asp Ser Glu Cys Val Val Leu Pro Leu Gln Leu Glu Leu Leu Ser
        900                 905                 910

tat aac tat gag aaa atc cct tct gat cca cag tgt aca cag caa att      2784
Tyr Asn Tyr Glu Lys Ile Pro Ser Asp Pro Gln Cys Thr Gln Gln Ile
    915                 920                 925

caa caa gtt ttt gat gaa tat gga ttt tca aca caa agc gta acg att      2832
Gln Gln Val Phe Asp Glu Tyr Gly Phe Ser Thr Gln Ser Val Thr Ile
    930                 935                 940

caa tac ccg cgt cga gtc cag cca cct agt aac ccg tat cct gaa aca      2880
Gln Tyr Pro Arg Arg Val Gln Pro Pro Ser Asn Pro Tyr Pro Glu Thr
945                 950                 955                 960
```

-continued

```
tta cca gat acg agt tgg gac agt agc tac gat tca caa caa atg gtg     2928
Leu Pro Asp Thr Ser Trp Asp Ser Ser Tyr Asp Ser Gln Gln Met Val
                965                 970                 975

cta cgg ctt aca aga caa aga gaa aaa aaa tac cat ctt tca gat tct     2976
Leu Arg Leu Thr Arg Gln Arg Glu Lys Lys Tyr His Leu Ser Asp Ser
            980                 985                 990

gaa aat tgg cga tta gga ata cca  cat caa aac agg atg  gat att ttc   3024
Glu Asn Trp Arg Leu Gly Ile Pro  His Gln Asn Arg Met  Asp Ile Phe
        995                 1000                 1005

acc tat  cct gtt gcc agt gtc  cct gcc gaa ggc gta  agt ttc gag      3069
Thr Tyr  Pro Val Ala Ser Val  Pro Ala Glu Gly Val  Ser Phe Glu
    1010                 1015                 1020

aaa ttg  aag aag gat ggg gtt  tta aac gtt cct gtg  caa gaa cag      3114
Lys Leu  Lys Lys Asp Gly Val  Leu Asn Val Pro Val  Gln Glu Gln
    1025                 1030                 1035

gct tat  ggt gga cag aca gaa  atc att tat atc ggt  gag gga aaa      3159
Ala Tyr  Gly Gly Gln Thr Glu  Ile Ile Tyr Ile Gly  Glu Gly Lys
    1040                 1045                 1050

cca gac  gta agg gca ttg gtg  tat tac aca aga aca  gca att ctt      3204
Pro Asp  Val Arg Ala Leu Val  Tyr Tyr Thr Arg Thr  Ala Ile Leu
    1055                 1060                 1065

gac gaa  acc tgt tta cag gcc  tat aaa gga acg ctt  act cag gaa      3249
Asp Glu  Thr Cys Leu Gln Ala  Tyr Lys Gly Thr Leu  Thr Gln Glu
    1070                 1075                 1080

cga tta  gat aca ctc ctt aca  tct tct ggc tat aaa  aaa agt aag      3294
Arg Leu  Asp Thr Leu Leu Thr  Ser Ser Gly Tyr Lys  Lys Ser Lys
    1085                 1090                 1095

cgt ata  tta ggt aag gaa ggg  gaa aaa gat gta tta  gta gca gag      3339
Arg Ile  Leu Gly Lys Glu Gly  Glu Lys Asp Val Leu  Val Ala Glu
    1100                 1105                 1110

ttg gga  ttc tct cgt tat aaa  gat gcg gct ggt ttt  tac caa gta      3384
Leu Gly  Phe Ser Arg Tyr Lys  Asp Ala Ala Gly Phe  Tyr Gln Val
    1115                 1120                 1125

tcg gct  cag cga gcc tct tgt  tta acc gga gaa caa  gtg ctt ttt      3429
Ser Ala  Gln Arg Ala Ser Cys  Leu Thr Gly Glu Gln  Val Leu Phe
    1130                 1135                 1140

tgg gat  gat aat tac tgt gtg  att aat tct gta gaa  gac gct gtg      3474
Trp Asp  Asp Asn Tyr Cys Val  Ile Asn Ser Val Glu  Asp Ala Val
    1145                 1150                 1155

aaa aat  aaa acc cag att gca  tat gat tat cga ttt  ttg caa gcc      3519
Lys Asn  Lys Thr Gln Ile Ala  Tyr Asp Tyr Arg Phe  Leu Gln Ala
    1160                 1165                 1170

aat caa  att aca gat gcc aat  aac aat ata agt caa  gtg cac ttg      3564
Asn Gln  Ile Thr Asp Ala Asn  Asn Asn Ile Ser Gln  Val His Leu
    1175                 1180                 1185

gat gct  ctt ggc cgg gta atc  tat agt cgt atc tgg  ggg aca gaa      3609
Asp Ala  Leu Gly Arg Val Ile  Tyr Ser Arg Ile Trp  Gly Thr Glu
    1190                 1195                 1200

gaa gga  aac gaa gta ggt ttt  cgg cca gaa tta gaa  ttt tta cca      3654
Glu Gly  Asn Glu Val Gly Phe  Arg Pro Glu Leu Glu  Phe Leu Pro
    1205                 1210                 1215

cct gaa  acg att gaa caa gca  ctg tca tta caa gct  cct atg cca      3699
Pro Glu  Thr Ile Glu Gln Ala  Leu Ser Leu Gln Ala  Pro Met Pro
    1220                 1225                 1230

gtt tct  tct tgc ttt gta tat  gat aca tat agt tgg  atg gga acg      3744
Val Ser  Ser Cys Phe Val Tyr  Asp Thr Tyr Ser Trp  Met Gly Thr
    1235                 1240                 1245

ata ttt  cct aag aaa ctt tct  gac ctt atc tcg gat  ggc gca aaa      3789
Ile Phe  Pro Lys Lys Leu Ser  Asp Leu Ile Ser Asp  Gly Ala Lys
    1250                 1255                 1260
```

```
cag tgg  gaa ttt cta ata gct  aac cgt ttt att aca  aga gat ggc      3834
Gln Trp  Glu Phe Leu Ile Ala  Asn Arg Phe Ile Thr  Arg Asp Gly
    1265                 1270                 1275

aga atc  aga gct cgt gga cga  tac cca tgg cta tca  cat caa tct      3879
Arg Ile  Arg Ala Arg Gly Arg  Tyr Pro Trp Leu Ser  His Gln Ser
    1280                 1285                 1290

ata cca  cat gct gtt gtc aat  ctg ttg agt gat gtc  aat cgc aat      3924
Ile Pro  His Ala Val Val Asn  Leu Leu Ser Asp Val  Asn Arg Asn
    1295                 1300                 1305

ccg ccg  cat acc tta ctg tta  cat gta gat cgt tat  cca aat gac      3969
Pro Pro  His Thr Leu Leu Leu  His Val Asp Arg Tyr  Pro Asn Asp
    1310                 1315                 1320

cca tct  cag caa atg caa gta  agc att gct ttt acc  gat gga ttt      4014
Pro Ser  Gln Gln Met Gln Val  Ser Ile Ala Phe Thr  Asp Gly Phe
    1325                 1330                 1335

ggg cgg  cca atc cag att tct  caa aga gca gat tca  aaa att gac      4059
Gly Arg  Pro Ile Gln Ile Ser  Gln Arg Ala Asp Ser  Lys Ile Asp
    1340                 1345                 1350

gat aaa  gaa aag tct gtt gca  cat aaa agt gaa gcc  cgt tgg gct      4104
Asp Lys  Glu Lys Ser Val Ala  His Lys Ser Glu Ala  Arg Trp Ala
    1355                 1360                 1365

att tta  gag cgt gtt gat tat  ggt gga aaa gaa tct  gtg att cga      4149
Ile Leu  Glu Arg Val Asp Tyr  Gly Gly Lys Glu Ser  Val Ile Arg
    1370                 1375                 1380

agt ttt  cag cct ttt tat ttt  cat gat tgg cac tat  att cct aat      4194
Ser Phe  Gln Pro Phe Tyr Phe  His Asp Trp His Tyr  Ile Pro Asn
    1385                 1390                 1395

aaa tcc  gtt agc agc tct atg  tac gca aca aac tat  tat tat gat      4239
Lys Ser  Val Ser Ser Ser Met  Tyr Ala Thr Asn Tyr  Tyr Tyr Asp
    1400                 1405                 1410

gct tta  tca cgt gaa att gga  aag gtg aat gca aaa  gga tat gaa      4284
Ala Leu  Ser Arg Glu Ile Gly  Lys Val Asn Ala Lys  Gly Tyr Glu
    1415                 1420                 1425

aca aaa  aat ttg ttt tat cct  tgg ttt acg ata act  tta gat gaa      4329
Thr Lys  Asn Leu Phe Tyr Pro  Trp Phe Thr Ile Thr  Leu Asp Glu
    1430                 1435                 1440

aac gat  atg tgg agc aat aga  atg gtt gaa gtg gaa  tga              4368
Asn Asp  Met Trp Ser Asn Arg  Met Val Glu Val Glu
    1445                 1450                 1455


<210> SEQ ID NO 15
<211> LENGTH: 1455
<212> TYPE: PRT
<213> ORGANISM: Bacillus thuringiensis EG4096

<400> SEQUENCE: 15

Met Glu Gln Ser Ser Asn Asn Asp Leu Lys Leu Phe Ser Pro Ser Leu
1               5                   10                  15

Pro Lys Gly Gly Gly Ser Met Lys Gly Met Glu Gly Ser Met Thr Ala
            20                  25                  30

Pro Gly Ser Asp Gly Val Ala Arg Phe His Val Pro Leu Pro Leu Thr
        35                  40                  45

Ala Gly Arg His Thr Thr Pro Asp Ile Ser Leu Phe Tyr Ser Ser Gly
    50                  55                  60

Asn Gly Asn Gly Pro Phe Gly Ile Gly Trp Asn Met Ser Met Met Ser
65                  70                  75                  80

Val Arg Arg Arg Thr Ser Lys Gly Ile Pro Cys Tyr Thr Ser Glu Asp
                85                  90                  95
```

-continued

```
Gln Phe Ile Gly Pro Asp Gly Glu Val Leu Val Pro Glu Arg Asp Glu
            100                 105                 110

Thr Gly Gln Ile Val Ser Arg Leu Thr Asn Gln Ala Gln Gly Ile Ala
        115                 120                 125

Leu Gly Glu Leu Phe Thr Val Thr Arg Tyr Phe Ser Arg Val Glu Ser
    130                 135                 140

Thr Phe His Leu Leu Glu Tyr Trp Glu Gly Lys Glu Glu Ser Thr Thr
145                 150                 155                 160

Ala Pro Phe Trp Leu Leu His Ser Ala Asp Gly Gln Leu His Cys Leu
                165                 170                 175

Gly Lys Thr Ser Gln Ala Arg Ile Ala Ser Ser Asp Asp Pro Thr Lys
            180                 185                 190

Ile Ala Glu Trp Leu Met Glu Glu Ser Leu Ser Pro Phe Gly Glu His
        195                 200                 205

Val Tyr Tyr Arg Tyr Lys Glu Asp Ser Lys Gly Ile Tyr Met Glu Gln
    210                 215                 220

Lys Asp His Glu Tyr Ser Thr Asn Arg Tyr Leu Lys Cys Val Tyr Tyr
225                 230                 235                 240

Gly Asn Lys Val Ala Ser His Ser Leu Tyr Leu Trp Lys Lys Glu Ile
                245                 250                 255

Pro Ala His Asp Gln Trp Leu Tyr Phe Val Leu Leu Asp Tyr Gly Glu
            260                 265                 270

Asn Asp Pro Ser Leu Asp Val Gln Pro Thr Tyr Asn Met Glu Gly Thr
        275                 280                 285

Trp Leu Ala Arg Thr Asp Cys Phe Ser Arg Tyr Glu Tyr Gly Phe Glu
    290                 295                 300

Val Arg Thr Cys Arg Leu Cys Arg Gln Ile Leu Met Phe His Asn Phe
305                 310                 315                 320

Ala Glu Leu Gly Gly Asp Pro Thr Leu Val Trp Arg Met Gln Leu Glu
                325                 330                 335

Tyr Asp Glu Asn Ala Ala Val Ser Met Leu Ser Ala Val Gln Gln Leu
            340                 345                 350

Ala Tyr Glu Lys Asp Gly Thr Ile Lys Ser Leu Pro Pro Leu Glu Phe
        355                 360                 365

Asp Tyr Thr Gln Phe Glu Ile Lys Glu Val Met Asn Trp Glu Pro Phe
    370                 375                 380

Leu Thr Val Pro Glu Trp Asn Arg Gly Glu His Tyr Gln Leu Val Asp
385                 390                 395                 400

Leu Tyr Gly Glu Gly Ile Pro Gly Leu Leu Tyr Gln Asn Lys Asp His
                405                 410                 415

Trp His Tyr Arg Ser Pro Val Arg Ser Glu Ala Thr Asp Gly Ile Met
            420                 425                 430

Tyr Glu Thr Trp Lys Pro Leu Pro Asn Ile Pro Thr His Thr Glu Asn
        435                 440                 445

Gly Met Leu Leu Asp Met Asn Gly Asn Gly Tyr Leu Asp Trp Phe Val
    450                 455                 460

Ile Gln Ser Gly Val Arg Gly Thr Tyr Thr Met Lys Pro Asn His Thr
465                 470                 475                 480

Trp Ser Asn Phe Ile Pro Ile Lys Ser Leu Pro Thr Glu Phe Phe His
                485                 490                 495

Pro Lys Ala Gln Leu Ser Asn Val Thr Gly Ser Gly Leu Thr Asp Leu
            500                 505                 510

Ile Met Ile Gly Pro Lys Ser Val Arg Phe Tyr Ala Gly Lys Glu Leu
```

-continued

```
        515                 520                 525

Gly Phe Lys His Ala Cys Glu Val Trp Gln Lys Ala Gly Ile His Leu
    530                 535                 540

Pro Ile Gln Asp Val Asn Lys Lys Glu Leu Val Ala Phe Ser Asp Val
545                 550                 555                 560

Ile Gly Ser Gly Gln Ser His Leu Val Arg Val Asn Tyr Asp Gly Val
                565                 570                 575

Thr Cys Trp Pro Asn Leu Gly Asn Gly Met Phe Gly Gln Pro Leu Gly
            580                 585                 590

Ile Pro Gly Phe Ala Phe Asn Glu Asp Glu Phe Asp Pro Glu Arg Val
        595                 600                 605

Tyr Phe Ala Asp Leu Asp Gly Ser Gly Thr Ser Asp Leu Val Tyr Ala
    610                 615                 620

Ser Gln Arg Ala Ile Leu Ile Tyr Gln Asn Leu Ser Gly Asn Arg Phe
625                 630                 635                 640

Ala Ala Pro Val Lys Ile Pro Leu Pro Asp Gly Val Tyr Phe Asp Asn
                645                 650                 655

Leu Cys His Leu Gln Phe Ala Asp Ile Leu Gly Lys Gly Val Ser Asn
            660                 665                 670

Ile Val Leu His Ile Pro His Met His Ser Arg Thr Trp Tyr Leu Asp
        675                 680                 685

Leu Cys Ser Ser Lys Pro Tyr Leu Leu Lys Ser Thr Ser Asn Asn Leu
    690                 695                 700

Gly Ala Ser Ser Leu Phe His Tyr Arg Ser Ser Ala Gln Tyr Trp Leu
705                 710                 715                 720

Asp Glu Lys Lys Met Asn Ser Ser Ala Val Cys Lys Leu Pro Phe Ser
                725                 730                 735

Ile Gln Leu Val Ser Gly Val Glu Thr Phe Asp Glu Ile Ser Gly Asn
            740                 745                 750

Val Lys Asn Gln Glu Phe Thr Tyr Arg Tyr Gly Met Tyr Asp Arg Ala
        755                 760                 765

Glu Arg Glu Phe Ser Gly Phe Gly Tyr Ile Glu Val Arg Glu Ser Glu
    770                 775                 780

Leu Asn Pro Gln Lys Pro Ala Ser Cys Asn Val Ser Pro Val Leu Thr
785                 790                 795                 800

Arg Thr Trp Tyr His Thr Gly Gln Lys Glu Asp Glu Asn Arg Ala Phe
                805                 810                 815

Tyr Gln Cys Trp Arg Gly Asp Asn Asp Ala Ile Trp Leu Thr Ser Thr
            820                 825                 830

Arg Phe Thr Val Phe Asp Ser Glu Thr Gly Glu Asp Val Arg Leu Glu
        835                 840                 845

Ala Arg Thr Asp Asn Gln Glu Tyr Trp Leu Tyr Arg Cys Leu Lys Gly
    850                 855                 860

Met Pro Leu Tyr Thr Glu Ile Phe Asp Glu Gly Gly Tyr Glu Ser His
865                 870                 875                 880

Pro Tyr Gln Val Glu Ser Phe Arg Tyr Gln Val Arg Leu Ile Gln Ser
                885                 890                 895

Thr Asp Ser Glu Cys Val Val Leu Pro Leu Gln Leu Glu Leu Leu Ser
            900                 905                 910

Tyr Asn Tyr Glu Lys Ile Pro Ser Asp Pro Gln Cys Thr Gln Gln Ile
        915                 920                 925

Gln Gln Val Phe Asp Glu Tyr Gly Phe Ser Thr Gln Ser Val Thr Ile
    930                 935                 940
```

-continued

```
Gln Tyr Pro Arg Arg Val Gln Pro Pro Ser Asn Pro Tyr Pro Glu Thr
945                 950                 955                 960

Leu Pro Asp Thr Ser Trp Asp Ser Ser Tyr Asp Ser Gln Gln Met Val
                965                 970                 975

Leu Arg Leu Thr Arg Gln Arg Glu Lys Lys Tyr His Leu Ser Asp Ser
            980                 985                 990

Glu Asn Trp Arg Leu Gly Ile Pro  His Gln Asn Arg Met  Asp Ile Phe
        995                 1000                 1005

Thr Tyr  Pro Val Ala Ser Val  Pro Ala Glu Gly Val  Ser Phe Glu
    1010                 1015                 1020

Lys Leu  Lys Lys Asp Gly Val  Leu Asn Val Pro Val  Gln Glu Gln
    1025                 1030                 1035

Ala Tyr  Gly Gly Gln Thr Glu  Ile Ile Tyr Ile Gly  Glu Gly Lys
    1040                 1045                 1050

Pro Asp  Val Arg Ala Leu Val  Tyr Tyr Thr Arg Thr  Ala Ile Leu
    1055                 1060                 1065

Asp Glu  Thr Cys Leu Gln Ala  Tyr Lys Gly Thr Leu  Thr Gln Glu
    1070                 1075                 1080

Arg Leu  Asp Thr Leu Leu Thr  Ser Ser Gly Tyr Lys  Lys Ser Lys
    1085                 1090                 1095

Arg Ile  Leu Gly Lys Glu Gly  Glu Lys Asp Val Leu  Val Ala Glu
    1100                 1105                 1110

Leu Gly  Phe Ser Arg Tyr Lys  Asp Ala Ala Gly Phe  Tyr Gln Val
    1115                 1120                 1125

Ser Ala  Gln Arg Ala Ser Cys  Leu Thr Gly Glu Gln  Val Leu Phe
    1130                 1135                 1140

Trp Asp  Asp Asn Tyr Cys Val  Ile Asn Ser Val Glu  Asp Ala Val
    1145                 1150                 1155

Lys Asn  Lys Thr Gln Ile Ala  Tyr Asp Tyr Arg Phe  Leu Gln Ala
    1160                 1165                 1170

Asn Gln  Ile Thr Asp Ala Asn  Asn Asn Ile Ser Gln  Val His Leu
    1175                 1180                 1185

Asp Ala  Leu Gly Arg Val Ile  Tyr Ser Arg Ile Trp  Gly Thr Glu
    1190                 1195                 1200

Glu Gly  Asn Glu Val Gly Phe  Arg Pro Glu Leu Glu  Phe Leu Pro
    1205                 1210                 1215

Pro Glu  Thr Ile Glu Gln Ala  Leu Ser Leu Gln Ala  Pro Met Pro
    1220                 1225                 1230

Val Ser  Ser Cys Phe Val Tyr  Asp Thr Tyr Ser Trp  Met Gly Thr
    1235                 1240                 1245

Ile Phe  Pro Lys Lys Leu Ser  Asp Leu Ile Ser Asp  Gly Ala Lys
    1250                 1255                 1260

Gln Trp  Glu Phe Leu Ile Ala  Asn Arg Phe Ile Thr  Arg Asp Gly
    1265                 1270                 1275

Arg Ile  Arg Ala Arg Gly Arg  Tyr Pro Trp Leu Ser  His Gln Ser
    1280                 1285                 1290

Ile Pro  His Ala Val Val Asn  Leu Leu Ser Asp Val  Asn Arg Asn
    1295                 1300                 1305

Pro Pro  His Thr Leu Leu Leu  His Val Asp Arg Tyr  Pro Asn Asp
    1310                 1315                 1320

Pro Ser  Gln Gln Met Gln Val  Ser Ile Ala Phe Thr  Asp Gly Phe
    1325                 1330                 1335
```

-continued

```
Gly Arg  Pro Ile Gln Ile Ser  Gln Arg Ala Asp Ser  Lys Ile Asp
    1340                 1345                 1350

Asp Lys  Glu Lys Ser Val Ala  His Lys Ser Glu Ala  Arg Trp Ala
    1355                 1360                 1365

Ile Leu  Glu Arg Val Asp Tyr  Gly Gly Lys Glu Ser  Val Ile Arg
    1370                 1375                 1380

Ser Phe  Gln Pro Phe Tyr Phe  His Asp Trp His Tyr  Ile Pro Asn
    1385                 1390                 1395

Lys Ser  Val Ser Ser Ser Met  Tyr Ala Thr Asn Tyr  Tyr Tyr Asp
    1400                 1405                 1410

Ala Leu  Ser Arg Glu Ile Gly  Lys Val Asn Ala Lys  Gly Tyr Glu
    1415                 1420                 1425

Thr Lys  Asn Leu Phe Tyr Pro  Trp Phe Thr Ile Thr  Leu Asp Glu
    1430                 1435                 1440

Asn Asp  Met Trp Ser Asn Arg  Met Val Glu Val Glu
    1445                 1450                 1455


<210> SEQ ID NO 16
<211> LENGTH: 2784
<212> TYPE: DNA
<213> ORGANISM: Bacillus thuringiensis EG4096
<220> FEATURE:
<221> NAME/KEY: CDS
<222> LOCATION: (1)..(2784)
<223> OTHER INFORMATION: TIC912

<400> SEQUENCE: 16

atg aat atg aca tct cta tat tat aat acc cca act att tcc gtc atc       48
Met Asn Met Thr Ser Leu Tyr Tyr Asn Thr Pro Thr Ile Ser Val Ile
1               5                   10                  15

gac aac aga aat tta caa gtg cgt aca ctt gaa tac aat cga gtt gca       96
Asp Asn Arg Asn Leu Gln Val Arg Thr Leu Glu Tyr Asn Arg Val Ala
            20                  25                  30

gcg gga gaa cca gtg gat gaa tat atc cat cga aat tca tat acg ctc      144
Ala Gly Glu Pro Val Asp Glu Tyr Ile His Arg Asn Ser Tyr Thr Leu
        35                  40                  45

atg ggg cat atg gag agt agc atg gat cct cgg tta ttt tca ctg cat      192
Met Gly His Met Glu Ser Ser Met Asp Pro Arg Leu Phe Ser Leu His
    50                  55                  60

gag gac gat aag gag aca ttg ccg aac ctg aag aac atc aca tct gta      240
Glu Asp Asp Lys Glu Thr Leu Pro Asn Leu Lys Asn Ile Thr Ser Val
65                  70                  75                  80

aga gga gag gtt ctc tat acc aaa agt gtg gat gct agt aga aag att      288
Arg Gly Glu Val Leu Tyr Thr Lys Ser Val Asp Ala Ser Arg Lys Ile
                85                  90                  95

gta ttt ttt gat ata gaa ggg aaa atg att tgg gga tat gat gcg aat      336
Val Phe Phe Asp Ile Glu Gly Lys Met Ile Trp Gly Tyr Asp Ala Asn
            100                 105                 110

aac acg caa aca atg aaa gaa tat gat tgg ata ggt aga cct ata gcc      384
Asn Thr Gln Thr Met Lys Glu Tyr Asp Trp Ile Gly Arg Pro Ile Ala
        115                 120                 125

ata ttt gaa cag caa gag ggc aca aat tca tcg cag tgt aga gaa cgt      432
Ile Phe Glu Gln Gln Glu Gly Thr Asn Ser Ser Gln Cys Arg Glu Arg
    130                 135                 140

ttc att tac gga gaa aac gag aag cat gca caa gat aaa aat gta tgt      480
Phe Ile Tyr Gly Glu Asn Glu Lys His Ala Gln Asp Lys Asn Val Cys
145                 150                 155                 160

ggg cag ttg gtg tat cat tat gat acc gcg ggt cag att cac aca gaa      528
Gly Gln Leu Val Tyr His Tyr Asp Thr Ala Gly Gln Ile His Thr Glu
                165                 170                 175
```

-continued

```
agt ttt tca tta gct ggt atg cca ctt gtt caa agc cgt cgg ctt tta      576
Ser Phe Ser Leu Ala Gly Met Pro Leu Val Gln Ser Arg Arg Leu Leu
            180                 185                 190

agg aat cca gag aaa gta agc gac tgg aca atc cat aag gca gga aat      624
Arg Asn Pro Glu Lys Val Ser Asp Trp Thr Ile His Lys Ala Gly Asn
        195                 200                 205

tgg gaa gat tta ctt gcg att gaa att tac aaa aca agt tgg gaa tat      672
Trp Glu Asp Leu Leu Ala Ile Glu Ile Tyr Lys Thr Ser Trp Glu Tyr
    210                 215                 220

gat gca caa gga aaa atg atg agt caa ata gat gcg aaa ggg aac cga      720
Asp Ala Gln Gly Lys Met Met Ser Gln Ile Asp Ala Lys Gly Asn Arg
225                 230                 235                 240

caa aag gtg acc tac aat gct gtc gga caa caa aag gct att agc ctt      768
Gln Lys Val Thr Tyr Asn Ala Val Gly Gln Gln Lys Ala Ile Ser Leu
                245                 250                 255

acc tta caa aat caa ata gaa cga agt ata gta aat agc gta gaa tat      816
Thr Leu Gln Asn Gln Ile Glu Arg Ser Ile Val Asn Ser Val Glu Tyr
            260                 265                 270

aat gcg gca gga caa gta caa aga act gaa gct ggt aat ggt ata ttg      864
Asn Ala Ala Gly Gln Val Gln Arg Thr Glu Ala Gly Asn Gly Ile Leu
        275                 280                 285

aca gaa tat gtt tat gag gat agt acg cag cgt tta cta aga aaa aga      912
Thr Glu Tyr Val Tyr Glu Asp Ser Thr Gln Arg Leu Leu Arg Lys Arg
    290                 295                 300

gat tca cga aag caa tcc tct ggc cgg cgt gag gtg cta caa gat tat      960
Asp Ser Arg Lys Gln Ser Ser Gly Arg Arg Glu Val Leu Gln Asp Tyr
305                 310                 315                 320

cag tat gaa tat gac cca gta ggc aat att ctt tct att tgt aat caa     1008
Gln Tyr Glu Tyr Asp Pro Val Gly Asn Ile Leu Ser Ile Cys Asn Gln
                325                 330                 335

cct gat tcg ata caa tgt ttt aga aat gaa gct gtg gta tca aag cgt     1056
Pro Asp Ser Ile Gln Cys Phe Arg Asn Glu Ala Val Val Ser Lys Arg
            340                 345                 350

cag tat acc tat gac gcc ttg tat caa ctc att tct agt tca gga aga     1104
Gln Tyr Thr Tyr Asp Ala Leu Tyr Gln Leu Ile Ser Ser Ser Gly Arg
        355                 360                 365

gaa tca gat gca cat cgt aca tcc cat tca ttt cca ccc ttg ata aca     1152
Glu Ser Asp Ala His Arg Thr Ser His Ser Phe Pro Pro Leu Ile Thr
    370                 375                 380

ccg att cct tta gat act agt cga tac gtc aat tat tct gag aca tac     1200
Pro Ile Pro Leu Asp Thr Ser Arg Tyr Val Asn Tyr Ser Glu Thr Tyr
385                 390                 395                 400

cgt tat gat cgt gga ggg aat tta gtc aaa ctg agt cat tat gga gcc     1248
Arg Tyr Asp Arg Gly Gly Asn Leu Val Lys Leu Ser His Tyr Gly Ala
                405                 410                 415

aat cga tat acg aca aat att cat gtg gat cca cat tca aat aga gcg     1296
Asn Arg Tyr Thr Thr Asn Ile His Val Asp Pro His Ser Asn Arg Ala
            420                 425                 430

gta tgg aaa caa ggg aat gac ata ccg aat att tca tct tct ttt gac     1344
Val Trp Lys Gln Gly Asn Asp Ile Pro Asn Ile Ser Ser Ser Phe Asp
        435                 440                 445

caa gcc ggt aat caa caa ttt tta ttc cca gga atg aaa att gag tgg     1392
Gln Ala Gly Asn Gln Gln Phe Leu Phe Pro Gly Met Lys Ile Glu Trp
    450                 455                 460

gat tct cgg aat caa ttg agc cgt gtg aat atg gta gtc cgt gat gga     1440
Asp Ser Arg Asn Gln Leu Ser Arg Val Asn Met Val Val Arg Asp Gly
465                 470                 475                 480

gaa gaa aat gat agg gaa gag tac cat tat gat ggt tca ggt atg cgt     1488
Glu Glu Asn Asp Arg Glu Glu Tyr His Tyr Asp Gly Ser Gly Met Arg
```

```
                485                 490                 495

ata caa aaa cgg tat gtt aga aag gta aag ggt aca acg caa tcg gat      1536
Ile Gln Lys Arg Tyr Val Arg Lys Val Lys Gly Thr Thr Gln Ser Asp
            500                 505                 510

aca gta ttg tat atg cct ggt cta gaa tta cgg aca cgt caa acg ggt      1584
Thr Val Leu Tyr Met Pro Gly Leu Glu Leu Arg Thr Arg Gln Thr Gly
        515                 520                 525

gaa cgt atg gtc gaa tct cta cag ata gtt aca ttg agt atg gga gca      1632
Glu Arg Met Val Glu Ser Leu Gln Ile Val Thr Leu Ser Met Gly Ala
    530                 535                 540

aca caa gta agg gcg cta cat tgg gag aat ggg act caa ccc gag ggg      1680
Thr Gln Val Arg Ala Leu His Trp Glu Asn Gly Thr Gln Pro Glu Gly
545                 550                 555                 560

gtc gag aat aac cag tat cga tat agc ttg aat gat cat gtg caa tcc      1728
Val Glu Asn Asn Gln Tyr Arg Tyr Ser Leu Asn Asp His Val Gln Ser
                565                 570                 575

tct att tta gaa ttg gat gga aat ggg cag atc atg agt aaa gag gaa      1776
Ser Ile Leu Glu Leu Asp Gly Asn Gly Gln Ile Met Ser Lys Glu Glu
            580                 585                 590

ttt tat cca tat ggt gga acg gct ttg tgg aca gct cga aca aaa gtt      1824
Phe Tyr Pro Tyr Gly Gly Thr Ala Leu Trp Thr Ala Arg Thr Lys Val
        595                 600                 605

gag gcg gat tat aaa aca att cga tat tca ggg aaa gaa tta gat gct      1872
Glu Ala Asp Tyr Lys Thr Ile Arg Tyr Ser Gly Lys Glu Leu Asp Ala
    610                 615                 620

aca ggt ctc tat tat tat gga tat cga tat tat atg cca tgg ctc ggg      1920
Thr Gly Leu Tyr Tyr Tyr Gly Tyr Arg Tyr Tyr Met Pro Trp Leu Gly
625                 630                 635                 640

cgt tgg ttg aat cca gat cca gct gga aca gtc gat ggg tta aat tta      1968
Arg Trp Leu Asn Pro Asp Pro Ala Gly Thr Val Asp Gly Leu Asn Leu
                645                 650                 655

tat cgt atg gtc agg aat aat ccg atc aat tta att gac cct gat ggg      2016
Tyr Arg Met Val Arg Asn Asn Pro Ile Asn Leu Ile Asp Pro Asp Gly
            660                 665                 670

aat gca cca ata gaa atg aat gat tat agt aaa gag aat ggc gat tta      2064
Asn Ala Pro Ile Glu Met Asn Asp Tyr Ser Lys Glu Asn Gly Asp Leu
        675                 680                 685

ttt tat gga ctt gct ggg gag aga ggg aaa tat ata aga atg ttc aat      2112
Phe Tyr Gly Leu Ala Gly Glu Arg Gly Lys Tyr Ile Arg Met Phe Asn
    690                 695                 700

caa agc ttt aaa atg aca gat gtt aat agc gat cct atg gtt ata gat      2160
Gln Ser Phe Lys Met Thr Asp Val Asn Ser Asp Pro Met Val Ile Asp
705                 710                 715                 720

caa tac aat aat gaa atc tca aag gtt gtt ttg agt aag aac ata aaa      2208
Gln Tyr Asn Asn Glu Ile Ser Lys Val Val Leu Ser Lys Asn Ile Lys
                725                 730                 735

ggt aca aag ctt gca aat aag ata aaa gtg cca aag aag tta agg gag      2256
Gly Thr Lys Leu Ala Asn Lys Ile Lys Val Pro Lys Lys Leu Arg Glu
            740                 745                 750

ctc att tct aat gag cat aga gga aga tat cct ttg tgg gat gat tat      2304
Leu Ile Ser Asn Glu His Arg Gly Arg Tyr Pro Leu Trp Asp Asp Tyr
        755                 760                 765

ttt tcc aga gga atg gaa aac tca aaa ttt aac ata tcg gct att tat      2352
Phe Ser Arg Gly Met Glu Asn Ser Lys Phe Asn Ile Ser Ala Ile Tyr
    770                 775                 780

aaa gag aca gca gct aaa ttg gat aag gat tat tat cat tca tat gat      2400
Lys Glu Thr Ala Ala Lys Leu Asp Lys Asp Tyr Tyr His Ser Tyr Asp
785                 790                 795                 800

tca aca gga gtt gtt cct aag tta ctt tgg aaa cga gga agc aaa tta      2448
```

-continued

```
Ser Thr Gly Val Val Pro Lys Leu Leu Trp Lys Arg Gly Ser Lys Leu
                805                 810                 815

gga tta gaa att gca gcc tca aat cag aga aca aaa ata cat ttt gtc      2496
Gly Leu Glu Ile Ala Ala Ser Asn Gln Arg Thr Lys Ile His Phe Val
            820                 825                 830

ctt gat gga cta gac atg gaa agt gtg gtt ctc aaa tcg aaa gaa cca      2544
Leu Asp Gly Leu Asp Met Glu Ser Val Val Leu Lys Ser Lys Glu Pro
        835                 840                 845

gga aaa ggc atg gta tat ggc aaa ggt gaa tca att aca gct tct gaa      2592
Gly Lys Gly Met Val Tyr Gly Lys Gly Glu Ser Ile Thr Ala Ser Glu
    850                 855                 860

tta cgc tat gtg tat cga aat tat gac aaa ttg aaa aat agt gtc ttt      2640
Leu Arg Tyr Val Tyr Arg Asn Tyr Asp Lys Leu Lys Asn Ser Val Phe
865                 870                 875                 880

ttc tat aga gat aat gag aag cta aat caa gct cca tgg gaa gat aat      2688
Phe Tyr Arg Asp Asn Glu Lys Leu Asn Gln Ala Pro Trp Glu Asp Asn
                885                 890                 895

ccc ggt tta tgg gca aga tac caa cct act aat aga cct ata aaa aaa      2736
Pro Gly Leu Trp Ala Arg Tyr Gln Pro Thr Asn Arg Pro Ile Lys Lys
            900                 905                 910

cct aat agt gga ggg ctt ttt gga tgc ctt tcg atg agg aga aga taa      2784
Pro Asn Ser Gly Gly Leu Phe Gly Cys Leu Ser Met Arg Arg Arg
        915                 920                 925


<210> SEQ ID NO 17
<211> LENGTH: 927
<212> TYPE: PRT
<213> ORGANISM: Bacillus thuringiensis EG4096

<400> SEQUENCE: 17

Met Asn Met Thr Ser Leu Tyr Tyr Asn Thr Pro Thr Ile Ser Val Ile
1               5                   10                  15

Asp Asn Arg Asn Leu Gln Val Arg Thr Leu Glu Tyr Asn Arg Val Ala
            20                  25                  30

Ala Gly Glu Pro Val Asp Glu Tyr Ile His Arg Asn Ser Tyr Thr Leu
        35                  40                  45

Met Gly His Met Glu Ser Ser Met Asp Pro Arg Leu Phe Ser Leu His
    50                  55                  60

Glu Asp Asp Lys Glu Thr Leu Pro Asn Leu Lys Asn Ile Thr Ser Val
65                  70                  75                  80

Arg Gly Glu Val Leu Tyr Thr Lys Ser Val Asp Ala Ser Arg Lys Ile
                85                  90                  95

Val Phe Phe Asp Ile Glu Gly Lys Met Ile Trp Gly Tyr Asp Ala Asn
            100                 105                 110

Asn Thr Gln Thr Met Lys Glu Tyr Asp Trp Ile Gly Arg Pro Ile Ala
        115                 120                 125

Ile Phe Glu Gln Gln Glu Gly Thr Asn Ser Ser Gln Cys Arg Glu Arg
    130                 135                 140

Phe Ile Tyr Gly Glu Asn Glu Lys His Ala Gln Asp Lys Asn Val Cys
145                 150                 155                 160

Gly Gln Leu Val Tyr His Tyr Asp Thr Ala Gly Gln Ile His Thr Glu
                165                 170                 175

Ser Phe Ser Leu Ala Gly Met Pro Leu Val Gln Ser Arg Arg Leu Leu
            180                 185                 190

Arg Asn Pro Glu Lys Val Ser Asp Trp Thr Ile His Lys Ala Gly Asn
        195                 200                 205

Trp Glu Asp Leu Leu Ala Ile Glu Ile Tyr Lys Thr Ser Trp Glu Tyr
```

-continued

```
    210                 215                 220

Asp Ala Gln Gly Lys Met Met Ser Gln Ile Asp Ala Lys Gly Asn Arg
225                 230                 235                 240

Gln Lys Val Thr Tyr Asn Ala Val Gly Gln Gln Lys Ala Ile Ser Leu
                245                 250                 255

Thr Leu Gln Asn Gln Ile Glu Arg Ser Ile Val Asn Ser Val Glu Tyr
            260                 265                 270

Asn Ala Ala Gly Gln Val Gln Arg Thr Glu Ala Gly Asn Gly Ile Leu
        275                 280                 285

Thr Glu Tyr Val Tyr Glu Asp Ser Thr Gln Arg Leu Leu Arg Lys Arg
    290                 295                 300

Asp Ser Arg Lys Gln Ser Ser Gly Arg Arg Glu Val Leu Gln Asp Tyr
305                 310                 315                 320

Gln Tyr Glu Tyr Asp Pro Val Gly Asn Ile Leu Ser Ile Cys Asn Gln
                325                 330                 335

Pro Asp Ser Ile Gln Cys Phe Arg Asn Glu Ala Val Val Ser Lys Arg
            340                 345                 350

Gln Tyr Thr Tyr Asp Ala Leu Tyr Gln Leu Ile Ser Ser Ser Gly Arg
        355                 360                 365

Glu Ser Asp Ala His Arg Thr Ser His Ser Phe Pro Pro Leu Ile Thr
    370                 375                 380

Pro Ile Pro Leu Asp Thr Ser Arg Tyr Val Asn Tyr Ser Glu Thr Tyr
385                 390                 395                 400

Arg Tyr Asp Arg Gly Gly Asn Leu Val Lys Leu Ser His Tyr Gly Ala
                405                 410                 415

Asn Arg Tyr Thr Thr Asn Ile His Val Asp Pro His Ser Asn Arg Ala
            420                 425                 430

Val Trp Lys Gln Gly Asn Asp Ile Pro Asn Ile Ser Ser Ser Phe Asp
        435                 440                 445

Gln Ala Gly Asn Gln Gln Phe Leu Phe Pro Gly Met Lys Ile Glu Trp
    450                 455                 460

Asp Ser Arg Asn Gln Leu Ser Arg Val Asn Met Val Val Arg Asp Gly
465                 470                 475                 480

Glu Glu Asn Asp Arg Glu Glu Tyr His Tyr Asp Gly Ser Gly Met Arg
                485                 490                 495

Ile Gln Lys Arg Tyr Val Arg Lys Val Lys Gly Thr Thr Gln Ser Asp
            500                 505                 510

Thr Val Leu Tyr Met Pro Gly Leu Glu Leu Arg Thr Arg Gln Thr Gly
        515                 520                 525

Glu Arg Met Val Glu Ser Leu Gln Ile Val Thr Leu Ser Met Gly Ala
    530                 535                 540

Thr Gln Val Arg Ala Leu His Trp Glu Asn Gly Thr Gln Pro Glu Gly
545                 550                 555                 560

Val Glu Asn Asn Gln Tyr Arg Tyr Ser Leu Asn Asp His Val Gln Ser
                565                 570                 575

Ser Ile Leu Glu Leu Asp Gly Asn Gly Gln Ile Met Ser Lys Glu Glu
            580                 585                 590

Phe Tyr Pro Tyr Gly Gly Thr Ala Leu Trp Thr Ala Arg Thr Lys Val
        595                 600                 605

Glu Ala Asp Tyr Lys Thr Ile Arg Tyr Ser Gly Lys Glu Leu Asp Ala
    610                 615                 620

Thr Gly Leu Tyr Tyr Tyr Gly Tyr Arg Tyr Tyr Met Pro Trp Leu Gly
625                 630                 635                 640
```

-continued

```
Arg Trp Leu Asn Pro Asp Pro Ala Gly Thr Val Asp Gly Leu Asn Leu
                645                 650                 655

Tyr Arg Met Val Arg Asn Asn Pro Ile Asn Leu Ile Asp Pro Asp Gly
            660                 665                 670

Asn Ala Pro Ile Glu Met Asn Asp Tyr Ser Lys Glu Asn Gly Asp Leu
        675                 680                 685

Phe Tyr Gly Leu Ala Gly Glu Arg Gly Lys Tyr Ile Arg Met Phe Asn
    690                 695                 700

Gln Ser Phe Lys Met Thr Asp Val Asn Ser Asp Pro Met Val Ile Asp
705                 710                 715                 720

Gln Tyr Asn Asn Glu Ile Ser Lys Val Val Leu Ser Lys Asn Ile Lys
                725                 730                 735

Gly Thr Lys Leu Ala Asn Lys Ile Lys Val Pro Lys Lys Leu Arg Glu
            740                 745                 750

Leu Ile Ser Asn Glu His Arg Gly Arg Tyr Pro Leu Trp Asp Asp Tyr
        755                 760                 765

Phe Ser Arg Gly Met Glu Asn Ser Lys Phe Asn Ile Ser Ala Ile Tyr
    770                 775                 780

Lys Glu Thr Ala Ala Lys Leu Asp Lys Asp Tyr Tyr His Ser Tyr Asp
785                 790                 795                 800

Ser Thr Gly Val Val Pro Lys Leu Leu Trp Lys Arg Gly Ser Lys Leu
                805                 810                 815

Gly Leu Glu Ile Ala Ala Ser Asn Gln Arg Thr Lys Ile His Phe Val
            820                 825                 830

Leu Asp Gly Leu Asp Met Glu Ser Val Val Leu Lys Ser Lys Glu Pro
        835                 840                 845

Gly Lys Gly Met Val Tyr Gly Lys Gly Glu Ser Ile Thr Ala Ser Glu
    850                 855                 860

Leu Arg Tyr Val Tyr Arg Asn Tyr Asp Lys Leu Lys Asn Ser Val Phe
865                 870                 875                 880

Phe Tyr Arg Asp Asn Glu Lys Leu Asn Gln Ala Pro Trp Glu Asp Asn
                885                 890                 895

Pro Gly Leu Trp Ala Arg Tyr Gln Pro Thr Asn Arg Pro Ile Lys Lys
            900                 905                 910

Pro Asn Ser Gly Gly Leu Phe Gly Cys Leu Ser Met Arg Arg Arg
        915                 920                 925
```